(12) United States Patent
Kong et al.

(10) Patent No.: US 11,564,954 B2
(45) Date of Patent: Jan. 31, 2023

(54) TUMOR-DELIVERED MULTI-TARGET THERAPEUTICS FOR COLON CANCER

(71) Applicant: Arizona Board of Regents on behalf of Arizona State University, Scottsdale, AZ (US)

(72) Inventors: Wei Kong, Phoenix, AZ (US); Lingchen Fu, Tempe, AZ (US); Yixin Shi, Phoenix, AZ (US)

(73) Assignee: ARIZONA BOARD OF REGENTS ON BEHALF OF ARIZONA STATE UNIVERSITY, Scottsdale, AZ (US)

( * ) Notice: Subject to any disclaimer, the term of this patent is extended or adjusted under 35 U.S.C. 154(b) by 0 days.

(21) Appl. No.: 17/433,103

(22) PCT Filed: Feb. 20, 2020

(86) PCT No.: PCT/US2020/019112
§ 371 (c)(1),
(2) Date: Aug. 23, 2021

(87) PCT Pub. No.: WO2020/172463
PCT Pub. Date: Aug. 27, 2020

(65) Prior Publication Data
US 2022/0143105 A1 May 12, 2022

Related U.S. Application Data
(60) Provisional application No. 62/809,232, filed on Feb. 22, 2019.

(51) Int. Cl.
| | | |
|---|---|---|
| *A61K 35/74* | (2015.01) |
| *A61P 35/04* | (2006.01) |
| *C12N 1/20* | (2006.01) |
| *C07K 14/705* | (2006.01) |
| *C12N 15/74* | (2006.01) |
| *C12R 1/42* | (2006.01) |

(52) U.S. Cl.
CPC .............. *A61K 35/74* (2013.01); *A61P 35/04* (2018.01); *C07K 14/70521* (2013.01); *C12N 1/205* (2021.05); *C12N 15/74* (2013.01); *C12R 2001/42* (2021.05)

(58) Field of Classification Search
USPC ...................................... 424/93.45
See application file for complete search history.

(56) References Cited

U.S. PATENT DOCUMENTS

| | | |
|---|---|---|
| 2003/0165500 A1 | 9/2003 | Rhee et al. |
| 2010/0317084 A1 | 12/2010 | Curtiss, III |
| 2017/0224806 A1 | 8/2017 | Curtiss, III et al. |
| 2017/0275340 A1* | 9/2017 | Yun .......... C07K 14/71 |
| 2017/0306338 A1* | 10/2017 | Curtiss, III .............. C12N 1/36 |

FOREIGN PATENT DOCUMENTS

WO    2018197621 A1    11/2018

OTHER PUBLICATIONS

International Search Report and Written Opinion in corresponding PCT Application No. PCT/US2020/019112, dated Jun. 11, 2020.

* cited by examiner

*Primary Examiner* — Jana A Hines
*Assistant Examiner* — Khatol S Shahnan Shah
(74) *Attorney, Agent, or Firm* — Quarles & Brady LLP

(57) ABSTRACT

The present disclosure relates to genetically modified strains of *Salmonella*, engineered to be tumor navigating, self-eradicating, and armed with decoy polypeptides that bind endogenous ligand and block activation of signal transduction cascades associated with cancer cell proliferation and tumor growth. Also provided herein are methods of producing and methods of using such genetically modified *Salmonella* strains to treat cancer.

3 Claims, 11 Drawing Sheets
(5 of 11 Drawing Sheet(s) Filed in Color)
Specification includes a Sequence Listing.

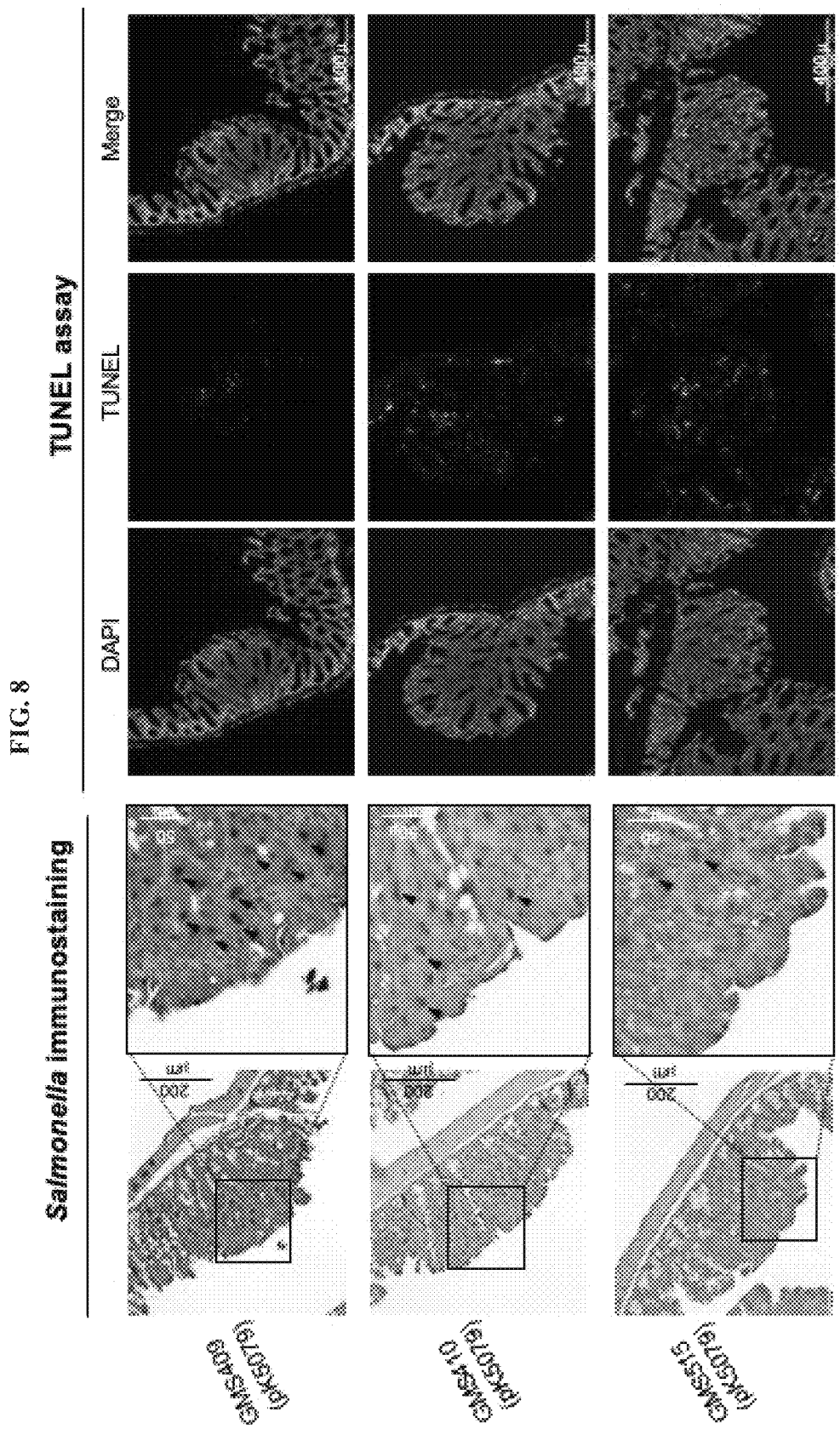

SEQUENCE LISTING

```
<160> NUMBER OF SEQ ID NOS: 24

<210> SEQ ID NO 1
<211> LENGTH: 6192
<212> TYPE: DNA
<213> ORGANISM: Artificial Sequence
<220> FEATURE:
<223> OTHER INFORMATION: Synthetic- plasmid pK-FZD (pYA3681 encoding
      human Wnt binding domains of FZD)

<400> SEQUENCE: 1
agatctagcc cgcctaatga gcgggctttt ttttaattcg caattccccg atgcataatg      60
tgcctgtcaa atggacgaag cagggattct gcaaaccctca tgctactccg tcaagccgtc     120
aattgtctga ttcgttacca attatgacaa cttgacggct acatcattca cttttcttc      180 acaaccggca cggaactcgc tcgggctggc cccggtgcat tttttaaata cccgcgagaa     240
atagagttga tcgtcaaaac caacattgcg accgacggtg gcgataggca tccgggtggt     300
gctcaaaagc agcttcgcct ggctgatacg ttggtcctcg cgccagctta agacgctaat     360
ccctaactgc tggcggaaaa gatgtgacag acgcgacggc gacaagcaaa catgctgtgc     420
gacgctggcg atatcaaaat tgctgtctgc caggtgatcg ctgatgtact gacaagcctc     480
gcgtacccga ttatccatcg gtggatggag cgactcgtta atcgcttcca tgcgccgcag     540
taacaattgc tcaagcagat ttatcgccag cagctccgaa tagcgccctt ccccttgccc     600
ggcgttaatg atttgcccaa acaggtcgct gaaatgcggc tggtgcgctt catccgggcg     660
aaagaacccc gtattggcaa atattgacgg ccagttaagc cattcatgcc agtaggcgcg     720
cggacgaaag taaacccact ggtgatacca ttcgcgagcc tccggatgac gaccgtagtg     780
atgaatctct cctggcggga acagcaaaat atcaccggt cggcaaacaa attctcgtcc     840 ctgattttc accacccct gaccgcgaat ggtgagattg agaatataac ctttcattcc     900
```

```
cagcggtcgg tcgataaaaa aatcgagata accgttggcc tcaatcggcg ttaaacccgc    960
caccagatgg gcattaaacg agtatcccgg cagcagggga tcattttgcg cttcagccat   1020
acttttcata ctcccgccat tcagagaaga aaccaattgt ccatattgca tcagacattg   1080
ccgtcactgc gtcttttact ggctcttctc gctaaccaaa ccggtaaccc cgcttattaa   1140
aagcattctg taacaaagcg ggaccaaagc catgacaaaa acgcgtaaca aaagtgtcta   1200
taatcacggc agaaaagtcc acattgatta tttgcacggc gtcacacttt gctatgccat   1260
agcattttta tccataagat tagcggatcc tacctgacgc tttttatcgc aactctctac   1320
tgtttctcca tacccgtttt tttgggctag cgaattctga gaacaaacta aatggataaa   1380
tttcgtgttc aggggccaac gaagctccag ggcgaagtca caatttccgg cgctaaaaat   1440
gctgctctgc ctatcctttt tgccgcacta ctggcggaag aaccggtaga gatccagaac   1500
gtcccgaaac tgaaagacgt cgatacatca atgaagctgc taagccagct gggtgcgaaa   1560
gtagaacgta atggttctgt gcatattgat gcccgcgacg ttaatgtatt ctgcgcacct   1620
tacgatctgg ttaaaaccat gcgtgcttct atctgggcgt ggggccgct ggtagcgcgc   1680 tttggtcagg ggcaagtttc actacctggc ggttgtacga tcggtgcgcg tccggttgat   1740
ctacacattt ctggcctcga acaattaggc gcgaccatca aactggaaga aggttacgtt   1800
aaagcttccg tcgatggtcg tttgaaaggt gcacatatcg tgatggataa agtcagcgtt   1860
ggcgcaacgg tgaccatcat gtgtgctgca accctggcgg aaggcaccac gattattgaa   1920
aacgcagcgc gtgaaccgga aatcgtcgat accgcgaact tcctgattac gctgggtgcg   1980
aaaattagcg gtcagggcac cgatcgtatc gtcatcgaag gtgtggaacg tttaggcggc   2040
ggtgtctatc gcgttctgcc ggatcgtatc gaaaccggta cttcctggt ggcggcggcg   2100 atttctcgcg gcaaaattat ctgccgtaac gcgcagccag atactctcga cgccgtgctg   2160
gcgaaactgc gtgacgctgg agcggacatc gaagtcggcg aagactggat tagcctggat   2220
atgcatggca aacgtccgaa ggctgttaac gtacgtaccg cgccgcatcc ggcattcccg   2280
accgatatgc aggcccagtt cacgctgttg aacctggtgg cagaagggac cgggtttatc   2340
accgaaacgg tctttgaaaa ccgctttatg catgtgccag agctgagccg tatgggcgcg   2400
cacgccgaaa tcgaaagcaa taccgttatt tgtcacggtg ttgaaaaact ttctggcgca   2460
caggttatgg caaccgatct gcgtgcatca gcaagcctgg tgctggctgg ctgtattgcg   2520
gaagggacga cggtggttga tcgtatttat cacatcgatc gtggctacga acgcattgaa   2580
gacaaactgc gcgctttagg tgcaaatatt gagcgtgtga aaggcgaata agaattcagg   2640
aaaaaaacgc tgtgaaaaat gttggtttta tcggctggcg cggaatggtc ggctctgttc   2700
tcatgcaacg catggtagag gagcgcgatt tcgacgctat tcgccctgtt ttcttttcta   2760
cctcccagtt tggacaggcg gcgcccacct tcggcgacac ctccaccggc acgctacagg   2820
acgcttttga tctggatgcg ctaaaagcgc tcgatatcat cgtgacctgc agggcggcg   2880 attataccaa cgaaatttat ccaaagctgc gcgaaagcgg atggcagggt tactggattg   2940
atgcggcttc tacgctgcgc atgaaagatg atgccattat tattctcgac ccggtcaacc   3000
aggacgtgat taccgacggc ctgaacaatg gcgtgaagac ctttgtgggc ggtaactgta   3060
ccgttagcct gatgttgatg tcgctgggcg gtctctttgc ccataatctc gttgactggg   3120
tatccgtcgc gacctatcag gccgcctccg gcggcggcgc gcgccatatg cgcgagctgt   3180
taacccagat gggtcagttg tatggccatg tcgccgatga actggcgacg ccgtcttccg   3240
caattcttga tattgaacgc aaagttacgg cattgacccg cagcggcgag ctgccggttg   3300
```

-continued

```
ataactttgg cgtaccgctg gcgggaagcc tgatcccctg gatcgacaaa cagctcgata      3360
acggccagag ccgcgaagag tggaaaggcc aggcggaaac caacaagatt ctcaatactg      3420
cctctgtgat tccggttgat ggtttgtgtg tgcgcgtcgg cgcgctgcgc tgtcacagcc      3480
aggcgttcac catcaagctg aaaaaagagg tatccattcc gacggtggaa gaactgctgg      3540
cggcacataa tccgtgggcg aaagtggtgc cgaacgatcg tgatatcact atgcgcgaat      3600
taaccccggc ggcggtgacc ggcacgttga ctacgccggt tggtcgtctg cgtaagctga      3660
acatggggcc agagttcttg tcggcgttta ccgtaggcga ccagttgtta tggggcgccg      3720
ccgagccgct gcgtcgaatg ctgcgccagt tggcgtagtc tagctgcacg ataccgtcga      3780
cttgtacata gactcgctcc gaaattaaag aacacttaaa ttatctacta aaggaatctt      3840
tagtcaagtt tatttaagat gacttaacta tgaatacaca attgatgggt gagcgtagga      3900
gcatgcttat gcgaaaggcc atcctgacgg atggcctttt tggatcttcc ggaagacctt      3960
ccattctgaa atgagctgtt gacaattaat catccggctc gtataatgtg tggaattgtg      4020
agcggataac aatttcacac aggaaacaga ccatggacca cggcttctgc cagccgatct      4080
ctatcccgct gtgcaccgac atcgcgtaca accagaccat catgccgaac ctgctgggcc      4140
acaccaacca ggaagacgcg ggcctggaag ttaccagtt ctacccgctg gttaaagttc       4200
agtgctctcc ggaactgcgt ttcttcctgt gctctatgta cgcgccggtt gcaccgttc       4260 tggaacaggc gatcccgccg tgccgttcta tctgcgaacg tgcgcgtcag ggctgcgaag      4320
cgctgatgaa caaattcggc ttccagtggc cggaacgtct gcgttgcgaa cacttcccgc      4380
gtcacggcgc ggaacagatc tgcgttggcc agaaccactc tgaagacggc gcgccgtaat      4440
agcccgggga tccgtcgacc tgcagccaag ctcccaagct tggctgtttt ggcggatgag      4500
agaagatttt cagcctgata cagattaaat cagaacgcag aagcggtctg ataaaacaga      4560
atttgcctgg cggcagtagc gcggtggtcc cacctgaccc catgccgaac tcagaagtga      4620
aacgccgtag cgccgatggt agtgtggggt ctccccatgc gagagtaggg aactgccagg      4680
catcaaataa aacgaaaggc tcagtcgaaa gactgggcct ttcgttttat ctgttgtttg      4740
tcggtgaacg ctctcctgag taggacaaat ccgccgggag cggatttgaa cgttgcgaag      4800
caacggcccg gagggtggcg gcaggacgc ccgccataaa ctgccaggca tcaaattaag       4860
cagaaggcca tcctgacgga tggccttttt gcgtttctac aaactctttt gtttattttt      4920
ctaaatacat tcaaatatgt atccgctcat gagacaataa ccctgataaa tgcttcaata      4980
atggaagatc ttccaacatc acaggtaaac agaaacgtcg ggtcgatcgg gaaattcttt      5040
cccggacggc gcggggttgg gcaagccgca ggcgcgtcag tgcttttagc gggtgtcggg      5100
gcgcagccat gacccagtca cgtagcgata gcggagtgta tactggctta actatgcggc      5160
atcagagcag attgtactga gagtgcacca tatgcggtgt gaaataccgc acagatgcgt      5220
aaggagaaaa taccgcatca ggcgctcttc cgcttcctcg ctcactgact cgctgcgctc      5280
ggtcgttcgg ctgcggcgag cggtatcagc tcactcaaag gcggtaatac ggttatccac      5340
agaatcaggg gataacgcag gaaagaacat gtgagcaaaa ggccagcaaa aggccaggaa      5400
ccgtaaaaag gccgcgttgc tggcgttttt ccataggctc cgcccccctg acgagcatca      5460
caaaaatcga cgctcaagtc agaggtggcg aaacccgaca ggactataaa gataccaggc      5520
gtttccccct ggaagctccc tcgtgcgctc tcctgttccg accctgccgc ttaccggata      5580
cctgtccgcc tttctccctt cgggaagcgt ggcgctttct catagctcac gctgtaggta      5640
tctcagttcg gtgtaggtcg ttcgctccaa gctgggctgt gtgcacgaac cccccgttca      5700
```

```
gcccgaccgc tgcgccttat ccggtaacta tcgtcttgag tccaacccgg taagacacga    5760
cttatcgcca ctggcagcag ccactggtaa caggattagc agagcgaggt atgtaggcgg    5820
tgctacagag ttcttgaagt ggtggcctaa ctacggctac actagaagga cagtatttgg    5880
tatctgcgct ctgctgaagc cagttacctt cggaaaaaga gttggtagct cttgatccgg    5940
caaacaaacc accgctggta gcggtggttt ttttgtttgc aagcagcaga ttacgcgcag    6000
aaaaaaagga tctcaagaag atcctttgat cttttctacg gggtctgacg ctcagtggaa    6060
cgaaaactca cgttaaggga ttttggtcat gagattatca aaaggatctt cacctagat     6120 ccttttaaat taaaaatgaa gttttaaatc aatctaaagt atatatgagt aaacttggtc     6180
tgacagtcta ga                                                         6192

<210> SEQ ID NO 2
<211> LENGTH: 7346
<212> TYPE: DNA
<213> ORGANISM: Artificial Sequence
<220> FEATURE:
<223> OTHER INFORMATION: Synthetic- plasmid pK-DFZD (pYA4545 encoding
      human Wnt binding domains of FZD)

<400> SEQUENCE: 2
gactcttcgc gatgtacggg ccagatatac gcgttaactg cagtctagat tatgcgaaag      60
gccatcctga cggatggcct ttttgtttaa acgatccgc gacattgatt attgactagt       120
tattaatagt aatcaattac ggggtcatta ggggactttc cggggacttt cctccccacg      180
cgggggactt tccgccacgg gcggggactt tccggggact ttccgttcat agcccatata      240
tggagttccg cgttacataa cttacggtaa atggcccgcc tggctgaccg cccaacgacc      300
cccgcccatt gacgtcaata atgacgtatg ttcccatagt aacgccaata gggactttcc      360
attgacgtca atgggtggac tatttacggt aaactgccca cttggcagta catcaagtgt      420
atcatatgcc aagtacgccc cctattgacg tcaatgacgg taaatggccc gcctggcatt      480
atgcccagta catgacctta tgggactttc ctacttggca gtacatctac gtattagtca      540
tcgctattac catggtgatg cggttttggc agtacatcaa tgggcgtgga tagcggtttg      600
actcacgggg atttccaagt ctccacccca ttgacgtcaa tgggagtttg ttttggcacc      660
aaaatcaacg ggactttcca aaatgtcgta caactccgc cccattgacg caaatgggcg       720
gtaggcgtgt acggtgggag gtctatataa gcagagctct ctggctaact agagaaccca      780
ctgcttactg gcttatcgaa attaatacga ctcactatag ggagacccaa gctggctagc      840
gtttaaactt aagcttggta ccaccatgga ccacggcttc tgccagccca tctccatccc      900
gctgtgcacg gacatcgcct acaaccgac catcatgccc aaccttctgg ccacacgaa       960 ccaggaggac gcaggcctag aggtgcacca gttctatccg ctggtgaagg tgcagtgctc     1020
gcccgaactg cgcttcttcc tgtgctccat gtacgcaccc gtgtgcaccg tgctggaaca     1080
ggccatcccg ccgtgccgct ctatctgtga gcgcgcgcg cagggctgcg aagccctcat     1140
gaacaagttc ggttttcagt ggcccgagcg cctgcgctgc gagcacttcc cgcgccacgg     1200
cgccgagcag atctgcgtcg gccagaacca ctccgaggac ggagctccct aatagctcga     1260
gaatgcttcg agcagacatg ataagataca ttgatgagtt tggacaaacc acaactagaa     1320
tgcagtgaaa aaaatgcttt atttgtgaaa tttgtgatgc tattgcttta tttgtaacca     1380
ttataagctg caataaacaa gttaacaaca acaattgcat tcattttatg tttcaggttc     1440
agggggagat gtgggaggtt ttttaaagca agtaaaacct ctacaaatgt ggtaaaatcc     1500
```

-continued

```
gataaggatc gatccggggc atgcaaccag ctgtggaatg tgtgtcagtt agggtgtgga      1560
aagtccccag gctccccagc aggcagaagt atgcaaagca tgtggggatg cggtgggctc      1620
tatggcttct actgggcggt tttatggaca gcaagcgaac cggaattgcc agctggggcg      1680
ccctctggta aggttgggaa gccctgcaaa gtaaactgga tggctttctc gccgccaagg      1740
atctgtcgac ccctagattt cagtgcaatt tatctcttca aatgtagcac ctgaagtcag      1800
ccccatacga tataagttgt tggaagatct agcccgccta atgagcgggc ttttttttaa      1860
ttcgcaattc cccgatgcat aatgtgcctg tcaaatggac gaagcaggga ttctgcaaac      1920
cctatgctac tccgtcaagc cgtcaattgt ctgattcgtt accaattatg acaacttgac      1980
ggctacatca ttcactttt cttcacaacc ggcacgaaac tcgctcgggc tggccccggt      2040
gcatttttta aatactcgcg agaaatagag ttgatcgtca aaaccaacat tgcgaccgac      2100
ggtggcgata ggcatccggg tagtgctcaa aagcagcttc gcctgactaa tgcgttggtc      2160
ctcgcgccag cttaagacgc taatccctaa ctgctggcgg aaaagatgtg acagacgcga      2220
cggcgacaag caaacatgct gtgcgacgct ggcgatatca aaattgctgt ctgccaggtg      2280
atcgctgatg tactgacaag cctcgcgtac ccgattatcc atcggtggat ggagcgactc      2340
gttaatcgct tccatgcgcc gcagtaacaa ttgctcaagc agatttatcg ccagcagctc      2400
cgaatagcgc ccttcccctt gcccggcgtt aatgatttgc ccaaacaggt cgctgaaatg      2460
cggctggtgc gcttcatccg ggcgaaagaa acccgtattg gcaaatattg acggccagtt      2520
aagccattca tgccagtagg cgcgcggacg aaagtaaacc cactggtgat accattcgcg      2580
agcctccgga tgacgaccgt agtgatgaat ctctcctggc gggaacagca aaatatcacc      2640
cggtcggcag acaaattctc gtccctgatt tttcaccacc ccctgaccgc gaatggtgag      2700
attgagaata taacctttca ttcccagcgg tcggtcgata aaaaaatcga gataaccgtt      2760
ggcctcaatc ggcgttaaac ccgccaccag atgggcgtta acgagtatc ccggcagcag      2820 gggatcattt tgcgcttcag ccatactttt catactccca ccattcagag aagaaaccaa      2880
ttgtccatat tgcatcagac attgccgtca ctgcgtcttt tactggctct tctcgctaac      2940
ccaaccggta accccgctta ttaaaagcat tctgtaacaa agcgggacca aagccatgac      3000
aaaaacgcgt aacaaaagtg tctataatca cggcagaaaa gtccacattg attatttgca      3060
cggcgtcaca ctttgctatg ccatagcatt tttatccata agattagcgg atcctacctg      3120 acgctttta tcgcaactct ctactgtttc tccatacccg ttttttggg ctagcgaatt      3180 ctgagaacaa actaagtgga taaatttcgt gttcaggggc caacgaagct ccagggcgaa      3240
gtcacaattt ccggcgctaa aaatgctgct ctgcctatcc tttttgccgc actactggcg      3300
gaagaaccgg tagagatcca gaacgtcccg aaactgaaag acgtcgatac atcaatgaag      3360
ctgctaagcc agctgggtgc gaaagtagaa cgtaatggtt ctgtgcatat tgatgcccgc      3420
gacgttaatg tattctcgcg cccttacgat ctggttaaaa ccatgcgtgc ttctatctgg      3480 gcgctgggc cgctggtagc gcgctttggt caggggcaag tttcactacc tggcggttgt      3540
acgatcggtg cgcgtccggt tgatctacac atttctggcc tcgaacaatt aggcgcgacc      3600
atcaaactgg aagaaggtta cgttaaagct tccgtcgatg tcgtttgaa aggtgcacat      3660 atcgtgatgg ataaagtcag cgttggcgca acggtgacca tcatgtgtgc tgcaaccctg      3720
gcggaaggca ccacgattat tgaaaacgca gcgcgtgaac cggaaatcgt cgataccgcg      3780
aacttcctga ttacgctggg tgcgaaaatt agcggtcagg gcaccgatcg tatcgtcatc      3840
gaaggtgtgg aacgtttagg cggcggtgtc tatcgcgttc tgccggatcg tatcgaaacc      3900
```

```
ggtactttcc tggtggcggc ggcgatttct cgcggcaaaa ttatctgccg taacgcgcag    3960
ccagatactc tcgacgccgt gctggcgaaa ctgcgtgacg ctggagcgga catcgaagtc    4020
ggcgaagact ggattagcct ggatatgcat ggcaaacgtc cgaaggctgt taacgtacgt    4080
accgcgccgc atccggcatt cccgaccgat atgcaggccc agttcacgct gttgaacctg    4140
gtggcagaag ggaccgggtt tatcaccgaa acggtctttg aaaaccgctt tatgcatgtg    4200
ccagagctga gccgtatggg cgcgcacgcc gaaatcgaaa gcaataccgt tatttgtcac    4260
ggtgttgaaa aactttctgg cgcacaggtt atggcaaccg atctgcgtgc atcagcaagc    4320
ctggtgctgg ctggctgtat tgcggaaggg acgacggtgg ttgatcgtat ttatcacatc    4380
gatcgtggct acgaacgcat tgaagacaaa ctgcgcgctt taggtgcaaa tattgagcgt    4440
gtgaaaggcg aataagaatt caggaaaaaa acgctgtgaa aaatgttggt tttatcggct    4500
ggcgcggaat ggtcggctct gttctcatgc aacgcatggt agaggagcgc gatttcgacg    4560
ctattcgccc tgttttctttt tctacctccc agtttggaca ggcggcgccc accttcggcg    4620
acacctccac cggcacgcta caggacgctt ttgatctgga tgcgctaaaa gcgctcgata    4680
tcatcgtgac ctgccagggc ggcgattata ccaacgaaat ttatccaaag ctgcgcgaaa    4740
gcggatggca gggttactgg attgatgcgg cttctacgct gcgcatgaaa gatgatgcca    4800
ttattattct cgacccggtc aaccaggacg tgattaccga cggcctgaac aatggcgtga    4860
agacctttgt gggcggtaac tgtaccgtta gcctgatgtt gatgtcgctg gcggtctct    4920 ttgcccataa tctcgttgac tgggtatccg tcgcgaccta tcaggccgcc tccggcggcg    4980
gcgcgcgcca tgcgcgcgag ctgttaaccc agatgggtca gttgtatggc catgtcgccc    5040
atgaactggc gacgccgtct tccgcaattc ttgatattga acgcaaagtt acggcattga    5100
cccgcagcgg cgagctgccg gttgataact ttggcgtacc gctggcggga agcctgatcc    5160
cctggatcga caaacagctc gataacggcc agagccgcga agagtggaaa ggccaggcgg    5220
aaaccaacaa gattctcaat actgcctctg tgattccggt tgatggtttg tgtgtgcgcg    5280
tcggcgcgct gcgctgtcac agccaggcgt tcaccatcaa gctgaaaaaa gaggtatcca    5340
ttccgacggt ggaagaactg ctggcggcac ataatccgtg ggcgaaagtg gtgccgaacg    5400
atcgtgatat cactatgcgc gaattaaccc cggcggcggt gaccggcacg ttgactacgc    5460
cggttggtcg tctgcgtaag ctgaacatgg ggccagagtt cttgtcggcg tttaccgtag    5520
gcgaccagtt gttatggggc gccgccgagc cgctgcgtcg aatgctgcgc cagttggcgt    5580
agtctagctg cacgataccg tcgacttgta catagactcg ctccgaaatt aaagaacact    5640
taaattatct actaaaggaa tctttagtca agtttattta agatgactta actatgaata    5700
cacaattgat gggtgagcgt aggatcttcc attattgaag catttatcag ggttattgtc    5760
tcatgagctt ggctgttttg gcggatgaga aagattttc agcctgatac agattaaatc    5820
agaacgcaga agcggtctga taaaacagtt tgcctggcgg cagtagcgcg gtggtcccac    5880
ctgaccccat gccgaactca gaagtgaaac gccgtagcgc cgatggtagt gtggggtctc    5940
cccatgcgag agtagggaac tgccaggcat caaataaaac gaaaggctca gtcgaaagac    6000
tgggcctttc gttttatctg ttgtttgtcg gtgaacgctc tcctgagtag acaaatccg    6060 ccgggagcgg atttgaacgt tgcgaagcaa cggcccggag ggtggcgggc aggacgcccg    6120
ccataaactg ccaggcatca aattaagcag aaggccatcc tgacggatgg ccttttttgcg    6180 tttctacaaa ctcttttttgt ttattttttct aaatacattt aaatatgtat ccgctcatga    6240
gacaataacc ctgataaatg cttcaataat ggaagatctt ccaacatcac aggtaaacag    6300
```

| | |
|---|---|
| aaacgtcggg tcgatcggga aattctttcc cggacggcgc ggggttgggc aagccgcagg | 6360 |
| cgcgtcagtg cttttagcgg gtgtcggggc agccctgaac cagtcacggg atcgatctgt | 6420 |
| gcggtatttc acaccgcata caggtggcac ttttcgggga aatgtgcgcg gaacccctat | 6480 |
| ttgtttattt ttctaaatac attcaaatat gtatccgctc atgagacaat aaccctgata | 6540 |
| aatgcttcaa taatagcacg tgctaaaact tcattttaa tttaaaagga tctaggtgaa | 6600 |
| gatccttttt gataatctca tgaccaaaat cccttaacgt gagttttcgt tccactgagc | 6660 |
| gtcagacccc gtagaaaaga tcaaaggatc ttcttgagat cctttttttc tgcgcgtaat | 6720 |
| ctgctgcttg caaacaaaaa aaccaccgct accagcggtg gtttgtttgc cggatcaaga | 6780 |
| gctaccaact cttttccga aggtaactgg cttcagcaga gcgcagatac caaatactgt | 6840 |
| ccttctagtg tagccgtagt taggccacca cttcaagaac tctgtagcac cgcctacata | 6900 |
| cctcgctctg ctaatcctgt taccagtggc tgctgccagt ggcgataagt cgtgtcttac | 6960 |
| cgggttggac tcaagacgat agttaccgga taaggcgcag cggtcgggct gaacggggggg | 7020 |
| ttcgtgcaca cagcccagct tggagcgaac gacctacacc gaactgagat acctacagcg | 7080 |
| tgagctatga gaaagcgcca cgcttcccga agggagaaag gcggacaggt atccggtaag | 7140 |
| cggcagggtc ggaacaggag agcgcacgag ggagcttcca gggggaaacg cctggtatct | 7200 |
| ttatagtcct gtcgggtttc gccacctctg acttgagcgt cgatttttgt gatgctcgtc | 7260 |
| aggggggcgg agcctatgga aaaacgccag caacgcggcc tttttacggt tcctggcctt | 7320 |
| ttgctggcct tttgctcaca tgttct | 7346 |

<210> SEQ ID NO 3
<211> LENGTH: 7662
<212> TYPE: DNA
<213> ORGANISM: Artificial Sequence
<220> FEATURE:
<223> OTHER INFORMATION: Synthetic- plasmid pK-LRP6 (pYA3681 encoding human Wnt binding domains of LRP6)

<400> SEQUENCE: 3

| | |
|---|---|
| agatctagcc cgcctaatga gcgggctttt ttttaattcg caattccccg atgcataatg | 60 |
| tgcctgtcaa atggacgaag cagggattct gcaaacccta tgctactccg tcaagccgtc | 120 |
| aattgtctga ttcgttacca attatgacaa cttgacggct acatcattca cttttcttc | 180 |
| acaaccggca cggaactcgc tcgggctggc cccggtgcat ttttaaata cccgcgagaa | 240 |
| atagagttga tcgtcaaaac caacattgcg accgacggtg gcgataggca tccgggtggt | 300 |
| gctcaaaagc agcttcgcct ggctgatacg ttggtcctcg cgccagctta agacgctaat | 360 |
| ccctaactgt tggcggaaaa gatgtgacag acgcgacggc gacaagcaaa catgctgtgc | 420 |
| gacgctggcg atatcaaaat tgctgtctgc caggtgatcg ctgatgtact gacaagcctc | 480 |
| gcgtacccga ttatccatcg gtggatgag cgactcgtta atcgcttcca tgcgccgcag | 540 |
| taacaattgc tcaagcagat ttatcgccag cagctccgaa tagcgccctt ccccttgccc | 600 |
| ggcgttaatg atttgcccaa acaggtcgct gaaatgcggc tggtgcgctt catccgggcg | 660 |
| aaagaacccc gtattggcaa atattgacgg ccagttaagc cattcatgcc agtaggcgcg | 720 |
| cggacgaaag taaacccact ggtgatacca ttcgcgagcc tccggatgac gaccgtagtg | 780 |
| atgaatctct cctggcggga acagcaaaat atcaccggt cggcaaacaa attctcgtcc | 840 |
| ctgatttttc accacccct gaccgcgaat ggtgagattg agaatataac ctttcattcc | 900 |
| cagcggtcgg tcgataaaaa aatcgagata accgttggcc tcaatcggcg ttaaacccgc | 960 |

-continued

```
caccagatgg gcattaaacg agtatcccgg cagcagggga tcattttgcg cttcagccat   1020
acttttcata ctcccgccat tcagagaaga aaccaattgt ccatattgca tcagacattg   1080
ccgtcactgc gtctttract ggctcttctc gctaaccaaa ccggtaaccc cgcttattaa   1140
aagcattctg taacaaagcg ggaccaaagc catgacaaaa acgcgtaaca aaagtgtcta   1200
taatcacggc agaaaagtcc acattgatta tttgcacggc gtcacacttt gctatgccat   1260
agcattttta tccataagat tagcggatcc tacctgacgc tttttatcgc aactctctac   1320
tgtttctcca tacccgtttt tttgggctag cgaattctga gaacaaacta aatggataaa   1380
tttcgtgttc aggggccaac gaagctccag ggcgaagtca caatttccgg cgctaaaaat   1440
gctgctctgc ctatcctttt tgccgcacta ctggcggaag aaccggtaga gatccagaac   1500
gtcccgaaac tgaaagacgt cgatacatca atgaagctgc taagccagct gggtgcgaaa   1560
gtagaacgta atggttctgt gcatattgat gcccgcgacg ttaatgtatt ctgcgcacct   1620
tacgatctgg ttaaaaccat gcgtgcttct atctgggcgc tggggccgct ggtagcgcgc   1680
tttggtcagg ggcaagtttc actacctggc ggttgtacga tcggtgcgcg tccggttgat   1740
ctacacattt ctggcctcga acaattaggc gcgaccatca aactggaaga aggttacgtt   1800
aaagcttccg tcgatggtcg tttgaaaggt gcacatatcg tgatggataa agtcagcgtt   1860
ggcgcaacgg tgaccatcat gtgtgctgca accctggcgg aaggcaccac gattattgaa   1920
aacgcagcgc gtgaaccgga aatcgtcgat accgcgaact tcctgattac gctgggtgcg   1980
aaaattagcg gtcagggcac cgatcgtatc gtcatcgaag gtgtggaacg tttaggcggc   2040
ggtgtctatc gcgttctgcc ggatcgtatc gaaaccggta cttttcctggt ggcggcggcg   2100 atttctcgcg gcaaaattat ctgccgtaac gcgcagccag atactctcga cgccgtgctg   2160
gcgaaactgc gtgacgctgg agcggacatc gaagtcggcg aagactggat tagcctggat   2220
atgcatggca aacgtccgaa ggctgttaac gtacgtaccg cgccgcatcc ggcattcccg   2280
accgatatgc aggcccagtt cacgctgttg aacctggtgg cagaagggac cgggtttatc   2340
accgaaacgg tctttgaaaa ccgctttatg catgtgccag agctgagccg tatgggcgcg   2400
cacgccgaaa tcgaaagcaa taccgttatt tgtcacggtg ttgaaaaact ttctggcgca   2460
caggttatgg caaccgatct gcgtgcatca gcaagcctgg tgctggctgg ctgtattgcg   2520
gaagggacga cggtggttga tcgtatttat cacatcgatc gtggctacga acgcattgaa   2580
gacaaactgc gcgctttagg tgcaaatatt gagcgtgtga aaggcgaata agaattcagg   2640
aaaaaaacgc tgtgaaaaat gttggtttta tcggctggcg cggaatggtc ggctctgttc   2700
tcatgcaacg catggtagag gagcgcgatt tcgacgctat tcgccctgtt ttcttttcta   2760
cctcccagtt tggacaggcg gcgcccacct tcggcgacac ctccaccggc acgctacagg   2820
acgcttttga tctggatgcg ctaaaagcgc tcgatatcat cgtgacctgc cagggcggcg   2880
attataccaa cgaaatttat ccaaagctgc gcgaaagcgg atggcagggt tactggattg   2940
atgcggcttc tacgctgcgc atgaaagatg atgccattat tattctcgac ccggtcaacc   3000
aggacgtgat taccgacggc ctgaacaatg gcgtgaagac ctttgtgggc ggtaactgta   3060
ccgttagcct gatgttgatg tcgctggcg gtctctttgc ccataatctc gttgactggg   3120
tatccgtcgc gacctatcag gccgcctccg gcggcggcgc gccatatg cgcgagctgt   3180 taacccgagat gggtcagttg tatggccatg tcgccgatga actggcgacg ccgtcttccg   3240
caattcttga tattgaacgc aaagttacgg cattgacccg cagcggcgag ctgccggttg   3300
ataactttgg cgtaccgctg gcgggaagcc tgatcccctg gatcgacaaa cagctcgata   3360
```

-continued

```
acggccagag ccgcgaagag tggaaaggcc aggcggaaac caacaagatt ctcaatactg    3420
cctctgtgat tccggttgat ggtttgtgtg tgcgcgtcgg cgcgctgcgc tgtcacagcc    3480
aggcgttcac catcaagctg aaaaagagg tatccattcc gacggtggaa gaactgctgg    3540
cggcacataa tccgtgggcg aaagtggtgc cgaacgatcg tgatatcact atgcgcgaat    3600
taaccccggc ggcggtgacc ggcacgttga ctacgccggt tggtcgtctg cgtaagctga    3660
acatggggcc agagttcttg tcggcgttta ccgtaggcga ccagttgtta tggggcgccg    3720
ccgagccgct gcgtcgaatg ctgcgccagt tggcgtagtc tagctgcacg ataccgtcga    3780
cttgtacata gactcgctcc gaaattaaag aacacttaaa ttatctacta aaggaatctt    3840
tagtcaagtt tatttaagat gacttaacta tgaatacaca attgatgggt gagcgtagga    3900
gcatgcttat gcgaaaggcc atcctgacgg atggcctttt tggatcttcc ggaagacctt    3960
ccattctgaa atgagctgtt gacaattaat catccggctc gtataatgtg tggaattgtg    4020
agcggataac aatttcacac aggaaacaga ccatgggcat cgtacccgaa gcttttttgt    4080
tgttctcccg tcgcgctgat atccggcgga ttagccttga aacgaacaat aacaatgttg    4140
ctattcccct tacaggcgtc aaagaagcct cggctttgga ttttgatgtt actgataacc    4200
gcatctactg gaccgacatt agcttaaaga caatcagccg ggcgtttatg aacgggtcag    4260
ccttggaaca cgtcgttgaa ttcggcctgg actacccgga gggtatggct gtcgactggc    4320
ttggcaagaa tttatactgg gcagatacag gcaccaatcg catcgaagtt caaagttgg    4380 atggacaaca tcgccaagtt ttggtctgga aggacttgga cagccctcgg gccttagcac    4440
tggacccggc cgagggtttt atgtattgga cagagtgggg cggaaaccct aaaatcgatc    4500
gggcagctat ggacggctcg gaacgcacga ctttagttcc gaatgtaggg cgtgccaatg    4560
gattgacgat tgactatgct aagcgccgcc tttattggac agacctggac actaacctta    4620
tcgagtcatc taacatgctt ggcttgaatc gtgaggtaat cgccgatgat ttaccacacc    4680
ccttcggcct gacgcagtac caagattaca tctattggac tgactggtct cggcggagca    4740
ttgaacgggc caataaaacg tcagggcaga atcgtactat cattcaaggg cacttagatt    4800
acgtcatgga tatcttagtt tttcactcca gtcggcaatc aggttggaac gagtgtgcgt    4860
caagtaacgg acactgcagt catttgtgtt tggcagtccc tgtgggcggt ttcgtttgcg    4920
ggtgcccagc ccactactct ttgaacgcag acaatcgcac gtgctcggcg ccaaccacgt    4980
tcctgttgtt tagtcaaaaa tcggctatta atcgtatggt cattgacgag caacaatccc    5040
ccgacatcat ccttccaatc cactcacttc ggaacgtccg tgccatcgat tacgacccct    5100
tagataaaca gctttactgg atcgattctc ggcagaacat gatccggaaa gcgcaggagg    5160
acgggtcgca aggttttaca gtagtagtat cgtctgtacc ctcacagaat cttgagattc    5220
agccatacga tctgagtatt gatatctatt cgcgttacat ttattggacc tgcgaggcca    5280
ctaatgtaat taacgtgacg cgcctggatg gccgctccgt tggtgtggta ctgaagggag    5340
aacaggatcg tcctcgggct atcgtggtga accccgaaaa aggatatatg tacttcacca    5400
acctgcagga acgtagcccg aaaatcgaac gggcggccct tgatggcaca gaacgggaag    5460
tcttgttttt ctcgggtctt tctaagccaa ttgcgctggc attggacagc cggctgggta    5520
agttattctg ggccgattcg gacctgcgtc gtatcgagag ttctgacctt tcgggagcaa    5580
accgtatcgt attagaggac agtaacattc tgcaaccggt cgggcttaca gtcttcgaaa    5640
attggttgta ttggatcgat aaacagcaac agatgatcga aaaaattgac atgacggggc    5700
gcgagggtcg gacgaaggtc caagcgcgga tcgctcaatt gagcgacatc catgctgtaa    5760
```

```
aagaattgaa cttacaggag taccgccagc atccatgtgc acaggataac ggaggatgta    5820
gccacatttg cctggtcaag ggtgatggca caacgcgctg ttcgtgtcct atgcatcttg    5880
tattactgca agacgagttg tcatgctaat agcccgggga tccgtcgacc tgcagccaag    5940
ctcccaagct tggctgtttt ggcggatgag agaagatttt cagcctgata cagattaaat    6000
cagaacgcag aagcggtctg ataaaacaga atttgcctgg cggcagtagc gcggtggtcc    6060
cacctgaccc catgccgaac tcagaagtga acgccgtag cgccgatggt agtgtggggt    6120
ctccccatgc gagagtaggg aactgccagg catcaaataa aacgaaaggc tcagtcgaaa    6180
gactgggcct ttcgttttat ctgttgtttg tcggtgaacg ctctcctgag taggacaaat    6240
ccgccgggag cggatttgaa cgttgcgaag caacggcccg gagggtggcg gcaggacgc    6300 ccgccataaa ctgccaggca tcaaattaag cagaaggcca tcctgacgga tggcctttt    6360 gcgtttctac aaactctttt gtttattttt ctaaatacat tcaaatatgt atccgctcat    6420
gagacaataa ccctgataaa tgcttcaata atggaagatc ttccaacatc acaggtaaac    6480
agaaacgtcg ggtcgatcgg gaaattcttt cccggacggc gcggggttgg gcaagccgca    6540
ggcgcgtcag tgcttttagc gggtgtcggg gcgcagccat gacccagtca cgtagcgata    6600
gcggagtgta tactggctta actatgcggc atcagacag attgtactga gagtgcacca    6660
tatgcggtgt gaaataccgc acagatgcgt aaggagaaaa taccgcatca ggcgctcttc    6720
cgcttcctcg ctcactgact cgctgcgctc ggtcgttcgg ctgcggcgag cggtatcagc    6780
tcactcaaag gcggtaatac ggttatccac agaatcaggg gataacgcag gaaagaacat    6840
gtgagcaaaa ggccagcaaa aggccaggaa ccgtaaaaag gccgcgttgc tggcgttttt    6900
ccataggctc cgccccctg acgagcatca aaaaatcga cgctcaagtc agaggtggcg    6960
aaacccgaca ggactataaa gataccaggc gtttccccct ggaagctccc tcgtgcgctc    7020
tcctgttccg accctgccgc ttaccggata cctgtccgcc tttctccctt cgggaagcgt    7080
ggcgctttct catagctcac gctgtaggta tctcagttcg gtgtaggtcg ttcgctccaa    7140
gctgggctgt gtgcacgaac cccccgttca gcccgaccgc tgcgccttat ccggtaacta    7200
tcgtcttgag tccaacccgg taagacacga cttatcgcca ctggcagcag ccactggtaa    7260
caggattagc agagcgaggt atgtaggcgg tgctacagag ttcttgaagt ggtggcctaa    7320
ctacggctac actagaagga cagtatttgg tatctgcgct ctgctgaagc cagttacctt    7380
cggaaaaaga gttggtagct cttgatccgg caaacaaacc accgctggta gcggtggttt    7440
ttttgtttgc aagcagcaga ttacgcgcag aaaaaaagga tctcaagaag atcctttgat    7500
cttttctacg gggtctgacg ctcagtggaa cgaaaactca cgttaaggga ttttggtcat    7560
gagattatca aaaaggatct tcacctagat ccttttaaat taaaaatgaa gttttaaatc    7620
aatctaaagt atatatgagt aaacttggtc tgacagtcta ga                      7662
```

<210> SEQ ID NO 4
<211> LENGTH: 8816
<212> TYPE: DNA
<213> ORGANISM: Artificial Sequence
<220> FEATURE:
<223> OTHER INFORMATION: Synthetic- plasmid pK-DLRP6 (pYA4545 encoding
      human Wnt binding domains of LRP6)

<400> SEQUENCE: 4

```
gactcttcgc gatgtacggg ccagatatac gcgttaactg cagtctagat tatgcgaaag      60
gccatcctga cggatggcct ttttgtttaa acggatccgc gacattgatt attgactagt     120
```

```
tattaatagt aatcaattac ggggtcatta ggggactttc cggggacttt cctccccacg    180
cgggggactt tccgccacgg gcggggactt ccggggact  ttccgttcat agcccatata    240
tggagttccg cgttacataa cttacggtaa atggcccgcc tggctgaccg cccaacgacc    300
cccgcccatt gacgtcaata atgacgtatg ttcccatagt aacgccaata gggactttcc    360
attgacgtca atgggtggac tatttacggt aaactgccca cttggcagta catcaagtgt    420
atcatatgcc aagtacgccc cctattgacg tcaatgacgg taaatggccc gcctggcatt    480
atgcccagta catgacctta tgggactttc ctacttggca gtacatctac gtattagtca    540
tcgctattac catggtgatg cggttttggc agtacatcaa tgggcgtgga tagcggtttg    600
actcacgggg atttccaagt ctccacccca ttgacgtcaa tgggagtttg ttttggcacc    660
aaaatcaacg ggactttcca aaatgtcgta acaactccgc cccattgacg caaatgggcg    720
gtaggcgtgt acggtgggag gtctatataa gcagagctct ctggctaact agagaaccca    780
ctgcttactg gcttatcgaa attaatacga ctcactatag ggagacccaa gctggctagc    840
gtttaaactt aagcttggta ccaccatggg cattgtccca gaggctttcc ttttgttttc    900
acggagagca gatatcagac gaatttctct ggaaacaaac aataataatg tggctattcc    960
actcactggt gtcaaagaag cttctgcttt ggattttgat gtgacagaca accgaattta    1020
ttggactgat atatcactca agaccatcag cagagccttt atgaatggca gtgcactgga    1080
acatgtggta gaattcggct tagattatcc agaaggcatg gcagtagact ggcttgggaa    1140
gaacttgtac tgggcagaca caggaacgaa tcgaattgag gtgtcaaagt tggatgggca    1200
gcaccgacaa gttttggtgt ggaaagacct agatagtccc agagctctcg cgttggaccc    1260
tgccgaagga tttatgtatt ggactgaatg gggtggaaaa cctaagatag acagagctgc    1320
aatggatgga agtgaacgta ctaccttagt tccaaatgtg gggcgggcaa acggcctaac    1380
tattgattat gctaaaagga ggctttattg gacagacctg gacaccaact aatagaatc     1440 ttcaaatatg cttgggctca accgtgaagt tatagcagat gacttgcctc atccttttgg    1500
cttaactcag taccaagatt atatctactg gacggactgg agccgacgca gcattgagcg    1560
tgccaacaaa accagtggcc aaaaccgcac catcattcag ggccatttgg attatgtgat    1620
ggacatcctc gtctttcact catctcgaca gtcagggtgg aatgaatgtg cttccagcaa    1680
tgggcactgc tcccacctct gcttggctgt gccagttggg ggttttgttt gtggatgccc    1740
tgcccactac tctcttaatg ctgacaacag gacttgtagt gctcctacga cttttcctgct   1800 cttcagtcaa aagagtgcca tcaaccgcat ggtgattgat gaacaacaga gccccgacat    1860
catccttccc atccacagcc ttcggaatgt ccgggccatt gactatgacc cactggacaa    1920
gcaactctat tggattgact cacgacaaaa catgatccga aaggcacaag aagatggcag    1980
ccagggcttt actgtggttg tgagctcagt tccgagtcag aacctggaaa tacaacccta    2040
tgacctcagc attgatattt acagccgcta catctactgg acttgtgagg ctaccaatgt    2100
cattaatgtg acaagattag atgggagatc agttggagtg gtgctgaaag gcgagcagga    2160
cagacctcga gccattgtgg taaacccaga gaaagggtat atgtatttta ccaatcttca    2220
ggaaaggtct cctaaaattg aacgggctgc tttggatggg acagaacggg aggtcctctt    2280
tttcagtggc ttaagtaaac caattgcttt agcccttgat agcaggctgg gcaagctctt    2340
ttgggctgat tcagatctcc ggcgaattga aagcagtgat ctctcaggtg ctaaccggat    2400
agtattagaa gactccaata tcttgcagcc tgtgggactt actgtgtttg aaaactggct    2460
ctattggatt gataaacagc agcaaatgat tgaaaaaatt gacatgacag gtcgagaggg    2520
```

```
tagaaccaaa gtccaagctc gaattgccca gcttagtgac attcatgcag taaaggagct   2580
gaaccttcaa gaatacagac agcacccttg tgctcaggat aatggtggct gttcacatat   2640
ttgtcttgta aaggggatg gtactacaag gtgttcttgc cccatgcacc tggttctact   2700
tcaagatgag ctatcatgtt aatagctcga gaatgcttcg agcagacatg ataagataca   2760
ttgatgagtt tggacaaacc acaactagaa tgcagtgaaa aaaatgcttt atttgtgaaa   2820
tttgtgatgc tattgcttta tttgtaacca ttataagctg caataaacaa gttaacaaca   2880
acaattgcat tcattttatg tttcaggttc agggggagat gtgggaggtt ttttaaagca   2940
agtaaaacct ctacaaatgt ggtaaaatcc gataaggatc gatccggggc atgcaaccag   3000
ctgtggaatg tgtgtcagtt agggtgtgga aagtccccag gctccccagc aggcagaagt   3060
atgcaaagca tgtggggatg cggtgggctc tatggcttct actgggcggt tttatggaca   3120
gcaagcgaac cggaattgcc agctggggcg ccctctggta aggttgggaa gccctgcaaa   3180
gtaaactgga tggctttctc gccgccaagg atctgtcgac ccctagattt cagtgcaatt   3240
tatctcttca aatgtagcac ctgaagtcag ccccatacga tataagttgt tggaagatct   3300
agcccgccta atgagcgggc ttttttttaa ttcgcaattc cccgatgcat aatgtgcctg   3360
tcaaatggac gaagcaggga ttctgcaaac cctatgctac tccgtcaagc cgtcaattgt   3420
ctgattcgtt accaattatg acaacttgac ggctacatca ttcactttt cttcacaacc   3480 ggcacgaaac tcgctcgggc tggccccggt gcattttta aatactgcgc agaaatagag   3540
ttgatcgtca aaaccaacat tgcgaccgac ggtggcgata ggcatccggg tagtgctcaa   3600
aagcagcttc gcctgactaa tgcgttggtc ctcgcgccag cttaagacgc taatccctaa   3660
ctgctggcgg aaaagatgtg acagacgcga cggcgacaag caaacatgct gtgcgacgct   3720
ggcgatatca aaattgctgt ctgccaggtg atcgctgatg tactgacaag cctcgcgtac   3780
ccgattatcc atcggtggat ggagcgactc gttaatcgct tccatgcgcc gcagtaacaa   3840
ttgctcaagc agatttatcg ccagcagctc cgaatagcgc ccttccccct gcccggcgtt   3900
aatgatttgc ccaaacaggt cgctgaaatg cggctggtgc gcttcatccg gcgaaagaa   3960 acccgtattg gcaaatattg acggccagtt aagccattca tgccagtagg cgcgcggacg   4020
aaagtaaacc cactggtgat accattcgcg agcctccgga tgacgaccgt agtgatgaat   4080
ctctcctggc gggaacagca aaatatcacc cggtcggcag acaaattctc gtccctgatt   4140
tttcaccacc ccctgaccgc gaatggtgag attgagaata taaccttca ttcccagcgg   4200 tcggtcgata aaaaaatcga gataaccgtt ggcctcaatc ggcgttaaac ccgccaccag   4260
atgggcgtta acgagtatc ccggcagcag gggatcattt tgcgcttcag ccatacttt   4320 catactccca ccattcagag aagaaaccaa ttgtccatat tgcatcagac attgccgtca   4380
ctgcgtcttt tactggctct tctcgctaac ccaaccggta accccgctta ttaaaagcat   4440
tctgtaacaa agcgggacca aagccatgac aaaaacgcgt aacaaaagtg tctataatca   4500
cggcagaaaa gtccacattg attatttgca cggcgtcaca ctttgctatg ccatagcatt   4560
tttatccata agattagcgg atcctacctg acgcttttta tcgcaactct ctactgtttc   4620
tccatacccg ttttttggg ctagcgaatt ctgagaacaa actaagtgga taaatttcgt   4680
gttcaggggc caacgaagct ccaggcgaa gtcacaattt ccggcgctaa aaatgctgct   4740
ctgcctatcc ttttgccgc actactggcg gaagaaccgg tagagatcca gaacgtcccg   4800
aaactgaaag acgtcgatac atcaatgaag ctgctaagcc agctgggtgc gaaagtagaa   4860
cgtaatggtt ctgtgcatat tgatgcccgc gacgttaatg tattctgcgc accttacgat   4920
```

-continued

```
ctggttaaaa ccatgcgtgc ttctatctgg gcgctggggc cgctggtagc gcgctttggt    4980 cagggggcaag tttcactacc tggcggttgt acgatcggtg cgcgtccggt tgatctacac    5040
atttctggcc tcgaacaatt aggcgcgacc atcaaactgg aagaaggtta cgttaaagct    5100
tccgtcgatg tcgtttgaa aggtgcacat atcgtgatgg ataaagtcag cgttggcgca    5160
acggtgacca tcatgtgtgc tgcaaccctg gcggaaggca ccacgattat tgaaaacgca    5220
gcgcgtgaac cggaaatcgt cgataccgcg aacttcctga ttacgctggg tgcgaaaatt    5280
agcggtcagg gcaccgatcg tatcgtcatc gaaggtgtgg aacgtttagg cggcggtgtc    5340
tatcgcgttc tgccggatcg tatcgaaacc ggtactttcc tggtggcggc ggcgatttct    5400
cgcggcaaaa ttatctgccg taacgcgcag ccagatactc tcgacgccgt gctggcgaaa    5460
ctgcgtgacg ctggagcgga catcgaagtc ggcgaagact ggattagcct ggatatgcat    5520
ggcaaacgtc cgaaggctgt taacgtacgt accgcgccgc atccggcatt cccgaccgat    5580
atgcaggccc agttcacgct gttgaacctg gtggcagaag ggaccgggtt tatcaccgaa    5640
acggtctttg aaaaccgctt tatgcatgtg ccagagctga ccgtatgggg cgcgcacgcc    5700
gaaatcgaaa gcaataccgt tatttgtcac ggtgttgaaa aactttctgg cgcacaggtt    5760
atggcaaccg atctgcgtgc atcagcaagc ctggtgctgg ctggctgtat tgcggaaggg    5820
acgacggtgg ttgatcgtat ttatcacatc gatcgtggct acgaacgcat tgaagacaaa    5880
ctgcgcgctt taggtgcaaa tattgagcgt gtgaaaggcg aataagaatt caggaaaaaa    5940
acgctgtgaa aaatgttggt tttatcggct ggcgcggaat ggtcggctct gttctcatgc    6000
aacgcatggt agaggagcgc gatttcgacg ctattcgccc tgttttcttt tctacctccc    6060
agtttggaca ggcggcgccc accttcggcg acacctccac cggcacgcta caggacgctt    6120
ttgatctgga tgcgctaaaa gcgctcgata tcatcgtgac ctgccagggc ggcgattata    6180
ccaacgaaat ttatccaaag ctgcgcgaaa gcggatggca gggttactgg attgatgcgg    6240
cttctacgct gcgcatgaaa gatgatgcca ttattattct cgacccggtc aaccaggacg    6300
tgattaccga cggcctgaac aatggcgtga agacctttgt gggcggtaac tgtaccgtta    6360
gcctgatgtt gatgtcgctg gcggtctct ttgcccataa tctcgttgac tgggtatccg    6420
tcgcgaccta tcaggccgcc tccggcggcg gcgcgcgcca tatgcgcgag ctgttaaccc    6480
agatgggtca gttgtatggc catgtcgccg atgaactggc gacgccgtct ccgcaattc    6540 ttgatattga acgcaaagtt acggcattga cccgcagcgg cgagctgccg gttgataact    6600
ttggcgtacc gctggcggga agcctgatcc cctggatcga caacagctc gataacggcc    6660 agagccgcga agagtggaaa ggccaggcgg aaaccaacaa gattctcaat actgcctctg    6720
tgattccggt tgatggtttg tgtgtgcgcg tcggcgcgct gcgctgtcac agccaggcgt    6780
tcaccatcaa gctgaaaaaa gaggtatcca ttccgacggt ggaagaactg ctggcggcac    6840
ataatccgtg ggcgaaagtg gtgccgaacg atcgtgatat cactatgcgc gaattaaccc    6900
cggcggcggt gaccggcacg ttgactacgc cggttggtcg tctgcgtaag ctgaacatgg    6960
ggccagagtt cttgtcggcg tttaccgtag gcgaccagtt gttatggggc gccgccgagc    7020
cgctgcgtcg aatgctgcgc cagttggcgt agtctagctg cacgataccg tcgacttgta    7080
catagactcg ctccgaaatt aaagaacact taaattatct actaaaggaa tctttagtca    7140
agtttattta agatgactta actatgaata cacaattgat gggtgagcgt aggatcttcc    7200
attattgaag catttatcag ggttattgtc tcatgagctt ggctgttttg gcggatgaga    7260
gaagattttc agcctgatac agattaaatc agaacgcaga agcggtctga taaaacagtt    7320
```

```
tgcctggcgg cagtagcgcg gtggtcccac ctgaccccat gccgaactca gaagtgaaac    7380
gccgtagcgc cgatggtagt gtggggtctc cccatgcgag agtagggaac tgccaggcat    7440
caaataaaac gaaaggctca gtcgaaagac tgggcctttc gttttatctg ttgtttgtcg    7500
gtgaacgctc tcctgagtag gacaaatccg ccgggagcgg atttgaacgt tgcgaagcaa    7560
cggcccggag ggtggcgggc aggacgcccg ccataaactg ccaggcatca aattaagcag    7620
aaggccatcc tgacggatgg cctttttgcg tttctacaaa ctcttttgt ttatttttct     7680 aaatacattc aaatatgtat ccgctcatga caataaccc ctgataaatg cttcaataat     7740
ggaagatctt ccaacatcac aggtaaacag aaacgtcggg tcgatcggga aattctttcc    7800
cggacggcgc ggggttgggc aagccgcagg cgcgtcagtg cttttagcgg gtgtcggggc    7860
agccctgaac cagtcacggg atcgatctgt gcggtatttc acaccgcata caggtggcac    7920
ttttcgggga atgtgcgcg gaaccccct ttgtttattt ttctaaatac attcaaatat       7980
gtatccgctc atgagacaat aaccctgata aatgcttcaa taatagcacg tgctaaaact    8040
tcatttttaa tttaaaagga tctaggtgaa gatcctttt gataatctca tgaccaaaat     8100
cccttaacgt gagttttcgt tccactgagc gtcagacccc gtagaaaaga tcaaaggatc    8160
ttcttgagat cctttttttc tgcgcgtaat ctgctgcttg caaacaaaaa aaccaccgct    8220
accagcggtg gtttgtttgc cggatcaaga gctaccaact ctttttccga aggtaactgg    8280
cttcagcaga gcgcagatac caaatactgt ccttctagtg tagccgtagt taggccacca    8340
cttcaagaac tctgtagcac cgcctacata cctcgctctg ctaatcctgt taccagtggc    8400
tgctgccagt ggcgataagt cgtgtcttac cgggttggac tcaagacgat agttaccgga    8460
taaggcgcag cggtcgggct gaacgggggg ttcgtgcaca cagcccagct tggagcgaac    8520
gacctacacc gaactgagat acctacagcg tgagctatga gaaagcgcca cgcttcccga    8580
agggagaaag gcggacaggt atccggtaag cggcagggtc ggaacaggag agcgcacgag    8640
ggagcttcca gggggaaacg cctggtatct ttatagtcct gtcgggtttc gccacctctg    8700
acttgagcgt cgatttttgt gatgctcgtc aggggggcgg agcctatgga aaaacgccag    8760
caacgcggcc ttttacggtt cctgggctt ttgctggcct tttgctcaca tgttct         8816
```

<210> SEQ ID NO 5
<211> LENGTH: 6222
<212> TYPE: DNA
<213> ORGANISM: Artificial Sequence
<220> FEATURE:
<223> OTHER INFORMATION: Synthetic- plasmid pK-PD-1 (pYA3681 encoding extracellular domain of human PD-1)

<400> SEQUENCE: 5

```
agatctagcc cgcctaatga gcgggctttt ttttaattcg caattccccg atgcataatg      60
tgcctgtcaa atggacgaag cagggattct gcaaacccta tgctactccg tcaagccgtc    120
aattgtctga ttcgttacca attatgacaa cttgacggct acatcattca ctttttcttc    180
acaaccggca cggaactcgc tcgggctggc cccggtgcat ttttttaaata cccgcgagaa    240 atagagttga tcgtcaaaac caacattgcg accgacggtg gcgataggca tccgggtggt    300
gctcaaaagc agcttcgcct ggctgatacg ttggtcctcg cgccagctta agacgctaat    360
ccctaactgc tggcggaaaa gatgtgacag acgcgacggc gacaagcaaa catgctgtgc    420
gacgctggcg atatcaaaat tgctgtctgc caggtgatcg ctgatgtact gacaagcctc    480
gcgtacccga ttatccatcg gtggatggag cgactcgtta atcgcttcca tgcgccgcag    540
```

```
taacaattgc tcaagcagat ttatcgccag cagctccgaa tagcgccctt cccottgccc    600
ggcgttaatg atttgcccaa acaggtcgct gaaatgcggc tggtgcgctt catccgggcg    660
aaagaacccc gtattggcaa atattgacgg ccagttaagc cattcatgcc agtaggcgcg    720
cggacgaaag taaacccact ggtgatacca ttcgcgagcc tccggatgac gaccgtagtg    780
atgaatctct cctggcggga acagcaaaat atcacccggt cggcaaacaa attctcgtcc    840
ctgattttc accacccct gaccgcgaat ggtgagattg agaatataac ctttcattcc      900
cagcggtcgg tcgataaaaa aatcgagata accgttggcc tcaatcggcg ttaaacccgc    960
caccagatgg gcattaaacg agtatcccgg cagcagggga tcattttgcg cttcagccat   1020
acttttcata ctcccgccat tcagagaaga aaccaattgt ccatattgca tcagacattg   1080
ccgtcactgc gtctttact ggctcttctc gctaaccaaa ccgtaaccc cgcttattaa     1140
aagcattctg taacaaagcg ggaccaaagc catgacaaaa acgcgtaaca aaagtgtcta   1200
taatcacggc agaaaagtcc acattgatta tttgcacggc gtcacacttt gctatgccat   1260
agcatttta tccataagat tagcggatcc tacctgacgc ttttatcgc aactctctac     1320
tgtttctcca tacccgtttt tttgggctag cgaattctga gaacaaacta aatggataaa   1380
tttcgtgttc aggggccaac gaagctccag ggcgaagtca caattccgg cgctaaaaat    1440
gctgctctgc ctatcctttt tgccgcacta ctggcggaag aaccggtaga gatccagaac   1500
gtcccgaaac tgaaagacgt cgatacatca atgaagctgc taagccagct gggtgcgaaa   1560
gtagaacgta atggttctgt gcatattgat gcccgcgacg ttaatgtatt ctgcgcacct   1620
tacgatctgg ttaaaaccat gcgtgcttct atctgggcgc tggggccgct ggtagcgcgc   1680
tttggtcagg ggcaagtttc actacctggc ggttgtacga tcggtgcgcg tccggttgat   1740
ctacacattt ctggcctcga acaattaggc gcgaccatca aactggaaga aggttacgtt   1800
aaagcttccg tcgatggtcg tttgaaaggt gcacatatcg tgatggataa agtcagcgtt   1860
ggcgcaacgg tgaccatcat gtgtgctgca accctggcgg aaggcaccac gattattgaa   1920
aacgcagcgc gtgaaccgga atcgtcgat accgcgaact tcctgattac gctgggtgcg    1980
aaaattagcg gtcagggcac cgatcgtatc gtcatcgaag gtgtggaacg tttaggcggc   2040
ggtgtctatc gcgttctgcc ggatcgtatc gaaaccggta cttttcctggt ggcggcggcg  2100
atttctcgcg gcaaaattat ctgccgtaac gcgcagccag atactctcga cgccgtgctg   2160
gcgaaactgc gtgacgctgg agcggacatc gaagtcggcg aagactggat tagcctggat   2220
atgcatggca acgtccgaa ggctgttaac gtacgtaccg cgccgcatcc ggcattcccg    2280
accgatatgc aggcccagtt cacgctgttg aacctggtgg cagaagggac cgggtttatc   2340
accgaaacgg tctttgaaaa ccgctttatg catgtgccag agctgagccg tatgggcgcg   2400
cacgccgaaa tcgaaagcaa taccgttatt tgtcacggtg ttgaaaaact ttctggcgca   2460
caggttatgg caaccgatct gcgtgcatca gcaagcctgg tgctggctgg ctgtattgcg   2520
gaagggacga cggtggttga tcgtatttat cacatcgatc gtggctacga acgcattgaa   2580
gacaaactgc gcgctttagg tgcaaatatt gagcgtgtga aaggcgaata agaattcagg   2640
aaaaaaacgc tgtgaaaaat gttggttta tcggctggcg cggaatggtc ggctctgttc    2700
tcatgcaacg catggtagag gagcgcgatt tcgacgctat tcgccctgtt ttcttttcta   2760
cctcccagtt tggacaggcg gcgcccacct tcggcgacac ctccaccggc acgctacagg   2820
acgcttttga tctggatgcg ctaaaagcgc tcgatatcat cgtgacctgc cagggcggcg   2880
attataccaa cgaaattat ccaaagctgc gcgaaagcgg atggcagggt tactggattg    2940
```

```
atgcggcttc tacgctgcgc atgaaagatg atgccattat tattctcgac ccggtcaacc    3000
aggacgtgat taccgacggc ctgaacaatg gcgtgaagac ctttgtgggc ggtaactgta    3060
ccgttagcct gatgttgatg tcgctgggcg gtctctttgc ccataatctc gttgactggg    3120
tatccgtcgc gacctatcag gccgcctccg cggcggcgc gcgccatatg cgcgagctgt     3180
taacccagat gggtcagttg tatggccatg tcgccgatga actggcgacg ccgtcttccg    3240
caattcttga tattgaacgc aaagttacgg cattgacccg cagcggcgag ctgccggttg    3300
ataactttgg cgtaccgctg gcgggaagcc tgatcccctg gatcgacaaa cagctcgata    3360
acggccagag ccgcgaagag tggaaaggcc aggcggaaac caacaagatt ctcaatactg    3420
cctctgtgat tccggttgat ggtttgtgtg tgcgcgtcgg cgcgctgcgc tgtcacagcc    3480
aggcgttcac catcaagctg aaaaaagagg tatccattcc gacggtggaa gaactgctgg    3540
cggcacataa tccgtgggcg aaagtggtgc cgaacgatcg tgatatcact atgcgcgaat    3600
taaccccggc ggcggtgacc ggcacgttga ctacgccggt tggtcgtctg cgtaagctga    3660
acatggggcc agagttcttg tcggcgttta ccgtaggcga ccagttgtta tggggcgccg    3720
ccgagccgct gcgtcgaatg ctgcgccagt tggcgtagtc tagctgcacg ataccgtcga    3780
cttgtacata gactcgctcc gaaattaaag aacacttaaa ttatctacta aaggaatctt    3840
tagtcaagtt tatttaagat gacttaacta tgaatacaca attgatgggt gagcgtagga    3900
gcatgcttat gcgaaaggcc atcctgacgg atggcctttt tggatcttcc ggaagaccTT    3960
ccattctgaa atgagctgtt gacaattaat catccggctc gtataatgtg tggaattgtg    4020
agcggataac aatttcacac aggaaacaga ccatgggctt agactcccca gacaggcCCT    4080
ggaaccCCCC caccttctcc ccagccctgc tcgtggtgac cgaaggggac aacgccaccT    4140
tcacctgcag cttctccaac acatcggaga gcttcgtgct aaactggtac cgcatgagcc    4200
ccagcaacca gacggacaag ctggccgcct cccccgagga ccgcagccag cccggccagg    4260
actgccgctt ccgtgtcaca caactgccca acggcgtga cttccacatg agcgtggtca    4320
gggcccggcg caatgacagc ggcacctacc tctgtgggc catctccctg gcccccaagg    4380
cgcagatcaa agagagcctg cgggcagagc tcagggtgac agagagaagg cagaagtgc     4440 ccacagccca ccccagcccc tcaccctaat agcccgggga tccgtcgacc tgcagccaag    4500
ctcccaagct tggctgtttt ggcggatgag agaagatttt cagcctgata cagattaaat    4560
cagaacgcag aagcggtctg ataaaacaga atttgcctgg cggcagtagc gcggtggtcc    4620
cacctgaccc catgccgaac tcagaagtga acgccgtag cgccgatggt agtgtggggT     4680
ctccccatgc gagagtaggg aactgccagg catcaaataa aacgaaaggc tcagtcgaaa    4740
gactgggcct ttcgttttat ctgttgtttg tcggtgaacg ctctcctgag taggacaaat    4800
ccgccgggag cggatttgaa cgttgcgaag caacggcccg gagggtggcg gcaggacgc     4860 ccgccataaa ctgccaggca tcaaattaag cagaaggcca tcctgacgga tggccttttt    4920
gcgtttctac aaactctttt gtttattttt ctaaatacat tcaaatatgt atccgctcat    4980
gagacaataa ccctgataaa tgcttcaata atggaagatc ttccaacatc acaggtaaac    5040
agaaacgtcg ggtcgatcgg gaattctttt cccggacggc gcggggttgg caagccgca     5100 ggcgcgtcag tgcttttagc gggtgtcggg gcgcagccat gacccagtca cgtagcgata    5160
gcggagtgta tactggctta actatgcggc atcagagcag attgtactga gagtgcacca    5220
tatgcggtgt gaaataccgc acagatgcgt aaggagaaaa taccgcatca ggcgctcttc    5280
cgcttcctcg ctcactgact cgctgcgctc ggtcgttcgg ctgcggcgag cggtatcagc    5340
```

| | | | | |
|---|---|---|---|---|
| tcactcaaag | gcggtaatac | ggttatccac | agaatcaggg | gataacgcag gaaagaacat | 5400 |
| gtgagcaaaa | ggccagcaaa | aggccaggaa | ccgtaaaaag | gccgcgttgc tggcgttttt | 5460 |
| ccataggctc | cgcccccctg | acgagcatca | aaaaatcga | cgctcaagtc agaggtggcg | 5520 |
| aaacccgaca | ggactataaa | gataccaggc | gtttccccct | ggaagctccc tcgtgcgctc | 5580 |
| tcctgttccg | accctgccgc | ttaccggata | cctgtccgcc | tttctccctt cgggaagcgt | 5640 |
| ggcgctttct | catagctcac | gctgtaggta | tctcagttcg | gtgtaggtcg ttcgctccaa | 5700 |
| gctgggctgt | gtgcacgaac | ccccgttca | gcccgaccgc | tgcgccttat ccggtaacta | 5760 |
| tcgtcttgag | tccaacccgg | taagacacga | cttatcgcca | ctggcagcag ccactggtaa | 5820 |
| caggattagc | agagcgaggt | atgtaggcgg | tgctacagag | ttcttgaagt ggtggcctaa | 5880 |
| ctacggctac | actagaagga | cagtatttgg | tatctgcgct | ctgctgaagc cagttacctt | 5940 |
| cggaaaaaga | gttggtagct | cttgatccgg | caaacaaacc | accgctggta gcggtggttt | 6000 |
| ttttgtttgc | aagcagcaga | ttacgcgcag | aaaaaaagga | tctcaagaag atcctttgat | 6060 |
| cttttctacg | gggtctgacg | ctcagtggaa | cgaaaactca | cgttaaggga ttttggtcat | 6120 |
| gagattatca | aaaaggatct | tcacctagat | ccttttaaat | taaaaatgaa gttttaaatc | 6180 |
| aatctaaagt | atatatgagt | aaacttggtc | tgacagtcta | ga | 6222 |

<210> SEQ ID NO 6
<211> LENGTH: 7376
<212> TYPE: DNA
<213> ORGANISM: Artificial Sequence
<220> FEATURE:
<223> OTHER INFORMATION: Synthetic- plasmid pK-DPD-1 (pYA4545 encoding extracellular domain of human PD-1)

<400> SEQUENCE: 6

| | | | | |
|---|---|---|---|---|
| gactcttcgc | gatgtacggg | ccagatatac | gcgttaactg | cagtctagat tatgcgaaag | 60 |
| gccatcctga | cggatggcct | ttttgtttaa | acggatccgc | gacattgatt attgactagt | 120 |
| tattaatagt | aatcaattac | ggggtcatta | ggggactttc | cggggacttt cctccccacg | 180 |
| cggggggactt | ccgccacgg | gcggggactt | ccggggact | ttccgttcat agcccatata | 240 |
| tggagttccg | cgttacataa | cttacggtaa | atggcccgcc | tggctgaccg cccaacgacc | 300 |
| cccgcccatt | gacgtcaata | atgacgtatg | ttcccatagt | aacgccaata gggactttcc | 360 |
| attgacgtca | atgggtggac | tatttacggt | aaactgccca | cttggcagta catcaagtgt | 420 |
| atcatatgcc | aagtacgccc | cctattgacg | tcaatgacgg | taaatggccc gcctggcatt | 480 |
| atgcccagta | catgacctta | tgggactttc | ctacttggca | gtacatctac gtattagtca | 540 |
| tcgctattac | catggtgatg | cggttttggc | agtacatcaa | tgggcgtgga tagcggtttg | 600 |
| actcacgggg | atttccaagt | ctccacccca | ttgacgtcaa | tgggagtttg ttttggcacc | 660 |
| aaaatcaacg | ggactttcca | aaatgtcgta | acaactccgc | cccattgacg caaatgggcg | 720 |
| gtaggcgtgt | acggtgggag | gtctatataa | gcagagctct | ctggctaact agagaaccca | 780 |
| ctgcttactg | gcttatcgaa | attaatacga | ctcactatag | ggagacccaa gctggctagc | 840 |
| gtttaaactt | aagcttggta | ccaccatggg | cttagactcc | ccagacaggc cctggaaccc | 900 |
| ccccaccttc | tccccagccc | tgctcgtggt | gaccgaaggg | gacaacgcca ccttcacctg | 960 |
| cagcttctcc | aacacatcgg | agagcttcgt | gctaaactgg | taccgcatga gccccagcaa | 1020 |
| ccagacggac | aagctggccg | ccttcccga | ggaccgcagc | cagcccggcc aggactgccg | 1080 |
| cttccgtgtc | acacaactgc | ccaacgggcg | tgacttccac | atgagcgtgg tcagggcccg | 1140 |

```
gcgcaatgac agcggcacct acctctgtgg ggccatctcc ctggccccca aggcgcagat    1200
caaagagagc ctgcgggcag agctcagggt gacagagaga agggcagaag tgcccacagc    1260 ccacccagc ccctcaccct aatagctcga gaatgcttcg agcagacatg ataagataca    1320
ttgatgagtt tggacaaacc acaactagaa tgcagtgaaa aaaatgcttt atttgtgaaa    1380
tttgtgatgc tattgctta tttgtaacca ttataagctg caataaacaa gttaacaaca    1440
acaattgcat tcattttatg tttcaggttc agggggagat gtgggaggtt ttttaaagca    1500
agtaaaacct ctacaaatgt ggtaaaatcc gataaggatc gatccggggc atgcaaccag    1560
ctgtggaatg tgtgtcagtt agggtgtgga aagtccccag gctccccagc aggcagaagt    1620
atgcaaagca tgtggggatg cggtgggctc tatggcttct actgggcggt tttatggaca    1680
gcaagcgaac cggaattgcc agctggggcg ccctctggta aggttgggaa gccctgcaaa    1740
gtaaactgga tggctttctc gccgccaagg atctgtcgac ccctagattt cagtgcaatt    1800
tatctcttca aatgtagcac ctgaagtcag ccccatacga tataagttgt tggaagatct    1860
agcccgccta atgagcgggc tttttttta ttcgcaattc cccgatgcat aatgtgcctg    1920
tcaaatggac gaagcaggga ttctgcaaac cctatgctac tccgtcaagc cgtcaattgt    1980
ctgattcgtt accaattatg acaacttgac ggctacatca ttcacttttt cttcacaacc    2040
ggcacgaaac tcgctcgggc tggccccggt gcattttta aatactcgcg agaaatagag    2100
ttgatcgtca aaaccaacat tgcgaccgac ggtggcgata ggcatccggg tagtgctcaa    2160
aagcagcttc gcctgactaa tgcgttggtc ctcgcgccag cttaagacgc taatccctaa    2220
ctgctggcgg aaaagatgtg acagacgcga cggcgacaag caaacatgct gtgcgacgct    2280
ggcgatatca aaattgctgt ctgccaggtg atcgctgatg tactgacaag cctcgcgtac    2340
ccgattatcc atcggtggat ggagcgactc gttaatcgct tccatgcgcc gcagtaacaa    2400
ttgctcaagc agatttatcg ccagcagctc cgaatagcgc ccttcccctt gcccggcgtt    2460
aatgatttgc ccaaacaggt cgctgaaatg cggctggtgc gcttcatccg ggcgaaagaa    2520
acccgtattg gcaaatattg acggccagtt aagccattca tgccagtagg cgcgcggacg    2580
aaagtaaacc cactggtgat accattcgcg agcctccgga tgacgaccgt agtgatgaat    2640
ctctcctggc gggaacagca aaatatcacc cggtcggcag acaaattctc gtccctgatt    2700
tttcaccacc ccctgaccgc gaatggtgag attgagaata taacctttca ttcccagcgg    2760
tcggtcgata aaaaaatcga gataaccgtt ggcctcaatc ggcgttaaac ccgccaccag    2820
atgggcgtta acgagtatc ccggcagcag gggatcattt tgcgcttcag ccatactttt    2880
catactccca ccattcagag aagaaaccaa ttgtccatat tgcatcagac attgccgtca    2940
ctgcgtcttt tactggctct ctcgctaac ccaaccggta accccgctta ttaaaagcat    3000
tctgtaacaa agcgggacca aagccatgac aaaaacgcgt aacaaaagtg tctataatca    3060
cggcagaaaa gtccacattg attatttgca cggcgtcaca ctttgctatg ccatagcatt    3120
tttatccata agattagcgg atcctacctg acgctttta tcgcaactct ctactgtttc    3180 tccataccg tttttttggg ctagcgaatt ctgagaacaa actaagtgga taaatttcgt    3240
gttcaggggc caacgaagct ccaggcgaa gtcacaattt ccggcgctaa aaatgctgct    3300
ctgcctatcc tttttgccgc actactggcg gaagaaccgg tagagatcca gaacgtcccg    3360
aaactgaaag acgtcgatac atcaatgaag ctgctaagcc agctgggtgc gaaagtagaa    3420
cgtaatggtt ctgtgcatat tgatgcccgc gacgttaatg tattctgcgc accttacgat    3480
ctggttaaaa ccatgcgtgc ttctatctgg gcgctggggc cgctggtagc gcgctttggt    3540
```

```
caggggcaag tttcactacc tggcggttgt acgatcggtg cgcgtccggt tgatctacac    3600
atttctggcc tcgaacaatt aggcgcgacc atcaaactgg aagaaggtta cgttaaagct    3660
tccgtcgatg gtcgtttgaa aggtgcacat atcgtgatgg ataaagtcag cgttggcgca    3720
acggtgacca tcatgtgtgc tgcaaccctg gcggaaggca ccacgattat tgaaaacgca    3780
gcgcgtgaac cggaaatcgt cgataccgcg aacttcctga ttacgctggg tgcgaaaatt    3840
agcggtcagg gcaccgatcg tatcgtcatc gaaggtgtgg aacgtttagg cggcggtgtc    3900
tatcgcgttc tgccggatcg tatcgaaacc ggtactttcc tggtggcggc ggcgatttct    3960
cgcggcaaaa ttatctgccg taacgcgcag ccagatactc tcgacgccgt gctggcgaaa    4020
ctgcgtgacg ctggagcgga catcgaagtc ggcgaagact ggattagcct ggatatgcat    4080
ggcaaacgtc cgaaggctgt taacgtacgt accgcgccgc atccggcatt cccgaccgat    4140
atgcaggccc agttcacgct gttgaacctg gtggcagaag ggaccgggtt tatcaccgaa    4200
acggtctttg aaaaccgctt tatgcatgtg ccagagctga ccgtatgggc gcgcacgcc     4260 gaaatcgaaa gcaataccgt tatttgtcac ggtgttgaaa actttctgg cgcacaggtt     4320 atggcaaccg atctgcgtgc atcagcaagc ctggtgctgg ctggctgtat tgcggaaggg    4380
acgacggtgg ttgatcgtat ttatcacatc gatcgtggct acgaacgcat tgaagacaaa    4440
ctgcgcgctt taggtgcaaa tattgagcgt gtgaaaggcg aataagaatt caggaaaaaa    4500
acgctgtgaa aaatgttggt tttatcggct ggcgcgaat ggtcggctct gttctcatgc     4560
aacgcatggt agaggagcgc gatttcgacg ctattcgccc tgttttcttt tctacctccc    4620
agtttggaca ggcggcgccc accttcggcg acacctccac cggcacgcta caggacgctt    4680
ttgatctgga tgcgctaaaa gcgctcgata tcatcgtgac ctgccagggc ggcgattata    4740
ccaacgaaat ttatccaaag ctgcgcgaaa gcggatggca gggttactgg attgatgcgg    4800
cttctacgct gcgcatgaaa gatgatgcca ttattattct cgacccggtc aaccaggacg    4860
tgattaccga cggcctgaac aatggcgtga agacctttgt gggcggtaac tgtaccgtta    4920
gcctgatgtt gatgtcgctg gcggtctct tgcccataa tctcgttgac tgggtatccg      4980
tcgcgaccta tcaggccgcc tccgcgcgcg cgcgcgccca tgcgcgcgag ctgttaaccc    5040
agatgggtca gttgtatggc catgtcgccg atgaactggc gacgccgtct tccgcaattc    5100
ttgatattga acgcaaagtt acggcattga cccgcagcgg cgagctgccg gttgataact    5160
ttggcgtacc gctggcggga agcctgatcc cctggatcga caaacagctc gataacggcc    5220
agagccgcga agagtggaaa ggccaggcgg aaaccaacaa gattctcaat actgcctctg    5280
tgattccggt tgatggtttg tgtgtgcgcg tcggcgcgct gcgctgtcac agccaggcgt    5340
tcaccatcaa gctgaaaaaa gaggtatcca ttccgacggt ggaagaactg ctggcggcac    5400
ataatccgtg ggcgaaagtg gtgccgaacg atcgtgatat cactatgcgc gaattaaccc    5460
cggcggcggt gaccggcacg ttgactacgc cggttggtcg tctgcgtaag ctgaacatgg    5520
ggccagagtt cttgtcggcg tttaccgtag gcgaccagtt gttatgggc gccgccgagc     5580 cgctgcgtcg aatgctgcgc cagttggcgt agtctagctg cacgataccg tcgacttgta    5640
catagactcg ctccgaaatt aaagaacact taaattatct actaaaggaa tctttagtca    5700 agtttatttta agatgactta actatgaata cacaattgat gggtgagcgt aggatcttcc    5760
attattgaag catttatcag ggttattgtc tcatgagctt ggctgttttg gcggatgaga    5820
gaagattttc agcctgatac agattaaatc agaacgcaga agcggtctga taaaacagtt    5880
tgcctggcgg cagtagcgcg gtggtcccac ctgacccat gccgaactca gaagtgaaac     5940
```

```
gccgtagcgc cgatggtagt gtggggtctc cccatgcgag agtagggaac tgccaggcat      6000
caaataaaac gaaaggctca gtcgaaagac tgggcctttc gttttatctg ttgtttgtcg      6060
gtgaacgctc tcctgagtag gacaaatccg ccgggagcgg atttgaacgt tgcgaagcaa      6120
cggcccggag ggtggcgggc aggacgcccg ccataaactg ccaggcatca aattaagcag      6180
aaggccatcc tgacggatgg cctttttgcg tttctacaaa ctcttttgt ttatttttct       6240 aaatacattc aaatatgtat ccgctcatga gacaataacc ctgataaatg cttcaataat      6300
ggaagatctt ccaacatcac aggtaaacag aaacgtcggg tcgatcggga aattctttcc      6360 cggacgcgc ggggttgggc aagccgcagg gcgtcagtg cttttagcgg gtgtcggggc        6420
agccctgaac cagtcacggg atcgatctgt gcggtatttc acaccgcata caggtggcac      6480
ttttcgggga atgtgcgcg gaaccccat ttgtttattt ttctaaatac attcaaatat        6540
gtatccgctc atgagacaat aaccctgata aatgcttcaa taatagcacg tgctaaaact     6600 tcattttaa tttaaaagga tctaggtgaa gatcctttt gataatctca tgaccaaaat       6660
cccttaacgt gagttttcgt tccactgagc gtcagacccc gtagaaaaga tcaaaggatc     6720
ttcttgagat cctttttttc tgcgcgtaat ctgctgcttg caaacaaaaa aaccaccgct     6780
accagcggtg gtttgtttgc cggatcaaga gctaccaact cttttttcga aggtaactgg    6840
cttcagcaga gcgcagatac caaatactgt ccttctagtg tagccgtagt taggccacca     6900
cttcaagaac tctgtagcac cgcctacata cctcgctctg ctaatcctgt taccagtggc    6960
tgctgccagt ggcgataagt cgtgtcttac cgggttggac tcaagacgat agttaccgga    7020
taaggcgcag cggtcgggct gaacgggggg ttcgtgcaca cagcccagct tggagcgaac     7080
gacctacacc gaactgagat acctacagcg tgagctatga gaaagcgcca cgcttcccga     7140
agggagaaag gcggacaggt atccggtaag cggcagggtc ggaacaggag agcgcacgag     7200
ggagcttcca gggggaaacg cctggtatct ttatagtcct gtcgggtttc gccacctctg     7260
acttgagcgt cgatttttgt gatgctcgtc aggggggcgg agcctatgga aaaacgccag    7320
caacgcggcc ttttacggt tcctgggctt ttgctggcct tttgctcaca tgttct          7376
```

<210> SEQ ID NO 7
<211> LENGTH: 6840
<212> TYPE: DNA
<213> ORGANISM: Artificial Sequence
<220> FEATURE:
<223> OTHER INFORMATION: Synthetic- plasmid pK-SIRP-alpha (pYA3681 encoding extracellular domain of human SIRP-alpha)

<400> SEQUENCE: 7

```
agatctagcc cgcctaatga gcgggctttt ttttaattcg caattccccg atgcataatg       60
tgcctgtcaa atggacgaag cagggattct gcaaaccta tgctactccg tcaagccgtc      120
aattgtctga ttcgttacca attatgacaa cttgacggct acatcattca cttttttcttc    180 acaaccggca cggaactcgc tcgggctggc cccggtgcat ttttttaaata cccgcgagaa    240 atagagttga tcgtcaaaac caacattgcg accgacggtg gcgataggca tccgggtggt     300
gctcaaaagc agcttcgcct ggctgatacg ttggtcctcg cgccagctta agacgctaat     360
ccctaactgc tggcggaaaa gatgtgacag acgcgacggc gacaagcaaa catgctgtgc    420
gacgctggcg atatcaaaat tgctgtctgc caggtgatcg ctgatgtact gacaagcctc     480
gcgtacccga ttatccatcg gtggatggag cgactcgtta atcgcttcca tgcgccgcag     540
taacaattgc tcaagcagat ttatcgccag cagctccgaa tagcgccctt cccccttgccc    600
```

```
ggcgttaatg atttgcccaa acaggtcgct gaaatgcggc tggtgcgctt catccgggcg    660
aaagaacccc gtattggcaa atattgacgg ccagttaagc cattcatgcc agtaggcgcg    720
cggacgaaag taaacccact ggtgatacca ttcgcgagcc tccggatgac gaccgtagtg    780
atgaatctct cctggcggga acagcaaaat atcacccgt  cggcaaacaa attctcgtcc    840
ctgattttc  accaccccct gaccgcgaat ggtgagattg agaatataac ctttcattcc    900
cagcggtcgg tcgataaaaa aatcgagata accgttggcc tcaatcggcg ttaaacccgc    960
caccagatgg gcattaaacg agtatcccgg cagcagggga tcattttgcg cttcagccat   1020
acttttcata ctcccgccat tcagagaaga aaccaattgt ccatattgca tcagacattg   1080
ccgtcactgc gtcttttact ggctcttctc gctaaccaaa ccggtaaccc cgcttattaa   1140
aagcattctg taacaaagcg ggaccaaagc catgacaaaa acgcgtaaca aaagtgtcta   1200
taatcacggc agaaaagtcc acattgatta tttgcacggc gtcacacttt gctatgccat   1260
agcattttta tccataagat tagcggatcc tacctgacgc tttttatcgc aactctctac   1320
tgtttctcca tacccgtttt tttgggctag cgaattctga gaacaaacta aatggataaa   1380
tttcgtgttc aggggccaac gaagctccag ggcgaagtca caatttccgg cgctaaaaat   1440
gctgctctgc ctatcctttt tgccgcacta ctggcggaag aaccggtaga gatccagaac   1500
gtcccgaaac tgaaagacgt cgatacatca atgaagctgc taagccagct gggtgcgaaa   1560
gtagaacgta atggttctgt gcatattgat gcccgcgacg ttaatgtatt ctgcgcacct   1620
tacgatctgg ttaaaaccat gcgtgcttct atctgggcgc tggggccgct ggtagcgcgc   1680
tttggtcagg ggcaagtttc actacctggc ggttgtacga tcggtgcgcg tccggttgat   1740
ctacacattt ctggcctcga acaattaggc gcgaccatca aactggaaga aggttacgtt   1800
aaagcttccg tcgatggtcg tttgaaaggt gcacatatcg tgatggataa agtcagcgtt   1860
ggcgcaacgg tgaccatcat gtgtgctgca accctggcgg aaggcaccac gattattgaa   1920
aacgcagcgc gtgaaccgga aatcgtcgat accgcgaact tcctgattac gctgggtgcg   1980
aaaattagcg gtcagggcac cgatcgtatc gtcatcgaag gtgtggaacg tttaggcggc   2040
ggtgtctatc gcgttctgcc ggatcgtatc gaaaccggta cttttcctggt ggcggcggcg   2100
atttctcgcg gcaaaattat ctgccgtaac gcgcagccag atactctcga cgccgtgctg   2160
gcgaaactgc gtgacgctgg agcggacatc gaagtcggcg aagactggat tagcctggat   2220
atgcatggca aacgtccgaa ggctgttaac gtacgtaccg cgccgcatcc ggcattcccg   2280
accgatatgc aggcccagtt cacgctgttg aacctggtgg cagaagggac cgggtttatc   2340
accgaaacgg tctttgaaaa ccgctttatg catgtgccag agctgagccg tatgggcgcg   2400
cacgccgaaa tcgaaagcaa taccgttatt tgtcacggtg ttgaaaaact ttctggcgca   2460
caggttatgg caaccgatct gcgtgcatca gcaagcctgg tgctggctgg ctgtattgcg   2520
gaagggacga cggtggttga tcgtatttat cacatcgatc gtggctacga acgcattgaa   2580
gacaaactgc gcgctttagg tgcaaatatt gagcgtgtga aaggcgaata agaattcagg   2640
aaaaaaacgc tgtgaaaaat gttggtttta tcggctggcg cggaatggtc ggctctgttc   2700
tcatgcaacg catggtagag gagcgcgatt tcgacgctat tcgccctgtt ttcttttcta   2760
cctcccagtt tggacaggcg gcgcccacct tcggcgacac ctccaccggc acgctacagg   2820
acgcttttga tctggatgcg ctaaaagcgc tcgatatcat cgtgacctgc cagggcggcg   2880
attataccaa cgaaatttat ccaaagctgc gcgaaagcgg atggcagggt tactggattg   2940
atgcggcttc tacgctgcgc atgaaagatg atgccattat tattctcgac ccggtcaacc   3000
```

```
aggacgtgat taccgacggc ctgaacaatg gcgtgaagac ctttgtgggc ggtaactgta    3060
ccgttagcct gatgttgatg tcgctgggcg gtctctttgc ccataatctc gttgactggg    3120
tatccgtcgc gacctatcag gccgcctccg gcggcggcgc gccatatg cgcgagctgt      3180 taacccagat gggtcagttg tatggccatg tcgccgatga actggcgacg ccgtcttccg    3240
caattcttga tattgaacgc aaagttacgg cattgacccg cagcggcgag ctgccggttg    3300
ataactttgg cgtaccgctg gcgggaagcc tgatccccctg gatcgacaaa cagctcgata   3360
acggccagag ccgcgaagag tggaaaggcc aggcggaaac caacaagatt ctcaatactg    3420
cctctgtgat tccggttgat ggtttgtgtg tgcgcgtcgg cgcgctgcgc tgtcacagcc    3480
aggcgttcac catcaagctg aaaaaagagg tatccattcc gacggtggaa gaactgctgg    3540
cggcacataa tccgtgggcg aaagtggtgc cgaacgatcg tgatatcact atgcgcgaat    3600
taaccccggc ggcggtgacc ggcacgttga ctacgccggt tggtcgtctg cgtaagctga    3660
acatggggcc agagttcttg tcggcgttta ccgtaggcga ccagttgtta tggggcgccg    3720
ccgagccgct gcgtcgaatg ctgcgccagt tggcgtagtc tagctgcacg ataccgtcga    3780
cttgtacata gactcgctcc gaaattaaag aacacttaaa ttatctacta aaggaatctt    3840
tagtcaagtt tatttaagat gacttaacta tgaatacaca attgatgggt gagcgtagga    3900
gcatgcttat gcgaaaggcc atcctgacgg atggccttt tggatcttcc ggaagacctt     3960
ccattctgaa atgagctgtt gacaattaat catccggctc gtataatgtg tggaattgtg    4020
agcggataac aatttcacac aggaaacaga ccatgggcgt tgcgggcgaa gaagaactgc    4080
aggttatcca gccggacaaa tctgtttctg ttgcggcggg cgaatctgcg atcctgcact    4140
gcaccgttac ctctctgatc ccggttggcc cgatccagtg gttccgtggc gcgggcccgg    4200
cgcgtgaact gatctacaac cagaaagaag gccacttccc gcgtgttacc accgtttctg    4260
aatctaccaa acgtgaaaac atggacttct ctatctctat ctctaacatc accccggcgg    4320
acgcgggcac ctactactgc gttaaattcc gtaaaggctc tccggacacc gaattcaaat    4380
ctggcgcggg caccgaactg tctgttcgtg cgaaaccgtc tgcgccagtt gtaagcggcc    4440
cggcggcgcg tgcgacccccg cagcatactg ttagcttcac ctgcgaatcg cacggcttct    4500
ctccgcgtga catcacccctg aaatggttca aaaacggcaa cgaactgtct gacttccaga    4560
ccaacgttga cccggttggc gaatctgttt cttactctat ccactctacc gcgaaagttg    4620
ttctgacccg tgaagacgtt cactctcagg ttatctgcga agttgcgcac gttaccctgc    4680
agggcgaccc gctgcgtggc accgcgaacc tgtctgaaac catccgtgtt ccgccgaccc    4740
tggaagttac ccagcagccg gttcgtgcgg aaaaccaggt taacgttacc tgccaggttc    4800
gtaaattcta cccgcagcgt ctgcagctga acctggctgga gaatggcaac gtaagccgta    4860
ccgaaaccgc gtctaccgtt accgaaaaca agacggcac ctacaactgg atgtcttggc      4920
tgctggttaa cgtttctgcg caccgtgacg acgttaaact gacctgccag gttgaacatg    4980
atggccagcc ggcggtaagc aaatctcacg acctgaaagt ttctgcgcac ccgaaagaac    5040
agggctctaa caccgcggcg gaaaacaccg gctctaacga acgttaatag cccggggatc    5100
cgtcgacctg cagccaagct cccaagcttg gctgttttgg cggatgagag aagattttca    5160
gcctgataca gattaaatca gaacgcagaa gcggtctgat aaaacagaat ttgcctggcg    5220
gcagtagcgc ggtggtccca cctgacccca tgccgaactc agaagtgaaa cgccgtagcg    5280
ccgatggtag tgtggggtct ccccatgcga gagtagggaa ctgccaggca tcaaataaaa    5340
cgaaaggctc agtcgaaaga ctgggccttt cgttttatct gttgtttgtc ggtgaacgct    5400
```

| ctcctgagta ggacaaatcc gccgggagcg gatttgaacg ttgcgaagca acggcccgga | 5460 |
| gggtggcggg caggacgccc gccataaact gccaggcatc aaattaagca gaaggccatc | 5520 |
| ctgacggatg gccttttgc gtttctacaa actcttttgt ttattttct aaatacattc | 5580 |
| aaatatgtat ccgctcatga gacaataacc ctgataaatg cttcaataat ggaagatctt | 5640 |
| ccaacatcac aggtaaacag aaacgtcggg tcgatcggga aattctttcc cggacggcgc | 5700 |
| ggggttgggc aagccgcagg cgcgtcagtg cttttagcgg gtgtcggggc gcagccatga | 5760 |
| cccagtcacg tagcgatagc ggagtgtata ctggcttaac tatgcggcat cagagcagat | 5820 |
| tgtactgaga gtgcaccata tgcggtgtga ataccgcac agatgcgtaa ggagaaaata | 5880 |
| ccgcatcagg cgctcttccg cttcctcgct cactgactcg ctgcgctcgg tcgttcggct | 5940 |
| gcggcgagcg gtatcagctc actcaaaggc ggtaatacgg ttatccacag aatcagggga | 6000 |
| taacgcagga aagaacatgt gagcaaaagg ccagcaaaag gccaggaacc gtaaaaaggc | 6060 |
| cgcgttgctg gcgtttttcc ataggctccg ccccctgac gagcatcaca aaaatcgacg | 6120 |
| ctcaagtcag aggtggcgaa acccgacagg actataaaga taccaggcgt ttccccctgg | 6180 |
| aagctccctc gtgcgctctc ctgttccgac cctgccgctt accggatacc tgtccgcctt | 6240 |
| tctcccttcg ggaagcgtgg cgctttctca gctcacgc tgtaggtatc tcagttcggt | 6300 |
| gtaggtcgtt cgctccaagc tgggctgtgt gcacgaaccc cccgttcagc ccgaccgctg | 6360 |
| cgccttatcc ggtaactatc gtcttgagtc aacccggta agacacgact tatcgccact | 6420 |
| ggcagcagcc actggtaaca ggattagcag agcgaggtat gtaggcggtg ctacagagtt | 6480 |
| cttgaagtgg tggcctaact acggctacac tagaaggaca gtatttggta tctgcgctct | 6540 |
| gctgaagcca gttaccttcg gaaaaagagt ggtagctct tgatccggca acaaaccac | 6600 |
| cgctggtagc ggtggttttt ttgtttgcaa gcagcagatt acgcgcagaa aaaaaggatc | 6660 |
| tcaagaagat cctttgatct tttctacggg gtctgacgct cagtggaacg aaaactcacg | 6720 |
| ttaagggatt ttggtcatga gattatcaaa aaggatcttc acctagatcc ttttaaatta | 6780 |
| aaaatgaagt tttaaatcaa tctaaagtat atatgagtaa acttggtctg acagtctaga | 6840 |

<210> SEQ ID NO 8
<211> LENGTH: 7994
<212> TYPE: DNA
<213> ORGANISM: Artificial Sequence
<220> FEATURE:
<223> OTHER INFORMATION: Synthetic- plasmid pK-DSIRP-alpha (pYA4545 encoding extracellular domain of human SIRP-alpha)

<400> SEQUENCE: 8

| gactcttcgc gatgtacggg ccagatatac gcgttaactg cagtctagat tatgcgaaag | 60 |
| gccatcctga cggatggcct ttttgtttaa acggatccgc gacattgatt attgactagt | 120 |
| tattaatagt aatcaattac ggggtcatta ggggactttc cggggacttt cctccccacg | 180 |
| cgggggactt tccgccacgg gcgggggactt tccgggggact ttccgttcat agcccatata | 240 |
| tggagttccg cgttacataa cttacggtaa atggcccgcc tggctgaccg cccaacgacc | 300 |
| cccgcccatt gacgtcaata atgacgtatg ttcccatagt aacgccaata gggactttcc | 360 |
| attgacgtca atgggtggac tatttacggt aaactgccca cttggcagta catcaagtgt | 420 |
| atcatatgcc aagtacgccc cctattgacg tcaatgacgg taaatggccc gcctggcatt | 480 |
| atgcccagta catgacctta tgggactttc ctacttggca gtacatctac gtattagtca | 540 |
| tcgctattac catggtgatg cggttttggc agtacatcaa tgggcgtgga tagcggtttg | 600 |

```
actcacgggg atttccaagt ctccacccca ttgacgtcaa tgggagtttg ttttggcacc    660
aaaatcaacg ggacttttcca aaatgtcgta acaactccgc cccattgacg caaatgggcg    720
gtaggcgtgt acggtgggag gtctatataa gcagagctct ctggctaact agagaaccca    780
ctgcttactg gcttatcgaa attaatacga ctcactatag ggagacccaa gctggctagc    840
gtttaaactt aagcttggta ccaccatggg agtggcgggt gaggaggagc tgcaggtgat    900
tcagcctgac aagtccgtat cagttgcagc tggagagtcg gccattctgc actgcactgt    960
gacctccctg atccctgtgg ggcccatcca gtggttcaga ggagctggac cagcccggga   1020
attaatctac aatcaaaaag aaggccactt ccccgggta caactgtttt cagagtccac   1080
aaagagagaa aacatggact tttccatcag catcagtaac atcaccccag cagatgccgg   1140
cacctactac tgtgtgaagt tccggaaagg gagccctgac acggagttta agtctggagc   1200
aggcactgag ctgtctgtgc gtgccaaacc ctctgcccc gtggtatcgg gccctgcggc   1260
gagggccaca cctcagcaca cagtgagctt cacctgcgag tcccacggct tctcacccag   1320
agacatcacc ctgaaatggt tcaaaaatgg gaatgagctc tcagacttcc agaccaacgt   1380
ggaccccgta ggagagagcg tgtcctacag catccacagc acagccaagg tggtgctgac   1440
ccgcgaggac gttcactctc aagtcatctg cgaggtggcc cacgtcacct gcagggggga   1500
ccctcttcgt gggactgcca acttgtctga ccatccga gttccaccca ccttggaggt   1560
tactcaacag cccgtgaggg cagagaacca ggtgaatgtc acctgccagg tgaggaagtt   1620 ctaccccag agactacagc tgacctggtt ggagaatgga acgtgtccc ggacagaaac   1680 ggcctcaacc gttacagaga acaaggatgg tacctacaac tggatgagct ggctcctggt   1740
gaatgtatct gcccacaggg atgatgtgaa gctcacctgc caggtggagc atgacgggca   1800
gccagcggtc agcaaaagcc atgacctgaa ggtctcagcc cacccgaagg agcagggctc   1860
aaataccgcc gctgagaaca ctggatctaa tgaacggtaa tagctcgaga atgcttcgag   1920
cagacatgat aagatacatt gatgagtttg gacaaaccac aactagaatg cagtgaaaaa   1980
aatgctttat ttgtgaaatt tgtgatgcta ttgctttatt tgtaaccatt ataagctgca   2040
ataaacaagt taacaacaac aattgcattc attttatgtt tcaggttcag ggggagatgt   2100
gggaggtttt ttaaagcaag taaaacctct acaaatgtgg taaaatccga taaggatcga   2160
tccggggcat gcaaccagct gtggaatgtg tgtcagttag ggtgtggaaa gtccccaggc   2220
tccccagcag gcagaagtat gcaaagcatg tggggatgcg gtgggctcta tggcttctac   2280
tgggcggttt tatggacagc aagcgaaccg gaattgccag ctggggcgcc ctctggtaag   2340
gttgggaagc cctgcaaagt aaactggatg ctttctcgc cgccaaggat ctgtcgaccc   2400
ctagatttca gtgcaattta tctcttcaaa tgtagcacct gaagtcagcc ccatacgata   2460
taagttgttg aagatctag cccgcctaat gagcgggctt tttttaatt cgcaattccc   2520 cgatgcataa tgtgcctgtc aaatggacga agcaggatt ctgcaaaccc tatgctactc   2580
cgtcaagccg tcaattgtct gattcgttac caattatgac aacttgacgg ctacatcatt   2640
cactttttct tcacaaccgg cacgaaactc gctcgggctg ccccggtgc atttttaaa   2700 tactcgcgag aaatagagtt gatcgtcaaa accaacattg cgaccgacgg tggcgatagg   2760
catccgggta gtgctcaaaa gcagcttcgc ctgactaatg cgttggtcct cgcgccagct   2820
taagacgcta atccctaact gctggcggaa aagatgtgac agacgcgacg gcgacaagca   2880
aacatgctgt gcgacgctgg cgatatcaaa attgctgtct gccaggtgat cgctgatgta   2940
ctgacaagcc tcgcgtaccc gattatccat cggtggatgg agcgactcgt taatcgcttc   3000
```

```
catgcgccgc agtaacaatt gctcaagcag atttatcgcc agcagctccg aatagcgccc      3060
ttccccttgc ccggcgttaa tgatttgccc aaacaggtcg ctgaaatgcg gctggtgcgc      3120
ttcatccggg cgaaagaaac ccgtattggc aaatattgac ggccagttaa gccattcatg      3180
ccagtaggcg cgcggacgaa agtaaaccca ctggtgatac cattcgcgag cctccggatg      3240
acgaccgtag tgatgaatct ctcctggcgg gaacagcaaa atatcacccg gtcggcagac      3300
aaattctcgt ccctgatttt tcaccacccc ctgaccgcga atggtgagat tgagaatata      3360 accttttcatt cccagcggtc ggtcgataaa aaaatcgaga taaccgttgg cctcaatcgg      3420
cgttaaaccc gccaccagat gggcgttaaa cgagtatccc ggcagcaggg gatcattttg      3480
cgcttcagcc atacttttca tactcccacc attcagagaa gaaaccaatt gtccatattg      3540
catcagacat tgccgtcact gcgtctttta ctggctcttc tcgctaaccc aaccggtaac      3600
cccgcttatt aaaagcattc tgtaacaaag cgggaccaaa gccatgacaa aaacgcgtaa      3660
caaaagtgtc tataatcacg gcagaaaagt ccacattgat tatttgcacg gcgtcacact      3720
ttgctatgcc atagcatttt tatccataag attagcggat cctacctgac gctttttatc      3780
gcaactctct actgtttctc catacccgtt ttttttgggct agcgaattct gagaacaaac      3840
taagtggata aatttcgtgt tcaggggcca acgaagctcc agggcgaagt cacaatttcc      3900
ggcgctaaaa atgctgctct gcctatcctt tttgccgcac tactggcgga agaaccggta      3960
gagatccaga acgtcccgaa actgaaagac gtcgatacat caatgaagct gctaagccag      4020
ctgggtgcga aagtagaacg taatggttct gtgcatattg atgcccgcga cgttaatgta      4080
ttctgcgcac cttacgatct ggttaaaacc atgcgtgctt ctatctgggc gctggggccg      4140
ctggtagcgc gctttggtca ggggcaagtt tcactacctg gcggttgtac gatcggtgcg      4200
cgtccggttg atctacacat ttctggcctc gaacaattag gcgcgaccat caaactggaa      4260
gaaggttacg ttaaagcttc cgtcgatggt cgtttgaaag gtgcacatat cgtgatggat      4320
aaagtcagcg ttggcgcaac ggtgaccatc atgtgtgctg caaccctggc ggaaggcacc      4380
acgattattg aaaacgcagc gcgtgaaccg gaaatcgtcg ataccgcgaa cttcctgatt      4440
acgctgggtg cgaaaattag cggtcagggc accgatcgta tcgtcatcga aggtgtggaa      4500
cgtttaggcg gcggtgtcta tcgcgttctg ccggatcgta tcgaaaccgg tactttcctg      4560
gtggcggcgc cgatttctcg cggcaaaatt atctgccgta acgcgcagcc agatactctc      4620
gacgccgtgc tggcgaaact gcgtgacgct ggagcggaca tcgaagtcgg cgaagactgg      4680
attagcctgg atatgcatgg caaacgtccg aaggctgtta acgtacgtac cgcgccgcat      4740
ccggcattcc cgaccgatat gcaggcccag ttcacgctgt tgaacctggt ggcagaaggg      4800
accgggttta tcaccgaaac ggtctttgaa aaccgcttta tgcatgtgcc agagctgagc      4860
cgtatgggcg cgcacgccga aatcgaaagc aataccgtta tttgtcacgg tgttgaaaaa      4920
ctttctggcg cacaggttat ggcaaccgat ctgcgtgcat cagcaagcct ggtgctggct      4980
ggctgtattg cggaagggac gacggtggtt gatcgtattt atcacatcga tcgtggctac      5040
gaacgcattg aagacaaact gcgcgcttta ggtgcaaata ttgagcgtgt gaaaggcgaa      5100
taagaattca ggaaaaaaac gctgtgaaaa atgttggttt tatcggctgg cgcggaatgg      5160
tcggctctgt tctcatgcaa cgcatggtag aggagcgcga tttcgacgct attcgccctg      5220
ttttcttttc tacctcccag tttggacagg cggcgcccac cttcggcgac acctccaccg      5280
gcacgctaca ggacgctttt gatctggatg cgctaaaagc gctcgatatc atcgtgacct      5340
gccagggcgg cgattatacc aacgaaattt atccaaagct gcgcgaaagc ggatggcagg      5400
```

```
gttactggat tgatgcggct tctacgctgc gcatgaaaga tgatgccatt attattctcg    5460
acccggtcaa ccaggacgtg attaccgacg gcctgaacaa tggcgtgaag acctttgtgg    5520
gcggtaactg taccgttagc ctgatgttga tgtcgctggg cggtctcttt gcccataatc    5580
tcgttgactg ggtatccgtc gcgacctatc aggccgcctc cggcggcggc gcgcgccata    5640
tgcgcgagct gttaacccag atgggtcagt tgtatggcca tgtcgccgat gaactggcga    5700
cgccgtcttc cgcaattctt gatattgaac gcaaagttac ggcattgacc cgcagcggcg    5760
agctgccggt tgataacttt ggcgtaccgc tggcgggaag cctgatcccc tggatcgaca    5820
aacagctcga taacgccag agccgcgaag agtggaaagg ccaggcggaa accaacaaga    5880
ttctcaatac tgcctctgtg attccggttg atggtttgtg tgtgcgcgtc ggcgcgctgc    5940
gctgtcacag ccaggcgttc accatcaagc tgaaaaaaga ggtatccatt ccgacggtgg    6000
aagaactgct ggcggcacat aatccgtggg cgaaagtggt gccgaacgat cgtgatatca    6060
ctatgcgcga attaaccccg gcggcggtga ccggcacgtt gactacgccg gttggtcgtc    6120
tgcgtaagct gaacatgggg ccagagttct tgtcggcgtt taccgtaggc gaccagttgt    6180
tatggggcgc cgccgagccg ctgcgtcgaa tgctgcgcca gttggcgtag tctagctgca    6240
cgataccgtc gacttgtaca tagactcgct ccgaaattaa agaacactta aattatctac    6300
taaaggaatc tttagtcaag tttatttaag atgacttaac tatgaataca caattgatgg    6360
gtgagcgtag gatcttccat tattgaagca tttatcaggg ttattgtctc atgagcttgg    6420
ctgttttggc ggatgagaga agattttcag cctgatacag attaaatcag aacgcagaag    6480
cggtctgata aaacagtttg cctggcggca gtagcgcggt ggtcccacct gaccccatgc    6540
cgaactcaga agtgaaacgc cgtagcgccg atggtagtgt ggggtctccc catgcgagag    6600
tagggaactc ccaggcatca ataaaacga aaggctcagt cgaaagactg gcctttcgt    6660 tttatctgtt gtttgtcggt gaacgctctc ctgagtagga caaatccgcc gggagcggat    6720
ttgaacgttg cgaagcaacg gcccggaggg tggcgggcag gacgcccgcc ataaactgcc    6780
aggcatcaaa ttaagcagaa ggccatcctg acggatggcc ttttgcgtt tctacaaact    6840 cttttttgttt atttttctaa atacattcaa atatgtatcc gctcatgaga caataaccct    6900
gataaatgct tcaataatgg aagatcttcc aacatcacag gtaaacagaa acgtcgggtc    6960
gatcgggaaa ttcttttcccg gacggcgcgg ggttgggcaa gccgcaggcg cgtcagtgct    7020
tttagcgggt gtcggggcag ccctgaacca gtcacgggat cgatctgtgc ggtatttcac    7080
accgcataca ggtggcactt tcggggaaa tgtgcgcgga accctatttt gtttattttt    7140
ctaaatacat tcaaatatgt atccgctcat gagacaataa ccctgataaa tgcttcaata    7200
atagcacgtg ctaaaacttc attttaatt taaaggatc taggtgaaga tccttttga    7260 taatctcatg accaaaatcc cttaacgtga gttttcgttc cactgagcgt cagacccgt    7320 agaaaagatc aaaggatctt cttgagatcc ttttttctg cgcgtaatct gctgcttgca    7380
aacaaaaaaa ccaccgctac cagcggtggt ttgtttgccg gatcaagagc taccaactct    7440
ttttccgaag gtaactggct tcagcagagc gcagatacca atactgtcc ttctagtgta    7500 gccgtagtta ggccaccact tcaagaactc tgtagcaccg cctacatacc tcgctctgct    7560
aatcctgtta ccagtggctg ctgccagtgg cgataagtcg tgtcttaccg ggttggactc    7620
aagacgatag ttaccggata aggcgcagcg gtcgggctga acggggggtt cgtgcacaca    7680
gcccagcttg gagcgaacga cctacaccga actgagatac ctacagcgtg agctatgaga    7740
aagcgccacg cttcccgaag ggagaaaggc ggacaggtat ccggtaagcg gcagggtcgg    7800
```

```
aacaggagag cgcacgaggg agcttccagg gggaaacgcc tggtatcttt atagtcctgt    7860
cgggtttcgc cacctctgac ttgagcgtcg attttttgtga tgctcgtcag ggggggcggag    7920 cctatggaaa aacgccagca acgcggcctt tttacggttc ctgggctttt gctggccttt    7980
tgctcacatg ttct                                                      7994
```

```
<210> SEQ ID NO 9
<211> LENGTH: 22
<212> TYPE: DNA
<213> ORGANISM: Artificial Sequence
<220> FEATURE:
<223> OTHER INFORMATION: Synthetic- FZD NcoI Primer 1

<400> SEQUENCE: 9
cgccatggac cacggcttct gc                                               22

<210> SEQ ID NO 10
<211> LENGTH: 22
<212> TYPE: DNA
<213> ORGANISM: Artificial Sequence
<220> FEATURE:
<223> OTHER INFORMATION: Synthetic- FZD XmaI Primer 2

<400> SEQUENCE: 10
gccccgggct attacggcgc gc                                               22

<210> SEQ ID NO 11
<211> LENGTH: 22
<212> TYPE: DNA
<213> ORGANISM: Artificial Sequence
<220> FEATURE:
<223> OTHER INFORMATION: Synthetic- LRP6P NcoI Primer 1

<400> SEQUENCE: 11
cgccatgggc atcgtacccg aa                                               22

<210> SEQ ID NO 12
<211> LENGTH: 22
<212> TYPE: DNA
<213> ORGANISM: Artificial Sequence
<220> FEATURE:
<223> OTHER INFORMATION: Synthetic- LRP6P XmaI Primer 2

<400> SEQUENCE: 12
ccccgggcta ttagcatgac aa                                               22

<210> SEQ ID NO 13
<211> LENGTH: 22
<212> TYPE: DNA
<213> ORGANISM: Artificial Sequence
<220> FEATURE:
<223> OTHER INFORMATION: Synthetic- PD1 NcoI Primer 1

<400> SEQUENCE: 13
cgccatgggc ttagactccc ca                                               22

<210> SEQ ID NO 14
<211> LENGTH: 22
<212> TYPE: DNA
<213> ORGANISM: Artificial Sequence
<220> FEATURE:
<223> OTHER INFORMATION: Synthetic- PD1 XmaI Primer 2

<400> SEQUENCE: 14
gccccgggct attagggtga gg                                               22
```

```
<210> SEQ ID NO 15
<211> LENGTH: 22
<212> TYPE: DNA
<213> ORGANISM: Artificial Sequence
<220> FEATURE:
<223> OTHER INFORMATION: Synthetic- SPRI-alpha NcoI Primer 1

<400> SEQUENCE: 15
cgccatgggc gttgcgggcg aa                                           22

<210> SEQ ID NO 16
<211> LENGTH: 22
<212> TYPE: DNA
<213> ORGANISM: Artificial Sequence
<220> FEATURE:
<223> OTHER INFORMATION: Synthetic- SPRI-alpha XmaI Primer 2

<400> SEQUENCE: 16
gccccgggct attaacgttc gt                                           22

<210> SEQ ID NO 17
<211> LENGTH: 37
<212> TYPE: DNA
<213> ORGANISM: Artificial Sequence
<220> FEATURE:
<223> OTHER INFORMATION: Synthetic- FZD KpnI Primer 1

<400> SEQUENCE: 17
ggggtaccac caccatggac cacggcttct gccagcc                           37

<210> SEQ ID NO 18
<211> LENGTH: 36
<212> TYPE: DNA
<213> ORGANISM: Artificial Sequence
<220> FEATURE:
<223> OTHER INFORMATION: Synthetic- FZD XhoI Primer 2

<400> SEQUENCE: 18
gccgctcgag ctattaggga gctccgtcct cggagt                            36

<210> SEQ ID NO 19
<211> LENGTH: 37
<212> TYPE: DNA
<213> ORGANISM: Artificial Sequence
<220> FEATURE:
<223> OTHER INFORMATION: Synthetic- LRP6P KpnI Primer 1

<400> SEQUENCE: 19
ggggtaccac catgggcatt gtcccagagg ctttcct                           37

<210> SEQ ID NO 20
<211> LENGTH: 36
<212> TYPE: DNA
<213> ORGANISM: Artificial Sequence
<220> FEATURE:
<223> OTHER INFORMATION: Synthetic- LRP6P XhoI Primer 2

<400> SEQUENCE: 20
gccgctcgag ttcaagatga gctatcatgt taatag                            36

<210> SEQ ID NO 21
<211> LENGTH: 37
<212> TYPE: DNA
<213> ORGANISM: Artificial Sequence
<220> FEATURE:
<223> OTHER INFORMATION: Synthetic- PD1 KpnI Primer 1
```

```
<400> SEQUENCE: 21
ggggtaccac catgggctta gactccccag acaggcc                              37

<210> SEQ ID NO 22
<211> LENGTH: 35
<212> TYPE: DNA
<213> ORGANISM: Artificial Sequence
<220> FEATURE:
<223> OTHER INFORMATION: Synthetic- PD1 XhoI Primer 2

<400> SEQUENCE: 22
gccgctcgag ctattagggt gaggggctgg ggtgg                                35

<210> SEQ ID NO 23
<211> LENGTH: 35
<212> TYPE: DNA
<213> ORGANISM: Artificial Sequence
<220> FEATURE:
<223> OTHER INFORMATION: Synthetic- SPRI-alpha KpnI Primer 1

<400> SEQUENCE: 23
ggggtaccac catgggagtg gcgggtgagg aggag                                35

<210> SEQ ID NO 24
<211> LENGTH: 36
<212> TYPE: DNA
<213> ORGANISM: Artificial Sequence
<220> FEATURE:
<223> OTHER INFORMATION: Synthetic- SPRI-alpha XhoI Primer 2

<400> SEQUENCE: 24
gccgctcgag ctattaccgt tcattagatc cagtgt                               36
```

TUMOR-DELIVERED MULTI-TARGET THERAPEUTICS FOR COLON CANCER

CROSS-REFERENCE TO RELATED APPLICATIONS

This application is a national stage application filed under 35 U.S.C. § 371 of International Application No. PCT/US2020/019112, filed Feb. 20, 2020, which claims the benefit of U.S. Provisional Application No. 62/809,232, filed Feb. 22, 2019, the disclosures of which are hereby incorporated by reference in their entirety for all purposes.

STATEMENT REGARDING FEDERALLY FUNDED RESEARCH OR DEVELOPMENT

Not applicable.

SEQUENCE LISTING

A Sequence Listing accompanies this application and is submitted as an ASCII text file of the sequence listing named "2020-02-17_112624.01168_ST25.txt" which is 79.3 KB in size and was created on Feb. 17, 2020. The sequence listing is electronically submitted via EFS-Web with the application and is incorporated herein by reference in its entirety.

BACKGROUND

Despite many advances in conventional methods such as chemo- and radiation-therapy, cancer treatment is still far from optimal. Current cancer therapies frequently encounter challenges including nonspecific systemic distribution of antitumor agents, inadequate drug concentrations reaching the tumor site, intolerable cytotoxicity and development of multiple drug resistance. Oncolytic bacterial therapy has been extensively studied in recent years to fill the critical unmet needs of cancer patients, where the current treatment options have been exhausted. However, the accumulation of genetic mutations and the potential for acquisition of antibiotic-resistance in the therapeutic bacteria present possible risks for recipients of oncolytic bacterial therapy. Accordingly, there remains a need for improvements to existing oncolytic bacteria-based cancer treatments and, in particular, there is a need to develop new therapeutic methods that achieve precision tumor-navigating and self-eradication of oncolytic *Salmonella* for targeted delivery of decoy binding partners to target multiple cancer cell-surface receptors and cancer cell-released factors.

SUMMARY OF THE DISCLOSURE

The present disclosure addresses the aforementioned drawbacks of conventional methods for treating cancer.

In a first aspect, provided herein is a genetically modified *Salmonella* bacterium comprising, or consisting essentially of, (i) a recombinant gene encoding a human decoy polypeptide; (ii) the following mutations $\Delta P_{murA}$::TT araC $P_{BAD}$ murA $\Delta$asd::TT araC $P_{BAD}$ c2 $\Delta$(araC $P_{BAD}$)::P22 $P_R$ araBAD $\Delta$(wza-wcaM) $\Delta$pmi $\Delta$relA::araC $P_{BAD}$ lacI TT $\Delta$pagP::$P_{lpp}$ lpxE $\Delta$endA; and (iii) one or more of mutations selected from $\Delta P_{tar}$::$P_{trc\ \Delta lacO}$ tar, $\Delta P_{tsr}$::$P_{trc\ \Delta lacO}$ tsr, and $\Delta$trg. The decoy polypeptide can disrupt Wnt/β-catenin signaling. The decoy polypeptide can be selected from a soluble form of human frizzled (FZD) receptor, a soluble form of human LRP6, a soluble form of human PD-1, and a soluble form of human SIRP-alpha. The bacterium can comprise mutation $\Delta P_{tar}$::$P_{trc\ \Delta lacO}$ tar. The bacterium can comprise mutations $\Delta P_{tar}$::$P_{trc\ \Delta lacO}$ tar, $\Delta P_{tsr}$::$P_{trc\ \Delta lacO}$ tsr, and $\Delta$trg. The bacterium can be a *Salmonella* strain selected from GMS515(pK-FZD), GMS515(pK-LRP6), GMS515 (pK-PD-1), GMS515(pK-SIRPα), GMS515(pK-VEGFR2), GMS515(pK-PDGFRα), and GMS515(pK-FGFR-1).

In another aspect, provided herein is a genetically modified *Salmonella* bacterium comprising, or consisting essentially of, (i) a recombinant gene encoding a human decoy polypeptide; (ii) the following mutations $\Delta P_{murA}$::TT araC $P_{BAD}$ murA $\Delta$asdA::TT araC $P_{BAD}$ c2 $\Delta$(wza-wcaM) $\Delta$pmi $\Delta$relA $\Delta$recF $\Delta$sifA $\Delta$endA $\Delta$sseL $\Delta$tlpA $\Delta P_{hilA}$::$P_{trc\ \Delta lacO888}$hilA; and (iii) one or more of mutations selected from $\Delta P_{tar}$::$P_{trc\ \Delta lacO}$ tar, $\Delta P_{tsr}$::$P_{trc\ \Delta lacO}$ tsr, and $\Delta$trg. The decoy polypeptide can disrupt Wnt/β-catenin signaling. The decoy polypeptide can be selected from a soluble form of human frizzled (FZD) receptor, a soluble form of human LRP6, a soluble form of human PD-1, and a soluble form of human SIRP-alpha. The bacterium can comprise mutation $\Delta P_{tar}$::$P_{trc\ \Delta lacO}$ tar. The bacterium can comprise mutations $\Delta P_{tar}$::$P_{trc\ \Delta lacO}$ tar, $\Delta P_{tsr}$::$P_{trc\ \Delta lacO}$ tsr, and $\Delta$trg. The bacterium can be a *Salmonella* strain selected from GMS525(pK-DFZD), GMS525(pK-DLRP6), GMS525(pK-DPD-1), and GMS525(pK-DSIRPa).

In another aspect, provided herein is a method of treating a tumor in a subject in need thereof comprising administering a genetically modified *Salmonella* bacterium of this disclosure to the subject, whereby the genetically modified *Salmonella* bacterium treats tumor cells in the subject. Administering can comprise oral administration or intra-tumoral injection of the genetically modified *Salmonella* bacterium.

In a further aspect, provided herein is a method for stimulating tumoricidal activity in a host comprising, or consisting essentially of, transforming a first recombinant gene into a strain of *Salmonella* forming a strain B, the first recombinant gene encoding a decoy polypeptide; introducing the following mutations $\Delta P_{murA}$::TT araC $P_{BAD}$ murA $\Delta$asd::TT araC $P_{BAD}$ c2 $\Delta$(araC $P_{BAD}$)::P22 $P_R$ araBAD $\Delta$(wza-wcaM) $\Delta$pmi $\Delta$relA::araC $P_{BAD}$ lacI TT $\Delta$pagP::$P_{lpp}$ lpxE $\Delta$endA into strain B, thereby forming strain C; introducing one or more mutations selected from $\Delta P_{tar}$::$P_{trc\ \Delta lacO}$ tar, $\Delta P_{tsr}$::$P_{trc\ \Delta lacO}$ tsr, and $\Delta$trg into strain C, thereby forming strain D; and administering strain D to the host. The decoy polypeptide can disrupt Wnt/β-catenin signaling. The decoy polypeptide can be selected from a soluble form of human frizzled (FZD) receptor, a soluble form of human LRP6, a soluble form of human PD-1, and a soluble form of human SIRP-alpha. Administering can comprise oral administration or intra-tumoral injection of strain D into the host. Strain D can be a *Salmonella* strain selected from GMS515 (pK-FZD), GMS515(pK-LRP6), GMS515(pK-PD-1), GMS515(pK-SIRPα), GMS515(pK-VEGFR2), GMS515 (pK-PDGFRα), and GMS515(pK-FGFR-1).

In another aspect, provided herein is a method for stimulating tumoricidal activity in a host comprising, or consisting essentially of, introducing the following mutations $\Delta P_{murA}$::TT araC $P_{BAD}$ murA $\Delta$asdA::TT araC $P_{BAD}$ c2 $\Delta$(wza-wcaM) $\Delta$pmi $\Delta$relA $\Delta$recF $\Delta$sifA $\Delta$endA $\Delta$sseL $\Delta$tlpA $\Delta P_{hilA}$::$P_{trc\ \Delta lacO888}$hilA into a strain of *Salmonella*, whereby strain E is formed; introducing one or more mutations selected from $\Delta P_{tar}$::$P_{trc\ \Delta lacO}$ tar, $\Delta P_{tsr}$::$P_{trc\ \Delta lacO}$ tsr, and $\Delta$trg into strain E, whereby strain F is formed; transforming a recombinant gene into strain F, the recombinant gene encoding a decoy polypeptide; whereby strain G is formed; and administering strain G to the host. The decoy polypeptide can disrupt Wnt/β-catenin signaling. The decoy polypeptide can be selected from a soluble form of human frizzled (FZD) receptor, a soluble form of human LRP6, a soluble form of human PD-1, and a soluble form of human SIRP-alpha. Administering can comprise oral administration or intra-tumoral injection of strain G into the host. Strain G can be a *Salmonella* strain selected from GMS525(pK-DFZD), GMS525(pK-DLRP6), GMS525(pK-DPD-1), and GMS525(pK-DSIRPa).

These and other advantages and features of the present disclosure will become more apparent from the following detailed description of the preferred embodiments of the present disclosure when viewed in conjunction with the accompanying drawings.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 8 demonstrates that reprogrammed GMS strains promoted cancer cell-killing in a transgenic colon tumor mouse model. The representative *Salmonella* staining (left, dark brown) in polypus from colons and rectums of t-APC mice treated with PBS or GMS strains, as indicated. TUNEL staining (right, green).

DETAILED DESCRIPTION

Figure 1:
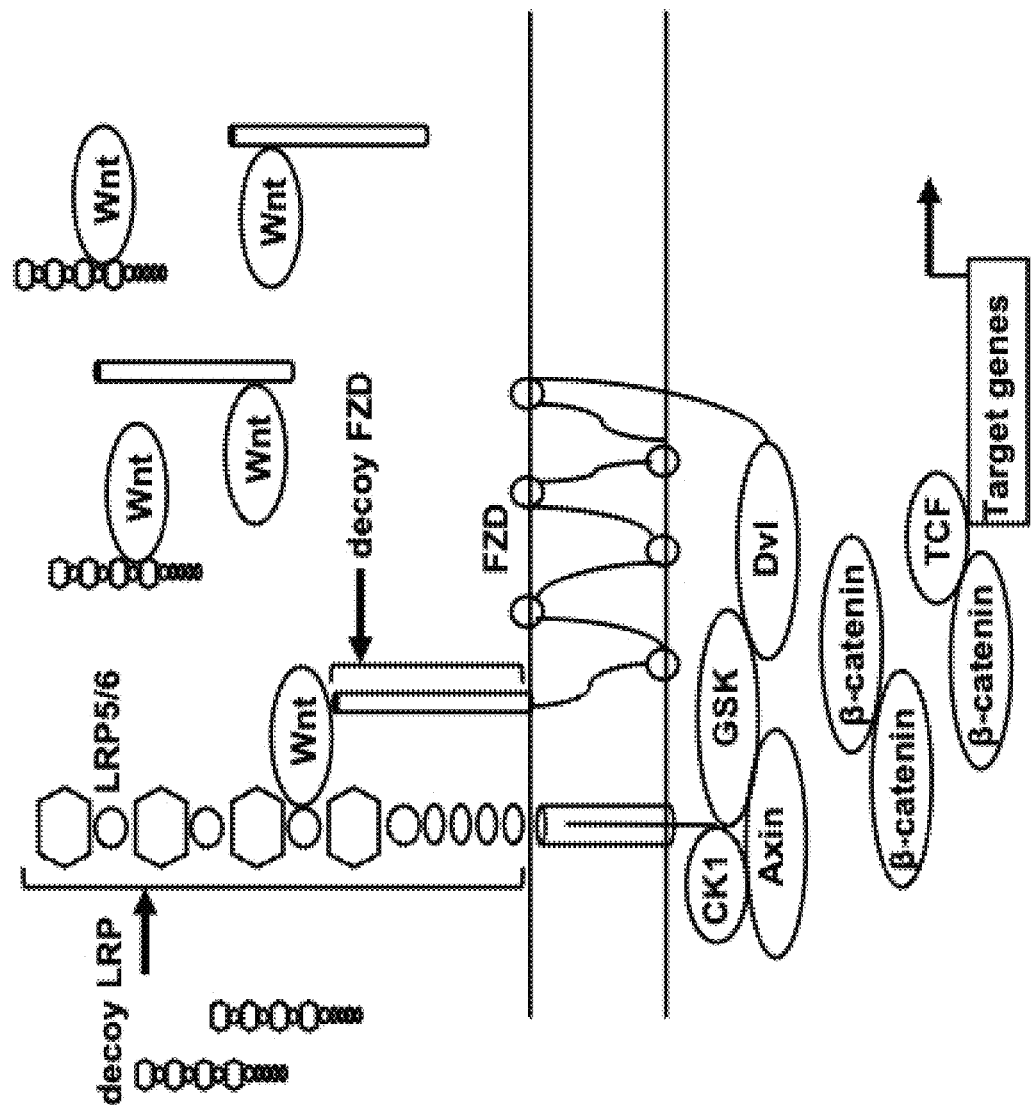
FIG. 1 illustrates the disruption of the Wnt/β-catenin pathway by decoy FZD and decoy LRP5/6.

The present disclosure addresses the aforementioned drawbacks of conventional methods for treating cancer, including current uses of oncolytic bacteria in cancer treatments. In particular, the methods and compositions described herein are based at least in part on the inventor's development of GMS capable of precise navigation to tumors and self-eradication, and armed with decoy peptides that disrupt signal transduction cascades within the tumor microenvironment. The present disclosure provides GMS-based therapeutic strategies for treating cancer based on the ability of tumor-navigating, self-eradicating GMS strains to deliver decoy peptides that disrupt signal transduction cascades within the tumor microenvironment. Without being bound to any particular mode of action or theory, the GMS-based cancer therapeutic strategies of this disclosure are based on the ability of tumor-navigating, self-eradicating GMS strains to deliver decoy receptors to disrupt the Wnt/β-catenin pathway, to disrupt interaction of PD-L1 and PD-1, to increase macrophage-mediated tumor cell phagocytosis, and to suppress tumor angiogenesis.

Accordingly, in a first aspect, provided herein is a genetically modified *Salmonella* bacterium, where the bacterium comprises a recombinant gene encoding a decoy polypeptide. Also provided herein is a genetically modified *Salmonella* bacterium, where the bacterium comprises a recombinant gene encoding for increased expression of a methyl-accepting chemotaxis protein (MCP). Also provided herein is a genetically modified *Salmonella* bacterium, where the bacterium comprises a recombinant gene encoding for reduced toxicity of the bacterium in a plurality of non-tumor cells and for toxicity of the bacterium in tumor cells.

In some cases, the genetically modified *Salmonella* bacterium comprises a first recombinant gene encoding a decoy peptide, a second recombinant gene encoding for increased expression of a methyl-accepting chemotaxis protein (MCP), and a third recombinant gene encoding for reduced toxicity of the bacterium in a plurality of non-tumor cells and for toxicity of the bacterium in tumor cells. Such genetically modified *Salmonella* bacteria are capable of self-eradication and specific delivery of decoy peptides to tumor cells. Such GMS also exhibit increased chemotaxis to tumor cells and increased tumoricidal activity relative to a *Salmonella* bacterium not comprising the first recombinant gene. Lysis of the genetically modified *Salmonella* of this disclosure releases GMS-expressed decoy peptides, thereby disrupting molecular interactions in targeted signaling cascades within the tumor microenvironment.

Some embodiments of the instant disclosure comprise a species or subspecies of the *Salmonella* genera. For instance, the recombinant bacterium may be a *Salmonella enterica* serovar. In an exemplary embodiment, a bacterium of the disclosure may be derived from (i.e., an isolate of) *S. enterica* serovar Typhimurium, referred to herein as *Salmonella* Typhimurium, and also from *S*. Typhi, *S*. Paratyphi, *S*.

Enteritidis, S. Choleraesius, S. Arizona, or S. Dublin. In an exemplary embodiment, the recombinant bacterium is derived from S. Typhimurium. As used herein, "Salmonella Typhimurium" refers to an isolate of Salmonella Typhimurium. Likewise, the terms "S. Typhi," "S. Paratyphi," "S. Enteritidis," "S. Choleraesius," "S. Arizona," and "S. Dublin" as used herein refer to isolates of Salmonella Typhi, S. Paratyphi, S. Enteritidis, S. Choleraesius, S. Arizona, and S. Dublin, respectively. As used herein the terms "strain" and "isolate" are used interchangeably.

As used herein, the term "decoy polypeptide" refers to a polypeptide or fragment thereof that is capable of trapping the ligands of a target molecule (e.g., a cell surface receptor) and thus preventing its activation. Preferably, decoy polypeptides are soluble forms of a target protein. In some cases, a decoy polypeptide is a truncated form of the target protein from which the transmembrane domain has been removed by chemical, proteolytic, or recombinant methods.

In some cases, the decoy polypeptide is a polypeptide or fragment thereof that disrupts the Wnt/β-catenin pathway and, consequently, reduces or stops Wnt-regulated gene expression. Contemplated within the scope of embodiments presented herein are variants of Wnt-binding receptor polypeptides that act as decoys for canonical Wnt ligands and block Wnt/β-catenin-mediated signaling. In some cases, the decoy polypeptide comprises all or a portion of the extracellular, Wnt-binding domain of a Frizzled (FZD) receptor. For example, as illustrated in FIG. 1, the decoy polypeptide may comprise a human FZD polypeptide, where the polypeptide comprises at least one amino acid modification to increase the affinity of the decoy FZD polypeptide binding to a canonical Wnt ligand as compared to the affinity for Wnts of the corresponding wild-type FZD receptor.

In some cases, the decoy polypeptide comprises all or a portion of the extracellular Wnt binding domain of LRP6. For example, as illustrated in FIG. 1, the decoy polypeptide may comprise a human LRP6 polypeptide, where the polypeptide comprises at least one amino acid modification to increase the affinity of the decoy LRP6 polypeptide binding to a canonical Wnt ligand as compared to the affinity for Wnts of the corresponding wild-type LRP6 receptor.

Figures 2A, 2B:
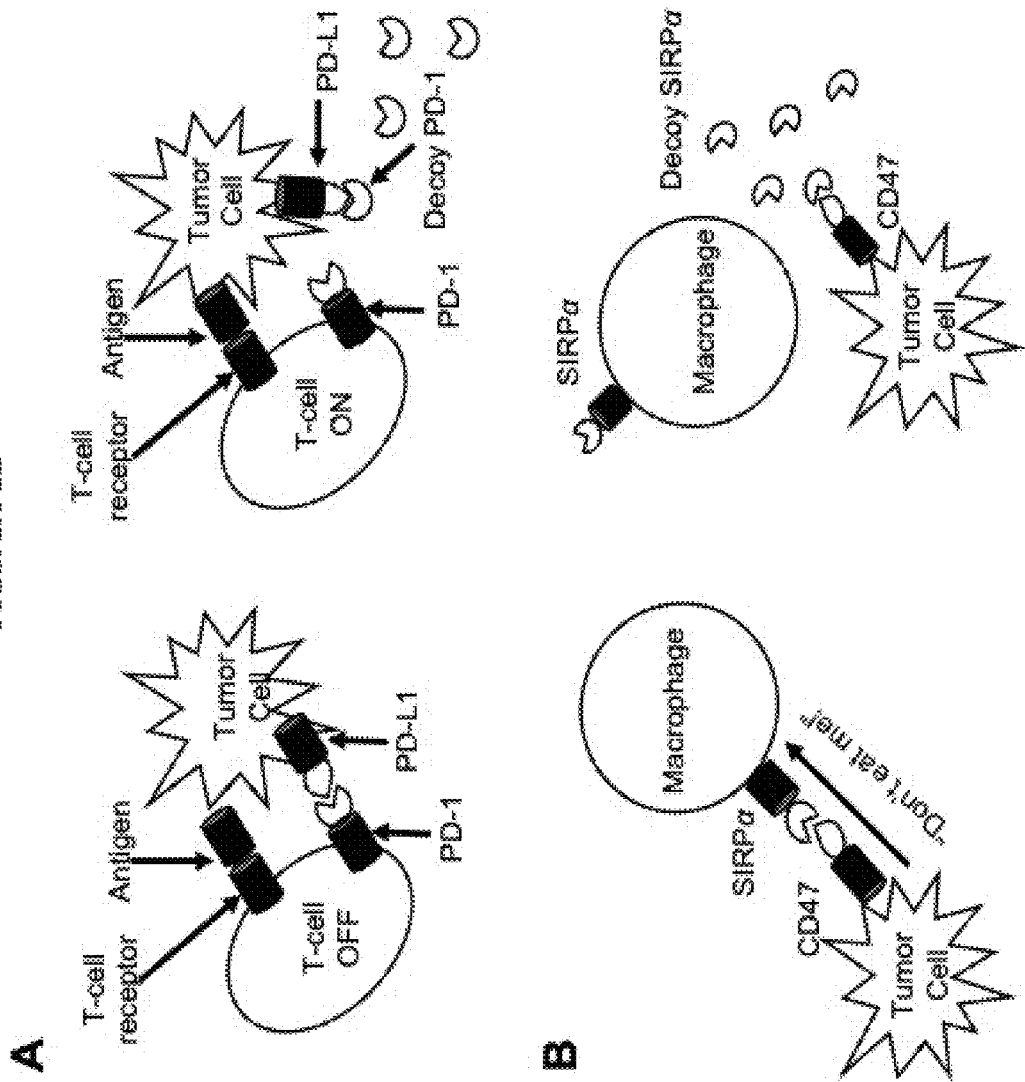
FIGS. 2A-2B illustrate (A) interference of the PD-1/PD-L1 interaction by decoy PD-1 receptor and (B) blockage of CD47 by decoy SIRPα.

In some cases, the decoy polypeptide is a polypeptide or fragment thereof that blocks molecular interactions between Programmed Cell Death Protein 1 (PD-1) and its ligands, PD-L1 and PD-L2. In some cases, the decoy polypeptide comprises all or a portion of the extracellular ligand-binding domain of a PD-1 receptor. In some cases, the decoy polypeptide is soluble extracellular domain of programmed cell death protein 1 (PD-1) tumor, which serves as a decoy PD-1 receptor to interfere PD-1 and programmed death-ligand 1 (PD-L1) interaction. Without being bound by any particular theory or mode of action, it is believed that expression of a decoy PD-1 receptor reverses T-cell exhaustion and reinvigorating antitumor activity within the tumor microenvironment (see FIG. 2A).

In some cases, the decoy polypeptide is a polypeptide or fragment thereof that blocks binding of Cluster of Differentiation 47 (CD47) to its ligand, thereby activating macrophage-mediated tumor cell phagocytosis. CD47 ligands include SIRP-alpha, SIRP-gamma, and thrombospondin-1. Contemplated within the scope of embodiments presented herein are variants of SIRP-alpha polypeptides that act as decoys for CD47 and activate phagocytosis. In some embodiments, a decoy polypeptide comprises a SIRP-alpha polypeptide, wherein the polypeptide comprises at least one amino acid modification to increase affinity of the decoy SIRP-alpha polypeptide binding to CD47 as compared to the affinity for CD47 of the corresponding wild type SIRP-alpha polypeptide. Without being bound by any particular theory or mode of action, it is believed that expression of a decoy SIRP-alpha polypeptide interferes with the CD47-STRPα axis signaling pathway to enhance macrophages-mediated tumor cell phagocytosis within the tumor microenvironment (see FIG. 2B).

In some cases, a genetically modified Salmonella bacterium of this disclosure is a GMS strain presented in Table 1.

TABLE 1

GMS-based therapeutics

| Strain name; plasmid sequence | Description | Peptide synthesized |
|---|---|---|
| GMS515(pK-FZD); SEQ ID NO: 1 | Wnt pathway-targeting | pYA3681 encoding codon-optimized human Wnt binding domains of FZD |
| GMS515(pK-LRP6); SEQ ID NO: 3 | Wnt pathway-targeting | pYA3681 encoding codon-optimized human Wnt binding domains of LRP6 |
| GMS515(pK-PD-1); SEQ ID NO: 5 | PD-L1-blocking | pYA3681 encoding codon-optimized extracellular domain of human PD-1 |
| GMS515(pK-SIRPα); SEQ ID NO: 7 | Macrophage phagocytosis enhancing | pYA3681 encoding codon-optimized extracellular domain of human SIRPα |
| GMS515(pYA3681) | empty vector control | none |
| GMS515(pK5079) | current death receptor-targeting | pYA3681 encoding human TRAIL (not codon optimized) |
| GMS525(pK-DFZD); SEQ ID NO: 2 | Wnt pathway-targeting | pYA4545 encoding human Wnt binding domains of FZD |
| GMS525(pK-DLRP6); SEQ ID NO: 4 | Wnt pathway-targeting | pYA4545 encoding human Wnt binding domains of LRP6 |
| GMS525(pK-DPD-1); SEQ ID NO: 6 | PD-L1-blocking | pYA4545 encoding extracellular domain of human PD-1 |
| GMS525(pK-DSIRPα); SEQ ID NO: 8 | Macrophage phagocytosis enhancing | pYA4545 encoding extracellular domain of human SIRPα |
| GMS525(pYA4545) | empty vector control | none |

To produce decoy polypeptides, DNA sequences may be codon-optimized for expression in Salmonella and synthesized in vitro. In some cases, codon-optimized human DNA fragments can be inserted into lysis vector and DNA vaccine vector (e.g., pYA3681 and pYA4545), and then transformed into tumor-navigating strains (e.g., GMS515 and GMS525). In some cases, the resulting strains are those in Table 1.

As used herein, the terms "genetically modified" and "genetically engineered" are used interchangeably and refer to a prokaryotic cell that includes an exogenous polynucleotide, regardless of the method used for insertion. In some cases, the cell has been modified to comprise a non-naturally occurring nucleic acid molecule that has been created or modified by the hand of man (e.g., using recombinant DNA technology) or is derived from such a molecule (e.g., by transcription, translation, etc.). A cell that contains an exogenous, recombinant, synthetic, and/or otherwise modified polynucleotide is considered to be an engineered cell. The term "altered," as used herein, refers to any change in the nucleic acid sequence that results in the nucleic acid sequence not being expressed. In an exemplary embodiment, the alteration results in the nucleic acid sequence not being expressed in a host. In one embodiment, the alteration is a deletion. In another embodiment, the alteration places an essential nucleic acid under the control of a regulatable promoter, such that the nucleic acid is not expressed in a host.

In addition to the introduction of recombinant genes encoding decoy polypeptides as described above, *Salmonella* are also genetically modified to increase navigation of the bacteria to cancer cells (tumor cells) by modulating the expression of MCP, which are transmembrane chemoreceptors important for taxis (bacterial movement) toward or away from particular substrates. *Salmonella* MCPs include Tar (taxis towards aspartate and maltose, away from nickel and cobalt; aka cheM), Tsr (taxis towards serine, away from leucine, indole and weak acids), Trg (taxis towards sugars, galactose and ribose), Tap (taxis towards dipeptides), McpC (repellent response towards L-cystine), Tip, McpA, and McpB. The coding sequence of Tsr (Methyl-accepting chemotaxis protein) of *Salmonella* typhimurium is accession number A0A0H3NL96. The coding sequence of Tar (Methyl-accepting chemotaxis protein II) of *S. typhimurium* is accession number P02941.

In some cases, GMS of this disclosure are engineered for increased chemotaxis toward tumor cells by increasing expression of tar and/or increasing expression of tsr. In some cases, genetic modification further comprises reducing expression of trg. For example, a bacterium can be genetically altered to produce modified *Salmonella* having constitutive over-expression of one or more chemoreceptors such as Tar and Tsr. In some cases, a genetically modified *Salmonella* bacterium comprises mutation $\Delta P_{tar}::P_{trc\ \Delta lacO}$ tar. In other cases, the genetically modified *Salmonella* bacterium comprises mutations $\Delta P_{tar}::P_{trc\ \Delta lacO}$ tar, $\Delta P_{tsr}::P_{trc\ \Delta lacO}$ tsr, and $\Delta$trg. In some cases, the genetically modified *Salmonella* bacterium is from strain GMS410 (pK5079) or GMS515(pK5079). Such strains include self-eradication vectors, TRAIL, and MCP mutations described herein for increased chemotaxis to tumor cells.

In some cases, a genetically modified *Salmonella* bacterium comprises: (i) a recombinant gene encoding a human decoy polypeptide; (ii) the following mutations $\Delta P_{murA}$::TT araC $P_{BAD}$ murA $\Delta$asd::TT araC $P_{BAD}$ c2 $\Delta$(araC $P_{BAD}$)::P22 $P_R$ araBAD $\Delta$(wza-wcaM) $\Delta$pmi $\Delta$relA::araC $P_{BAD}$ lacI TT $\Delta$pagP::$P_{lpp}$ lpxE $\Delta$endA; and (iii) one or more of mutations selected from $\Delta P_{tar}::P_{trc\ \Delta lacO}$ tar, $\Delta P_{tsr}::P_{trc\ \Delta lacO}$ tsr, and $\Delta$trg. In some cases, the genetically modified bacterium is a *Salmonella* strain such as GMS515(pK-FZD), GMS515(pK-LRP6), GMS515(pK-PD-1), GMS515(pK-SIRPα), GMS515(pK-VEGFR2), GMS515(pK-PDGFRα), or GMS515(pK-FGFR-1).

In some cases, a genetically modified *Salmonella* bacterium comprises: (i) a recombinant gene encoding a human decoy polypeptide; (ii) the following mutations $\Delta P_{murA}$::TT araC $P_{BAD}$ murA $\Delta$asdA::TT araC $P_{BAD}$ c2 $\Delta$(wza-wcaM) $\Delta$pmi $\Delta$relA $\Delta$recF $\Delta$sifA $\Delta$endA $\Delta$sseL $\Delta$tlpA $\Delta P_{hilA}::P_{trc\ \Delta lacO888}$hilA; and (iii) one or more of mutations selected from $\Delta P_{tar}::P_{trc\ \Delta lacO}$ tar, $\Delta P_{tsr}::P_{trc\ \Delta lacO}$ tsr, and $\Delta$trg. In some cases, the genetically modified *Salmonella* bacterium is a *Salmonella* strain such as GMS525(pK-DFZD), GMS525(pK-DLRP6), GMS525(pK-DPD-1), or GMS525(pK-DSIRPa).

The "$\Delta$" as used herein, refers to gene deletion; The "::" as used herein, refers to gene insertion; The "asdA" as used herein, refers to a gene encoding aspartate-semialdehyde dehydrogenase. The asdA mutants of Gram-negative bacteria have an obligate requirement for diaminopimelic acid (DAP), which is an essential constituent of the peptidoglycan layer of the cell wall of these organisms. The "murA" refers to a gene required for the synthesis of the peptidoglycan layer of the bacterial cell wall. Like asdA mutants, murA mutants ("$\Delta$murA") are deficient in bacterial cell wall synthesis.

In another aspect, provided herein are methods for producing genetically modified *Salmonella* bacteria having increased tumoricidal activity. In exemplary embodiments, the method comprises: introducing one or more mutations into a first strain of *Salmonella*, whereby strain B is formed and exhibits (i) reduced toxicity in a non-tumor cell relative to a *Salmonella* control strain that does not comprise the one or more mutations; and (ii) increased toxicity in a tumor cell relative to a *Salmonella* control strain that does not comprise the one or more mutations. The mutations can be introduced as a first recombinant nucleic acid.

In some cases, a second recombinant gene is introduced into strain B, thus forming strain C, where the second recombinant gene encodes a protein that promotes chemotaxis of the strain C toward a plurality of tumor cells. In some cases, the second recombinant gene encodes for the synthesis of Tar or synthesis of Tsr.

In some cases, a third recombinant gene is introduced into strain C, thus forming strain D, where the third recombinant gene encodes a decoy polypeptide. Preferably, the third recombinant gene encodes a decoy polypeptide. In some cases, the third recombinant gene is introduced in a lysis vector. In other cases, the third recombinant gene is introduced in a DNA vaccine vector. In some cases, strain D comprises mutation $\Delta P_{tar}::P_{trc\ \Delta lacO}$ tar, or comprises mutations $\Delta P_{tar}::P_{trc\ \Delta lacO}$ tar, $\Delta P_{tsr}::P_{trc\ \Delta lacO}$ tsr, and $\Delta$trg. In some cases, strain D is a strain in Table 1.

In certain embodiments, a genetically modified bacterium of the disclosure may also be attenuated. As used herein, the term "attenuated" refers to the state of the bacterium wherein the bacterium has been weakened from its wild-type fitness by some form of recombinant or physical manipulation such that the bacterium's virulence is reduced relative to a control (a non-recombinant/non-manipulated bacterium). This includes altering the genotype of the bacterium to reduce its ability to cause disease. However, the bacterium's ability to colonize the tumor is, preferably, not substantially compromised. For instance, in one embodiment, regulated attenuation allows the recombinant bacterium to express one or more nucleic acids encoding products important for the bacterium to withstand stresses encountered in the host after immunization. This allows efficient invasion and colonization of tumor tissues before the genetically modified bacterium is regulated to display the attenuated phenotype. As used herein in this context, the term "reduce/reduced" means a reduction of at least 10%, preferably 25%, even more preferably 50%, still more preferably 60%, even more preferably 70%, still more preferably 80%, even more preferably 90% and most preferably of 100% as compared to the appropriate control.

The genetically modified *Salmonella* described herein can be used in a variety of applications. For example, the genetically modified *Salmonella* can be used in therapeutic methods to treat cancer or a cancer-associated condition. In some cases, a method of treating cancer in a subject in need thereof will comprise administering an effective amount of a modified *Salmonella* bacterium having the genetic modifications described herein and, thus, being tumor navigating, self-eradicating, and armed with one or more decoy polypeptides, to the subject, whereby the genetically modified *Salmonella* bacterium treats cancer in the subject.

As used herein, the term "effective amount" means, in the context of a composition, an amount of an immunogenic composition capable of inducing an immune response that reduces the incidence of or lessens the severity of infection or incident of disease in an animal. Alternatively, in the context of a therapy, the term "effective amount" refers to the amount of a therapy which is sufficient to reduce or ameliorate the severity or duration of a disease or disorder (e.g., cancer), or one or more symptoms thereof, prevent the advancement of a disease or disorder, cause the regression of a disease or disorder, prevent the recurrence, development, onset, or progression of one or more symptoms associated with a disease or disorder, or enhance or improve the prophylaxis or treatment of another therapy or therapeutic agent. The effective amount to be administered will depend upon the host receiving the modified bacteria as well as factors such as the size, weight, and age of the host.

As used herein, "subject" refers to an animal or a patient for whom the described treatment is intended. In exemplary embodiments, subjects treated according to the methods provided herein are human. In other cases, subjects treated according to the methods provided herein are non-human mammals, including by way of example and not limitation, members of rodentia (e.g., mouse, rat, guinea pig), lagomorpha (e.g., rabbits, hares), perissodactyla (e.g., horses, donkeys, etc.), artodactyla (e.g., pigs, cows, sheep), carnivora (e.g., cats, canines), and primates (e.g., apes, monkeys, baboons, and humans).

As used herein, the terms "treat" and "treating" refer to both therapeutic treatment and prophylactic or preventative measures, wherein the object is to treat, rescue, ameliorate, or otherwise lessen an undesired symptom or condition associated with cancer or any condition associated with aberrant cell proliferation. In some cases, the term "treated" refers to any beneficial effect on the progression of a disease or condition. Beneficial effects can include reversing, alleviating, inhibiting the progress of, preventing, or reducing the likelihood of the disease or condition to which the term applies or one or more symptoms or manifestations of such a disease or condition. Where the disease or condition is cancer or a cancer-associated condition, treating can refer to the management and care of a patient for the purpose of combating cancer, and can include reversing, alleviating, inhibiting the progress of, preventing, or reducing the likelihood of, or lessening the severity of any aspect of the cancer or cancer-associated condition (e.g., metastasis, tumor growth). As used herein, the terms "preventing" and "prevent" refer not only to a complete prevention of a certain disease or condition, but also to partially or substantially attenuating, reducing the risk of, or delaying the development or recurrence of the disease or condition to which the term applies.

In some cases, the methods provided herein are directed to treating or preventing a cancer in a subject by administering a composition provided herein. In other cases, the present disclosure provides a method of inhibiting, retarding, or preventing the growth of a tumor or tumor cells in a subject. In exemplary embodiments, colon cancer (colorectal cancer) is treated using the methods provided herein. Examples of other cancers appropriate for methods of treating or preventing as provided herein include, without limitation, lung cancer, pancreatic cancer, prostate cancer, skin cancer, bladder cancer, kidney cancer, ovarian cancer, colorectal cancer, breast cancer, cervical cancer, brain cancer, esophageal cancer, and stomach cancer. Other diseases or conditions appropriate for methods of treating or preventing as provided herein include, without limitation, lymphoma and chronic and acute leukemia.

Any appropriate route or mode of administration to the subject can be employed according to a method provided herein. In some cases, administering comprises oral administration of the genetically modified *Salmonella* bacterium. In other cases, administering comprises intra-tumoral injection of the genetically modified *Salmonella* bacterium. The mode of administration can be determined based on the physical location, type, or the number of tumors in the subject's body.

Clinicians, physicians, and other health care professionals can administer genetically modified *Salmonella* bacteria to a subject in need thereof according to a method provided herein. In some cases, a single administration of the composition may be sufficient. In other cases, more than one administration of the composition is performed at various intervals (e.g., once per week, twice per week, daily, monthly) or according to any other appropriate treatment regimen. The duration of treatment can be a single dose or periodic multiple doses for as long as the administration of a composition provided herein is tolerated by the subject.

Any appropriate method can be practiced to determine, detect, or monitor a subject's response to treatment according to a method provided herein. As used herein, "determining a subject's response to treatment" refers to the assessment of the results of a therapy in a subject in response to administration of a composition provided herein or to treatment according to a method provided herein. For example, a subject's condition can be monitored continuously or evaluated at appropriate time intervals (e.g., at regular or irregular time points) to detect and/or monitor any changes in disease progression (e.g., change in tumor size) as an indicator of the subject's response to a composition comprising genetically modified *Salmonella* bacteria as described herein. In some cases, tumors can be measured to detect or monitor any change in, for example, tumor size or tumor growth rate (e.g., tumor expansion or shrinkage, inhibited or accelerated tumor growth rate). For example, detection methods such as computed tomography (CT), magnetic resonance imaging (MRI) scanning, and x-ray (e.g., chest x-ray) can be used. In some cases, ultrasound examinations can be used to detect and measure tumor regression or to detect the progression of lesions. In other cases, evaluation of a tumor can involve cytology or histology of, for example, biopsy samples. For solid tumors, evaluation of a subject's response to treatment as provided herein can include assessing RECIST ("Response Evaluation Criteria in Solid Tumors"). RECIST criteria can be used to evaluate a subject's response to the therapy used to treat their disease or condition. See, for review, Therasse et al., *J. Natl. Cancer Inst.* 92:205-16, 2000.

The term "promoter", as used herein, may mean a synthetic or naturally-derived molecule which is capable of conferring, activating or enhancing expression of a nucleic acid in a cell. A promoter may comprise one or more specific transcriptional regulatory sequences to further enhance expression and/or to alter the spatial expression and/or temporal expression of the same.

The terms "nucleic acid" and "nucleic acid molecule," as used herein, refer to a compound comprising a nucleobase and an acidic moiety, e.g., a nucleoside, a nucleotide, or a polymer of nucleotides. Nucleic acids generally refer to polymers comprising nucleotides or nucleotide analogs joined together through backbone linkages such as but not limited to phosphodiester bonds. Nucleic acids include deoxyribonucleic acids (DNA) and ribonucleic acids (RNA) such as messenger RNA (mRNA), transfer RNA (tRNA), etc. Typically, polymeric nucleic acids, e.g., nucleic acid molecules comprising three or more nucleotides are linear molecules, in which adjacent nucleotides are linked to each other via a phosphodiester linkage. In some embodiments, "nucleic acid" refers to individual nucleic acid residues (e.g. nucleotides and/or nucleosides). In some embodiments, "nucleic acid" refers to an oligonucleotide chain comprising three or more individual nucleotide residues. As used herein, the terms "oligonucleotide" and "polynucleotide" can be used interchangeably to refer to a polymer of nucleotides (e.g., a string of at least three nucleotides). In some embodiments, "nucleic acid" encompasses RNA as well as single and/or double-stranded DNA. Nucleic acids may be naturally occurring, for example, in the context of a genome, a transcript, an mRNA, tRNA, rRNA, small interfering RNA (siRNA), small nuclear RNA (snRNA), a plasmid, cosmid, chromosome, chromatid, or other naturally occurring nucleic acid molecules. On the other hand, a nucleic acid molecule may be a non-naturally occurring molecule, e.g., a recombinant DNA or RNA, an artificial chromosome, an engineered genome, or fragment thereof, or a synthetic DNA, RNA, DNA/RNA hybrid, or include non-naturally occurring nucleotides or nucleosides. Furthermore, the terms "nucleic acid," "DNA," "RNA," and/or similar terms include nucleic acid analogs, i.e. analogs having other than a phosphodiester backbone. Nucleic acids can be purified from natural sources, produced using recombinant expression systems and optionally purified, chemically synthesized, etc. Where appropriate, e.g., in the case of chemically synthesized molecules, nucleic acids can comprise nucleoside analogs such as analogs having chemically modified bases or sugars, and backbone modifications. A nucleic acid sequence is presented in the 5' to 3' direction unless otherwise indicated. In some embodiments, a nucleic acid is or comprises natural nucleosides (e.g. adenosine, thymidine, guanosine, cytidine, uridine, deoxyadenosine, deoxythymidine, deoxyguanosine, and deoxycytidine); nucleoside analogs (e.g., 2-aminoadenosine, 2-thiothymidine, inosine, pyrrolo-pyrimidine, 3-methyl adenosine, 5-methylcytidine, 2-aminoadenosine, C5-bromouridine, C5-fluorouridine, C5-iodouridine, C5-propynyl-uridine, C5-propynyl-cytidine, C5-methylcytidine, 2-aminoadeno sine, 7-deazaadenosine, 7-deazaguanosine, 8-oxoadenosine, 8-oxoguanosine, 0(6)-methylguanine, and 2-thiocytidine); chemically modified bases; biologically modified bases (e.g., methylated bases); intercalated bases; modified sugars (e.g., 2'-fluororibose, ribose, 2'-deoxyribose, arabinose, and hexose); and/or modified phosphate groups (e.g., phosphorothioates and 5'-N-phosphoramidite linkages).

Nucleic acids and/or other constructs of the disclosure may be isolated. As used herein, "isolated" means to separate from at least some of the components with which it is usually associated whether it is derived from a naturally occurring source or made synthetically, in whole or in part.

The terms "protein," "peptide," and "polypeptide" are used interchangeably herein and refer to a polymer of amino acid residues linked together by peptide (amide) bonds. The terms refer to a protein, peptide, or polypeptide of any size, structure, or function. Typically, a protein, peptide, or polypeptide will be at least three amino acids long. A protein, peptide, or polypeptide may refer to an individual protein or a collection of proteins. One or more of the amino acids in a protein, peptide, or polypeptide may be modified, for example, by the addition of a chemical entity such as a carbohydrate group, a hydroxyl group, a phosphate group, a farnesyl group, an isofarnesyl group, a fatty acid group, a linker for conjugation, functionalization, or other modification, etc. A protein, peptide, or polypeptide may also be a single molecule or may be a multi-molecular complex. A protein, peptide, or polypeptide may be just a fragment of a naturally occurring protein or peptide. A protein, peptide, or polypeptide may be naturally occurring, recombinant, or synthetic, or any combination thereof. A protein may comprise different domains, for example, a nucleic acid binding domain and a nucleic acid cleavage domain. In some embodiments, a protein comprises a proteinaceous part, e.g., an amino acid sequence constituting a nucleic acid binding domain.

Nucleic acids, proteins, and/or other moieties of the disclosure may be purified. As used herein, purified means separate from the majority of other compounds or entities. A compound or moiety may be partially purified or substantially purified. Purity may be denoted by weight measure and may be determined using a variety of analytical techniques such as but not limited to mass spectrometry, HPLC, etc.

In interpreting this disclosure, all terms should be interpreted in the broadest possible manner consistent with the context. It is understood that certain adaptations of the disclosure described in this disclosure are a matter of routine optimization for those skilled in the art, and can be implemented without departing from the spirit of the disclosure, or the scope of the appended claims.

So that the compositions and methods provided herein may more readily be understood, certain terms are defined:

As used in this specification and the appended claims, the singular forms "a," "an," and "the" include plural references unless the context clearly dictates otherwise. Any reference to "or" herein is intended to encompass "and/or" unless otherwise stated.

The terms "comprising", "comprises" and "comprised of" as used herein are synonymous with "including", "includes" or "containing", "contains", and are inclusive or open-ended and do not exclude additional, non-recited members, elements, or method steps. The phraseology and terminology used herein is for the purpose of description and should not be regarded as limiting. The use of "including," "comprising," "having," "containing," "involving," and variations thereof, is meant to encompass the items listed thereafter and additional items. Embodiments referenced as "comprising" certain elements are also contemplated as "consisting essentially of" and "consisting of" those elements. Use of ordinal terms such as "first," "second," "third," etc., in the claims to modify a claim element does not by itself connote any priority, precedence, or order of one claim element over another or the temporal order in which acts of a method are performed. Ordinal terms are used merely as labels to distinguish one claim element having a certain name from another element having the same name (but for the use of the ordinal term), to distinguish the claim elements.

The terms "about" and "approximately" shall generally mean an acceptable degree of error for the quantity measured given the nature or precision of the measurements. Typical, exemplary degrees of error are within 10%, and preferably within 5% of a given value or range of values. Alternatively, and particularly in biological systems, the terms "about" and "approximately" may mean values that are within an order of magnitude, preferably within 5-fold and more preferably within 2-fold of a given value. Numerical quantities given herein are approximate unless stated otherwise, meaning that the term "about" or "approximately" can be inferred when not expressly stated.

Unless otherwise defined, all technical terms used herein have the same meaning as commonly understood by one of ordinary skill in the art to which this disclosure belongs. As used herein and in the claims, the singular forms "a," "an,"

and "the" include the singular and the plural reference unless the context clearly indicates otherwise. Thus, for example, a reference to "an agent" includes a single agent and a plurality of such agents. Any reference to "or" herein is intended to encompass "and/or" unless otherwise stated.

Various exemplary embodiments of compositions and methods according to this disclosure in addition to those shown and described herein will become apparent to those skilled in the art from the foregoing description and the following examples and fall within the scope of the appended claims. Those skilled in the art will recognize, or be able to ascertain using no more than routine experimentation, many equivalents to the specific embodiments of the disclosure described herein. Such equivalents are intended to be encompassed by the following claims.

EXAMPLES

The following examples will enable one of skill in the art to more readily understand the principles thereof. The following examples are presented by way of illustration and are not meant to be limiting in any way.

The inventor previously developed a self-destructing *Salmonella* lysis system in which the bacteria are attenuated, yet capable of synthesizing a selected protein or harboring a DNA vaccine, to serve as vaccine delivery platforms against various infectious diseases. The *Salmonella* lysis system contained two components: a lysis *Salmonella* strain and a lysis vector. The *Salmonella* lysis strains harbor a deletion of asdA and the arabinose-regulated expression of murA, two genes required for the synthesis of the peptidoglycan layer of the bacterial cell wall. They also contain additional mutations intended to enhance bacterial cell lysis and antigen or DNA vaccine delivery. The lysis vector cooperatively works with its host *Salmonella* lysis strain to facilitate the arabinose-dependent bacterial cell wall synthesis needed for bacterial reproduction. Upon invasion of host tissues, which is an arabinose-free environment, synthesis of the bacterial cell wall eventually ceases. This leads to bacterial cell lysis to release cell contents after bacteria accumulate in host tissues and accomplish *Salmonella* self-eradicating. Experiments were undertaken to genetically engineer the lysis strains into a versatile set of tumor navigating anti-cancer material delivering vehicles.

Five to six percent of individuals will develop colorectal cancer (CRC) over their lifetime in the United States. The heavy burden that CRC imposes on our society emphasizes the need to develop effective strategies to prevent and treat this disease. It has been reported that mutations of the adenomatous polyposis coli (APC) gene predispose individuals to familial adenomatous polyposis (FAP), characterized by multiple tumors in the large intestine. Mice carrying a CDX2P-NLS-Cre recombinase transgene and a loxP-targeted Apc allele develop mainly colorectal tumors after tamoxifen induction. A transgenic Apc$^{flox/flox}$/CDX2-CRE colon tumor mouse models greatly mimic human FAP-associated colorectal cancer and sporadic colorectal cancer. Moreover, direct orthotopic cell microinjection, between the mucosa and the muscularis externa layers of the cecal wall of immunocompromised NOD. Cg-Prkdcscid Il2rgtm1Wjl/SzJ (NSG™) mice, induces tumor foci in the most relevant metastatic sites observed in humans. The application of this procedure to the human colorectal cancer cell lines HCT-116 yielded high tumor takes and dissemination rates, replicating the metastatic spread to lymph nodes, liver, lung, and peritoneum observed in advanced human colorectal cancer. To faithfully recapitulate human CRC, in addition to allograft and xenograft subcutaneous tumor models, the transgenic and orthotopic colon tumor mouse models were used to evaluate our re-engineered GMS therapeutic strains on inhibition of tumor growth and cancer metastasis.

The *Salmonella* chemotaxis system was engineered to develop tumor navigating, self-eradicating, and TRAIL-armed genetically engineered *Salmonella*. These GMS hold tumor-navigating features and are able to release TRAIL into tumor bed via *Salmonella* cell lysis leading to the induction of tumor cell apoptosis. These GMS were comprehensively evaluated to assure the safety and demonstrate their efficacy on the suppression of cancer growth and metastasis in subcutaneous, orthotopic, and transgenic colon cancer mouse models. These GMS dramatically induced a variety of types of cancer cell death in vitro. Intra-tumor (IT) injected GMS significantly reduced tumor growth in both allograft and xenograft subcutaneous colon cancer mouse models. Moreover, oral administrated (OR), a convenient and less toxic route than parenteral administration, GMS reduced significant tumor growth in the transgenic CRC mouse model and inhibited metastasis in the xenograft orthotopic colon cancer mouse model.

Results

Reprogramming *Salmonella* Chemotaxis System for Tumor-Navigating

We have improved our self-eradicating *Salmonella* strains to better serve the delivery purpose. Lysis strain GMS409 was engineered to not only harbor the genetic attributes for self-eradicating feature, but also to display genetic characteristics for regulated delayed attenuation, delayed antigen synthesis, and reduced endotoxic activity. However, such GMS strain could not target either cancer cells or tumors. To transform a vaccine delivery strain GMS409 into a universal tumor-navigating delivery vehicle for cancer therapy, our approach was to reprogram the *Salmonella* chemotaxis system to enhance its chemotaxis toward particular tumor secreting amino acids. Such a strategy will allow maximized GMS tumor-eradicating and release of an anti-cancer agent inside of the tumor during the self-eradicating process to trigger bacteria-based oncolysis.

In order to achieve this goal, we first replaced the promoters of the genes encoding chemoreceptors Tar (tar) and Tsr (tsr), respectively, with the P$_{trc}$ promoter for constitutive chemoreceptor synthesis. *Salmonella* strains GMS371 carrying single deletion-insertion mutation $\Delta P_{tar}::P_{trc\ \Delta lacO}$ tar and GMS372 harboring single deletion-insertion mutation $\Delta P_{tsr}::P_{trc\ \Delta lacO}$ tsr were created using *Salmonella* wild-type strain χ3761. The constitutive overexpression of chemoreceptors Tar and Tsr in GMS371 and GMS372, respectively, was confirmed by SDS electrophoresis and western blot assay. In addition, strains GMS371 and GMS372 showed similar growth and swimming speed comparing to their wild-type *Salmonella* parent strain χ3761. Chemotaxis assay was performed to demonstrate the ideal enhancement of chemotaxis caused by each deletion-insertion mutation. We found that GMS371 and GMS372 are significantly more attracted to aspartate and serine, respectively, than the wild-type strain χ3761. To further enhance the *Salmonella* accumulation in the layer of tumor quiescent cells, other than the necrotic core, the ribose/galactose receptor trg gene was deleted. The strain with Δtrg deletion is much less attracted to galactose than wild-type strain as desired. To finally create tumor-navigating, self-eradicating GMS strains, which hopefully will be able to efficiently navigate tumor and release cancer-killing material in the tumor bed, the single mutation $\Delta P_{tar}::P_{trc\ \Delta lacO}$ tar or triple mutations $\Delta P_{tar}::P_{trc\ \Delta lacO}$ tar, $\Delta P_{tsr}::P_{trc\ \Delta lacO}$ tsr, and $\Delta$trg were introduced into GMS409 to achieve strains GMS410 and GMS515 (Table 1).

TABLE 2

Primers for Construction of Suicide Vectors

| Name | Sequence |
|---|---|
| pK-FZD | |
| FZD NcoI Primer 1 | CGCCATGGACCACGGCTTCTGC (SEQ ID NO: 9) |
| FZD XmaI Primer 2 | GCCCCGGGCTATTACGGCGCGC (SEQ ID NO: 10) |
| pK-LRP6 | |
| LRP6P NcoI Primer 1 | CGCCATGGGCATCGTACCCGAA (SEQ ID NO: 11) |
| LRP6P XmaI Primer 2 | CCCCGGGCTATTAGCATGACAA (SEQ ID NO: 12) |
| pK-PD-1 | |
| PD1 NcoI Primer 1 | CGCCATGGGCTTAGACTCCCCA (SEQ ID NO: 13) |
| PD1 XmaI Primer 2 | GCCCCGGGCTATTAGGGTGAGG (SEQ ID NO: 14) |
| pK-SIRPα | |
| SPRIα NcoI Primer 1 | CGCCATGGGCGTTGCGGGCGAA (SEQ ID NO: 15) |
| SPRIα XmaI Primer 2 | GCCCCGGGCTATTAACGTTCGT (SEQ ID NO: 16) |
| pK-DFZD | |
| FZD KpnI Primer 1 | GGGGTACCACCACCATGGACCACGGCTTCTGCCAGCC (SEQ ID NO: 17) |
| FZD XhoI Primer 2 | GCCGCTCGAGCTATTAGGGAGCTCCGTCCTCGGAGT (SEQ ID NO: 18) |
| pK-DLRP6 | |
| LRP6P KpnI Primer 1 | GGGGTACCACCACCATGGGCATTGTCCCAGAGGCTTTCCT (SEQ ID NO: 19) |
| LRP6P XhoI Primer 2 | GCCGCTCGAGTTCAAGATGAGCTATCATGTTAATAG (SEQ ID NO: 20) |
| pK-DPD-1 | |
| PD1 KpnI Primer 1 | GGGGTACCACCATGGGCTTAGACTCCCCAGACAGGCC (SEQ ID NO: 21) |
| PD1 XhoI Primer 2 | GCCGCTCGAGCTATTAGGGTGAGGGGCTGGGGTGG (SEQ ID NO: 22) |
| pK-DSIRPα | |
| SPRIα KpnI Primer 1 | GGGGTACCACCATGGGAGTGGCGGGTGAGGAGGAG (SEQ ID NO: 23) |
| SPRIα XhoI Primer 2 | GCCGCTCGAGCTATTACCGTTCATTAGATCCAGTGT (SEQ ID NO: 24) |

Building Up Tumor-Targeting Self-Eradicating TRAIL Delivery Vehicles

A human TRAIL-expressing lysis vector pK5079 was constructed by inserting the TRAIL coding sequence into lysis vector pYA3681 to assemble a self-eradicating *Salmonella* lysis system for cancer therapy. The repressor LacI, expressed from the built-in chromosomal lacI gene under arabinose-regulated araC $P_{BAD}$ promoter, will turn off TRAIL synthesis in vitro to avoid the reduced growth rates and a compromised ability to colonization caused by high-level production of foreign protein. Then the tumor-navigating strains GMS410 and GMS515 were armed with TRAIL by carrying plasmid pK5079 for enhanced cancer cell-killing. The strain GMS409(pK5079) was built, without tumor-navigating feature, to serve as a negative control. The expression of TRAIL by pK5079 in GMS strains was confirmed through western blotting analysis.

Figure 3A:
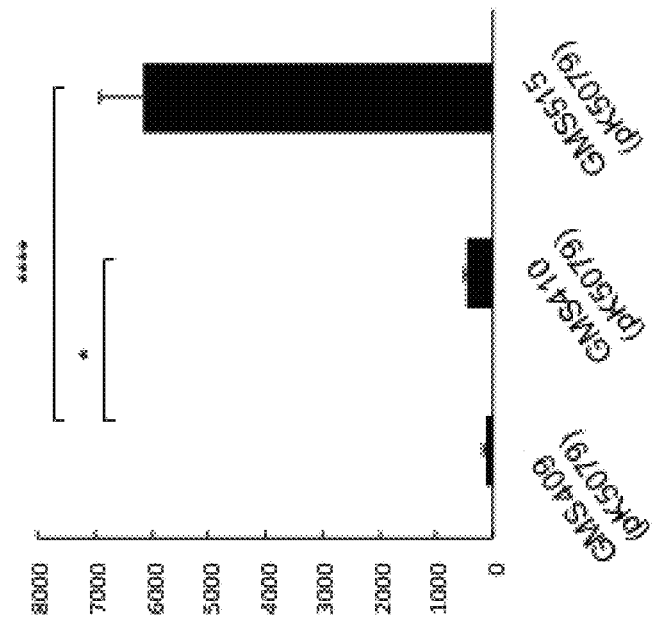
FIGS. 3A-3B demonstrate that the reprogramming chemotaxis system of self-eradicating TRAIL-delivering genetically modified *Salmonella* (GMS) strain facilitates their cancer cell-navigating feature. A. Illustration of transwell assay to determine the colony-forming units (CFU) of GMS swimming cross the swimming agar toward cancer cells. B. The CFU of GMS swimming cross the swimming agar toward human colon cancer cell HCT-116 (*$p<0.05$; $p<0.0001$).
Figure 3B:
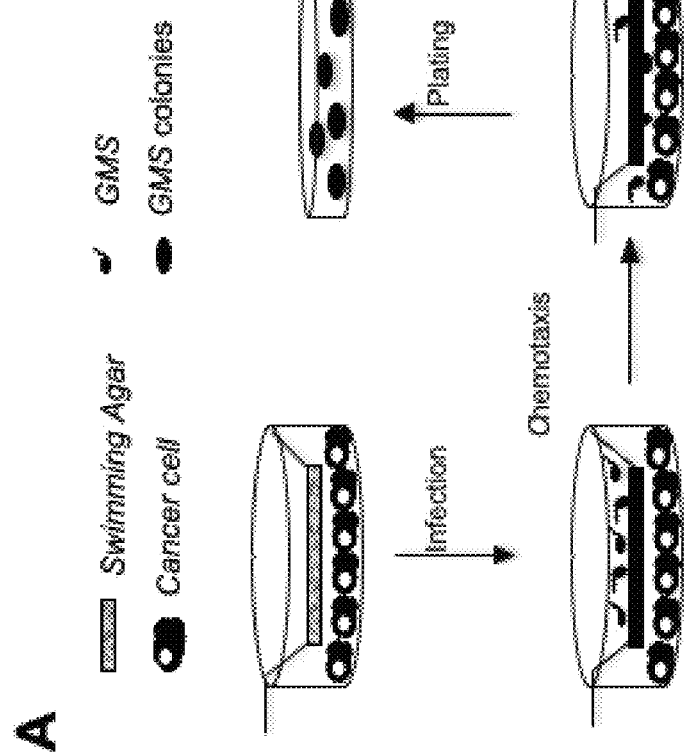
Figure 4:
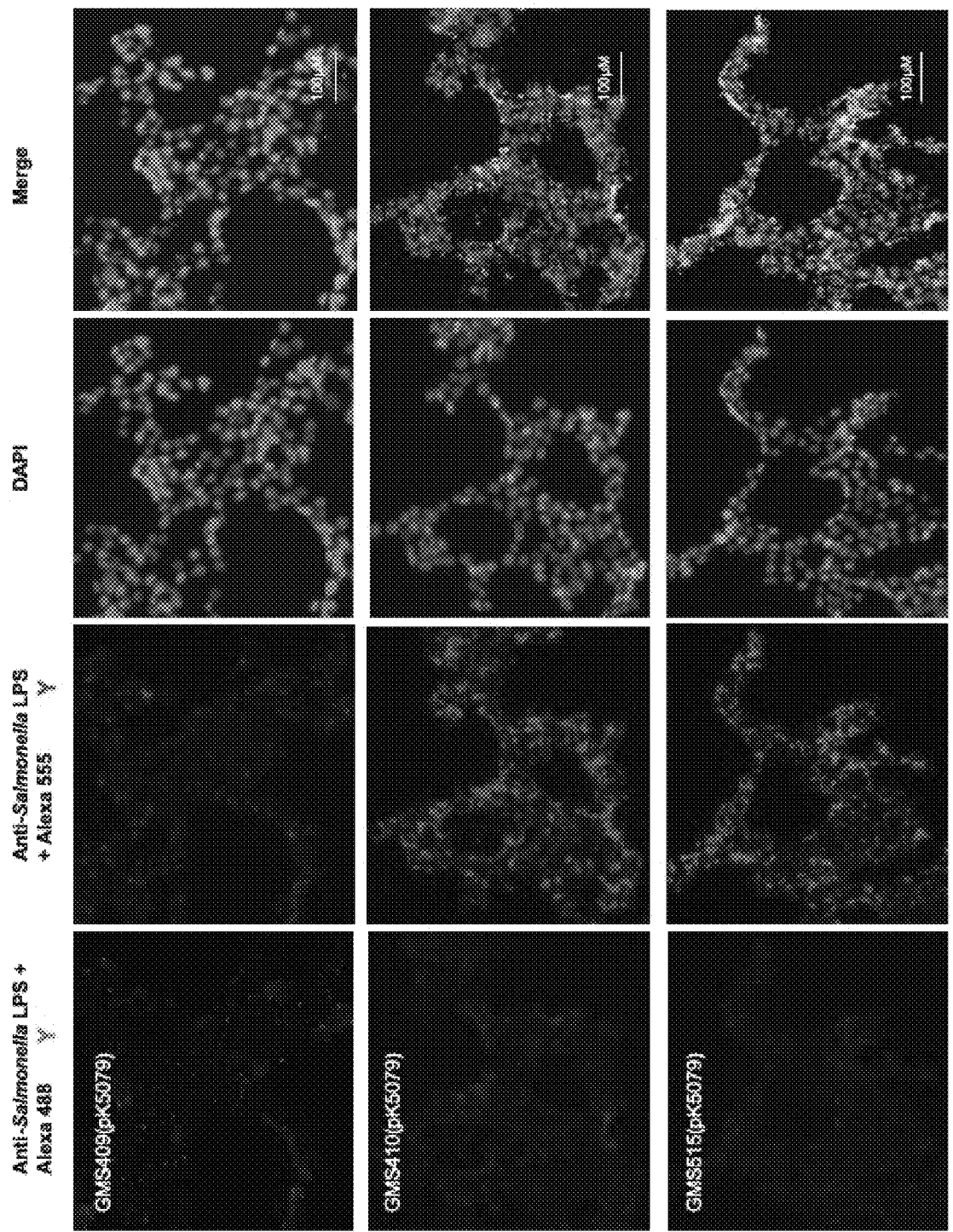
FIG. 4 shows immunofluorescence staining to determine the GMS ability to attach and invade to cancer cells. Green, red, and blue fluorescence indicate HCT-116 cell surface attached *Salmonella*, internalized *Salmonella*, and HCT-116 nucleus, respectively.

Reprogrammed Chemotaxis System Endues GMS Strains Superior Ability of Cancer Cell Seeking, Attaching and Invading To validate whether the GMS with chemoreceptor modifications could obtain cancer cell-navigating feature, a transwell culture system was used. A swimming agar layer was used as a barrier between GMS strains and colon cancer cells. GMS strains were cultured in the upper compartment of the transwell culture system, while human colon cancer HCT-116 cells were grown in the lower compartment. The swimming agar layer and micropores in the insert membrane allow GMS strains to cross freely (FIG. 3A). It was observed that significantly higher numbers of GMS410(pK5079) and GMS515(pK5079) swam across the swimming agar layer toward HCT-116 cells, whereas very little numbers of GMS409(pK5079) did, indicating that reprogrammed chemotaxis system in GMS410(pK5079) and GMS515 (pK5079) endue them the cancer cell-navigating ability to seek cancer cells (FIG. 3B). The capability of GMS strains attaching to and invading cancer cells was also examined. The GMS strains were incubated with HCT-116 cells. We found that more GMS410(pK5079) and GMS515(pK5079) attached to and invaded into CT-26 cells or HCT-116 cells (FIG. 4) comparing to the control strain GMS409(pK5079). These data suggest that chemotaxis system reprogramming in GMS410(pK5079) and GMS515(pK5079) strains to enable them to be better attracted to cancer cells leading to efficient attachment and invasion compared with their parent strain GMS409(pK5079) without genetically engineered chemotaxis system. Overall, the GMS strains with reprogrammed chemotaxis systems possess superior ability to navigate, attach, and invade colon cancer cells.

Reprogrammed GMS Strains Efficiently Induced Colon Cancer Cell Death In Vitro

Figures 5A, 5B:
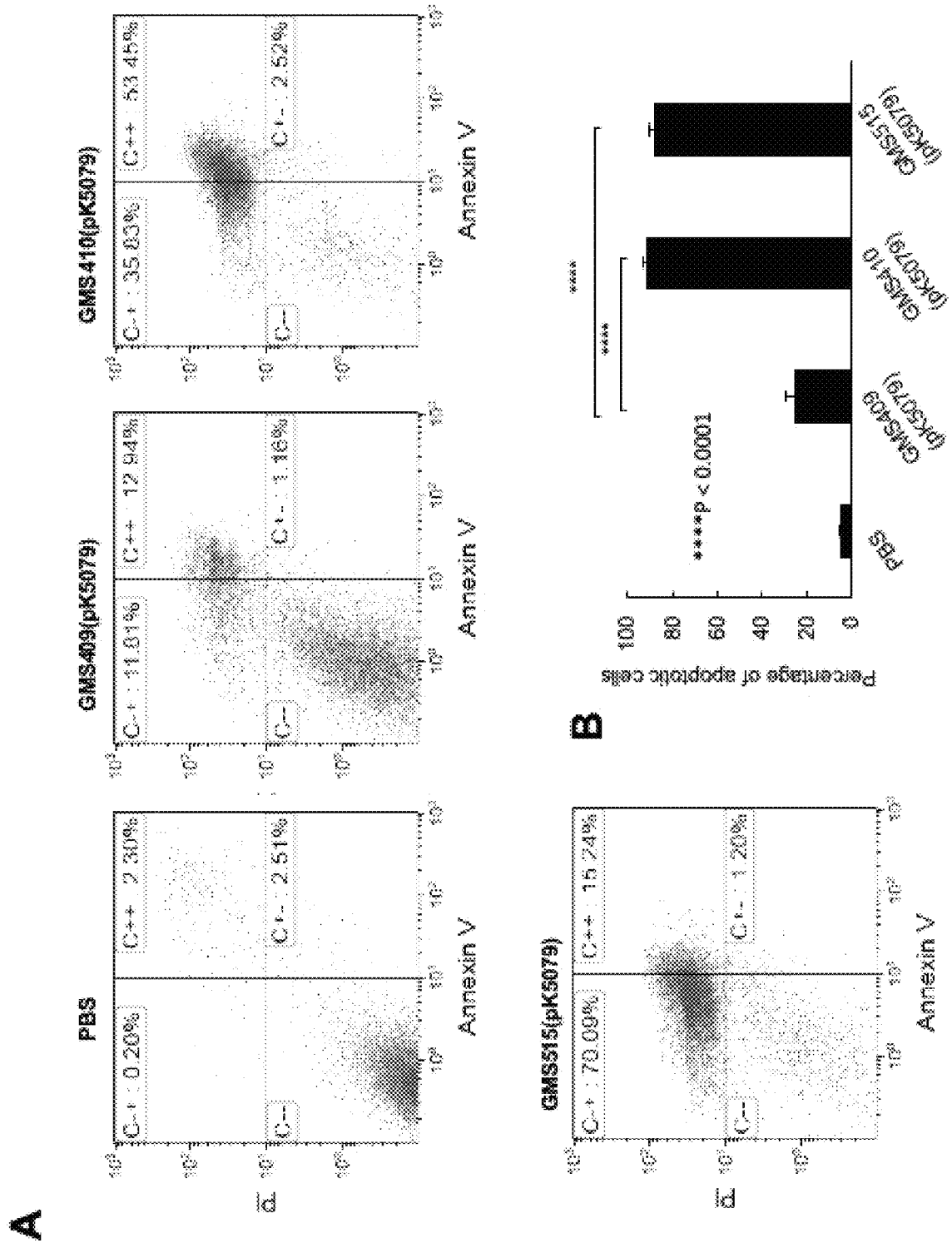
FIGS. 5A-5B demonstrate that reprogrammed GMS strains efficiently induced colon cancer cell death in vitro. A. Representative patterns of apoptosis assays following HCT-116 cells treated with GMS for 16 hours. B. Percentage of apoptotic cells post-treatment. Annexin V-FITC positive HCT-116 cells were expressed as means.

To examine whether the reprogrammed GMS strains have the potential for cancer treatment, the multiple cytotoxic features against cancer cells built into the reprogrammed GMS strains were evaluated in vitro. We first validated the level of activated caspase-3, which is the key "executioner" caspase in the apoptotic cascade, after incubating CT-26 and HCT-116 cells with GMS strains, respectively. It was observed that both cancer cells co-incubated with GMS410 (pK5079) or GMS515(pK5079) had higher levels of active caspase-3 protein and lower levels of pro-caspase-3, comparing to the cells co-incubated with GMS409(pK5079). Our results indicate that the self-eradicating TRAIL delivering GMS strains, with reprogrammed chemotaxis system, are able to promote the apoptotic cascade through caspase-3 activation. To further validate the cancer cell-killing features in reprogrammed GMS strains, the apoptosis assays were performed using the same colon cancer cell lines. Significantly higher percentage of cell death was observed in the HCT-116 samples co-incubated with GMS515(pK5079) and GMS410(pK5079) than the control strain GMS409 (pK5079) (FIGS. 5A-5B). Collectively, the data suggest that the self-eradicating TRAIL-delivering GMS strains with reprogrammed chemotaxis systems hold remarkable cancer cell-killing ability.

Reprogrammed GMS Suppress Tumor Growth In Vivo

The engineered TRAIL-delivering GMS strains with a reprogrammed chemotaxis system, displaying multiple cancer-killing features, have the potential to function as cancer therapeutics. Therefore, the impact of reprogrammed GMS-based therapy on tumor growth, following intra-tumor injection, was evaluated in an allograft colon cancer mouse model. The CT-26 cells were subcutaneously (SQ) injected into the flank area of BALB/c mice. First, the colonization of GMS strains in tumor versus spleen was determined nine days post-intratumoral injection (IT) of $10^8$ CFU bacteria. We found that the reprogrammed GMS410(pK5079) and GMS515(pK5079) strains preferably accumulated in the tumors, after injection of bacteria into the tumors on the mice, growing the bacterial density up to 5,000-13,000 times higher comparing to the density of bacteria found in the spleen. In contrast, strain GMS409(pK5079) without chemoreceptor modification selectively accumulated in *Salmonella* preferred colonization organ, spleen. These data suggested that the reprogrammed chemotaxis system in GMS410(pK5079) and GMS515(pK5079) increased their capacity of tumor specific accumulation that is a key safety feature required for efficient *Salmonella*-based cancer therapy. We then tested whether the GMS strains specifically accumulated in tumor would suppress tumor growth. Phosphate-buffered saline (PBS), GMS409(pK5079), GMS410(pK5079), and GMS515(pK5079) were administrated by IT injection. The tumor sizes were measured every three days post-IT injection of bacteria. The tumor size of mice treated with GMS410(pK5079) or GMS515(pK5079) was significantly smaller than that treated with PBS or control strain GMS409(pK5079) after three days following IT injection. Moreover, both GMS410(pK5079) and GMS515(pK5079) treatments prolonged the lifespan of tumor-bearing mice. The lifespan of tumor-bearing mice was significantly prolonged, which was correlated with suppression of tumor growth, was ascribed to tumor-navigating GMS-mediated oncolysis. To test the hypothesis, immunochemistry staining of Ki67 (an indicator of cancer cell proliferation) and TUNEL (terminal deoxynucleotidyl transferase dUTP nick end-labeling to detect DNA fragmentation as a hallmark of apoptosis) assays were carried out. Many more Ki67 positive cancer cells were observed in the PBS and GMS409(pK5079)-treated tumor samples comparing to the tumor samples from the groups treated with GMS410(pK5079) or GMS515(pK5079). Meanwhile, more apoptotic cells were observed in the tumor sections treated with GMS410(pK5079) or GMS515(pK5079) than in the PBS- or control strain-treated tumors.

Figure 6A:
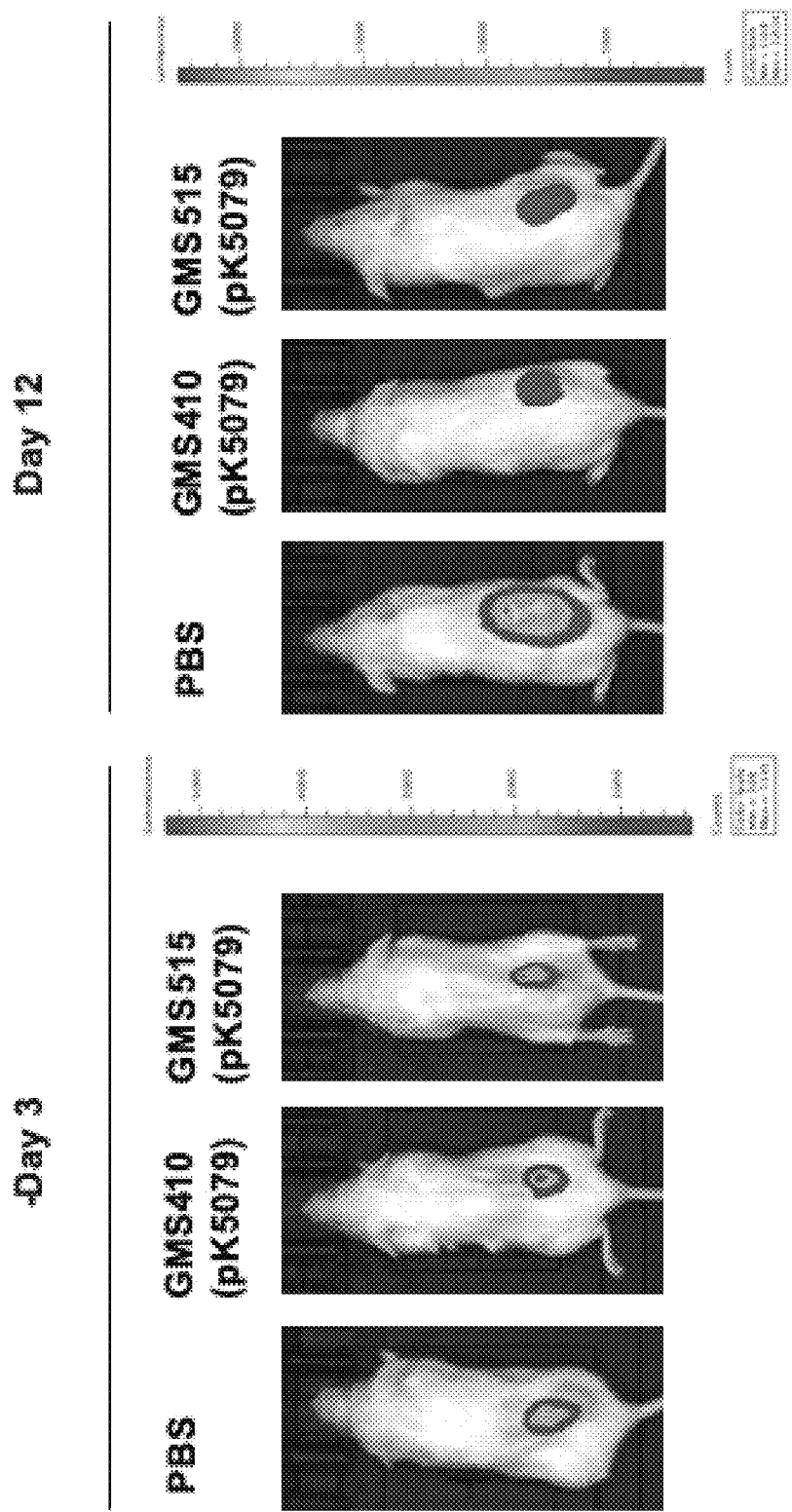
FIGS. 6A-6B demonstrate that reprogrammed GMS strains suppressed tumor growth in HCT-116 SQ tumor model in vivo. A. A set of representative live imaging of NSG™ mice with SQ injected HCT-116 cells captured before and after IT injections of phosphate-buffered saline (PBS) or GMS strain, as indicated. B. Luciferase activities of tumor cells from NSG™ mice before and after GMS strain IT injections were analyzed. The error bar indicates SEM. (n=6, *$p<0.05$). Experiments were repeated independently three times.
Figure 6B:
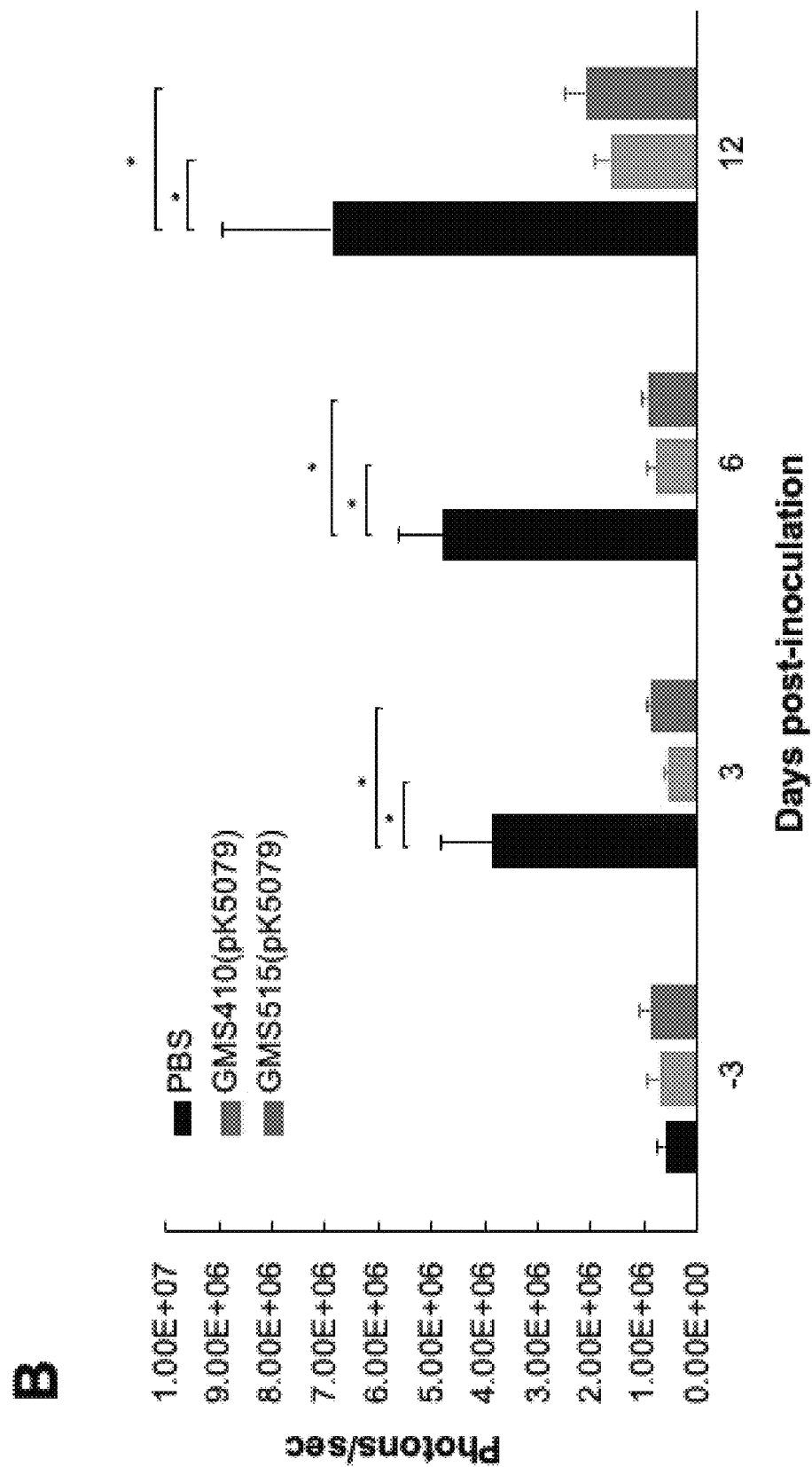

We further evaluated the efficacy of strains GMS410(pK5079) and GMS515(pK5079) on cancer therapy in vivo using a human colon cancer HCT-116 cell xenograft mouse model. HCT-116 cells, which stably express luciferases, were subcutaneously injected into the flank area of immunocompromised NOD. Cg-Prkdcscid Il2rgtm1Wjl/SzJ (NSG™) mice. PBS, GMS410(pK5079), and GMS515(pK5079) were IT injected into the NSG™ mice carrying tumors. The tumor growth was monitored through measuring cancer cell luciferase activity using a live imaging system following IT injection. As shown in FIGS. 6A-6B, the tumor luciferase activity of mice treated with GMS410(pK5079) or GMS515(pK5079) is significantly lower than that in the control tumors (PBS-treated), suggesting that GMS410(pK5079) and GMS515(pK5079) inhibited HCT-116 cancer cell growth in vivo. In addition, Ki67 staining demonstrated that the proliferated cancer cells are much less in tumors treated with GMS410(pK5079) or GMS515(pK5079) than that in the tumors treated with PBS, which confirmed that GMS410(pK5079) and GMS515(pK5079) were also able to inhibit human colon cancer cell growth in vivo. Furthermore, TUNEL assays showed more apoptotic cells in the tumor sections treated with GMS410(pK5079) or GMS515(pK5079) than that in PBS-treated tumor sections. Taken together, these observations suggested that reprogramming of the chemotaxis system was an essential component of the GMS anti-cancer effect and the self-eradicating GMS could effectively deliver TRAIL into the tumor microenvironment, and trigger *Salmonella*- and TRAIL-mediated tumor cell death.

Figures 7A, 7B, 7C:
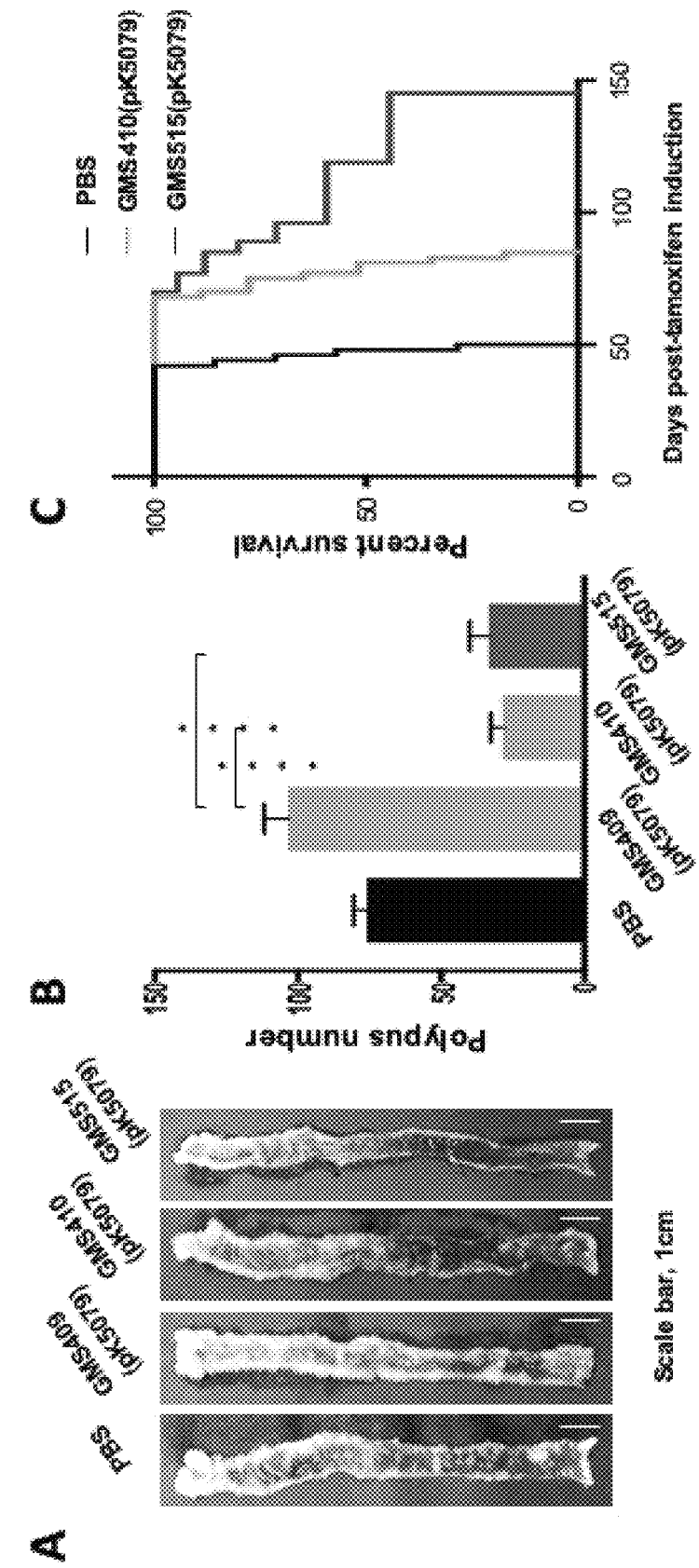
FIGS. 7A-7C demonstrate that reprogrammed GMS strains suppressed tumor progression by promoting cancer cell-killing in a transgenic colon tumor mouse model. A. The representative image of colon from t-APC mice orally inoculated with PBS or GMS strains, as indicated. B. Numbers of polyps from colons of t-APC mice treated with PBS or GMS strains, as indicated (n=8). C. Survival fraction curves of t-APC mice orally treated with PBS or GMS strains 3 times at 10 days interval (n=7).

Evaluation of Reprogrammed GMS Strains Using a Transgenic Colon Tumor Mouse Model In addition to allograft and xenograft subcutaneous tumor models, we evaluated our GMS strains in a transgenic $Apc^{flox/flox}$/CDX2-CRE colon tumor mouse model, which mimic human FAP associated colorectal cancer and sporadic colorectal cancer. Ten days after tamoxifen induction, mice were orally inoculated with PBS, GMS409(pK5079), GMS410(pK5079), and GMS515(pK5079). Tumors in the colons and rectums were counted 10 days post-GMS treatment. As shown in FIGS. 7A-7B, the number of polyps is significantly less in the mice treated with either GMS410(pK5079) or GMS515(pK5079), compared to the number of polyps in the mice treated with the PBS or GMS409(pK5079). Moreover, the survival time of the tamoxifen inducted $Apc^{flox/flox}$/CDX2-CRE mice treated with GMS410(pK5079) and GMS515(pK5079) was dramatically increased when compared with the control group (FIG. 7C). In addition, more positive anti-*Salmonella* immunostaining was observed in the intestinal polyps treated with GMS410(pK5079) and GMS515(pK5079) strains than that in the samples treated with control strain GMS409(pK5079) (FIG. 8). These results suggest that the reprogramming of the chemotaxis system enables GMS410(pK5079) and GMS515(pK5079) to navigate and colonize in tumor tissue following oral inoculation. Furthermore, a TUNEL assay was performed to detect apoptotic cells in the colon polypus. More apoptotic cells were discovered in polypus from the mice treated with GMS410(pK5079) and GMS515(pK5079) than that in the polypus from the mice treated with control GMS409(pK5079) (FIG. 8). Overall, these data further demonstrate that GMS410(pK5079) and GMS515(pK5079) are able to navigate to the tumor and efficiently induce tumor cell apoptosis in vivo.

Figure 9A:
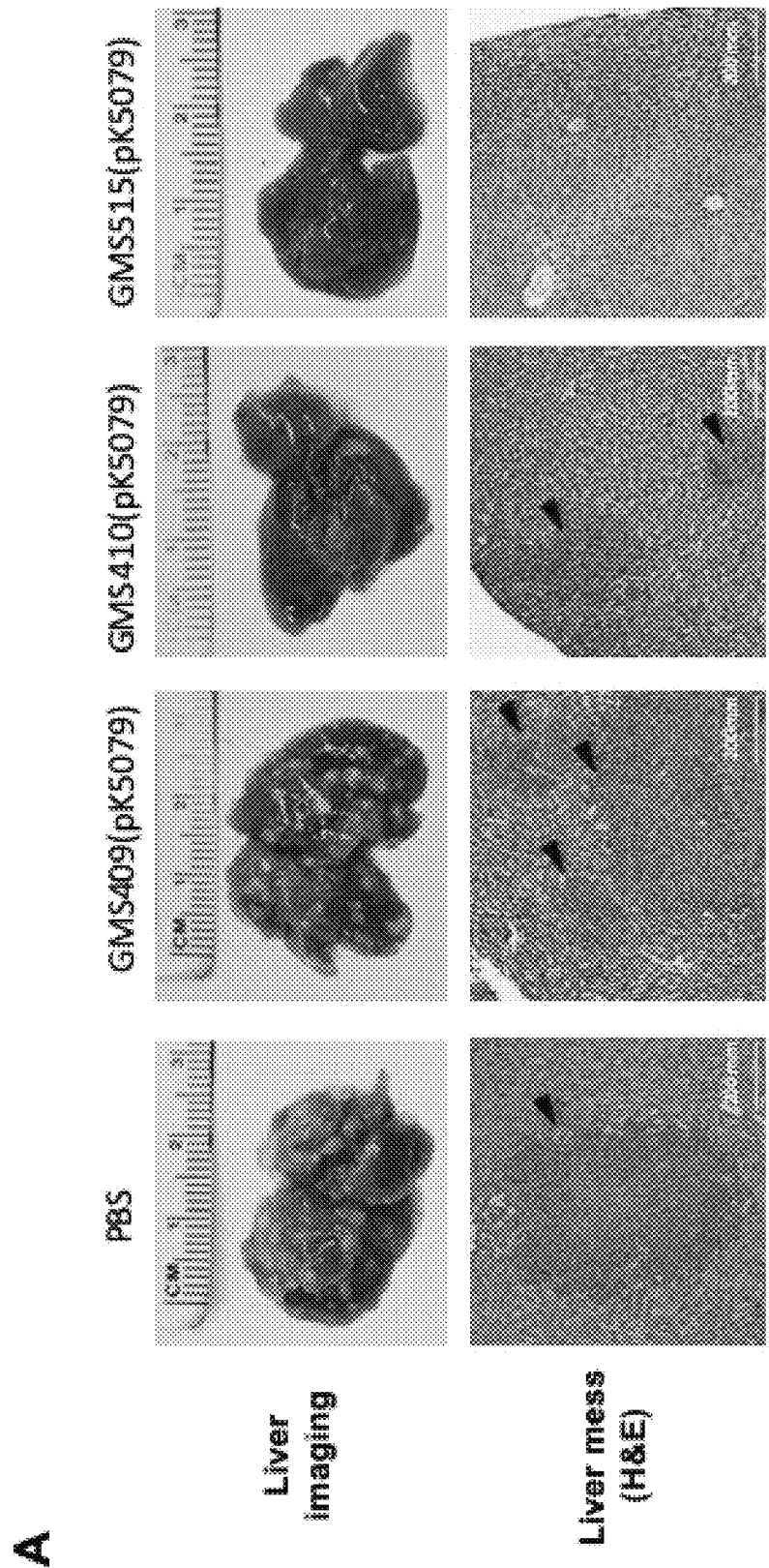
FIGS. 9A-9B demonstrate that reprogrammed GMS strains inhibit liver metastasis in an orthotopic human colon cancer mouse model. A. Representative imaging of liver metastasis (top) and liver section H&E staining (bottom) of the mice treated with PBS or GMS strains, as indicated. B. Numbers of liver metastatic tumors in mice treated with PBS or GMS strains, as indicated (n=12, ***$p<0.001$).
Figure 9B:
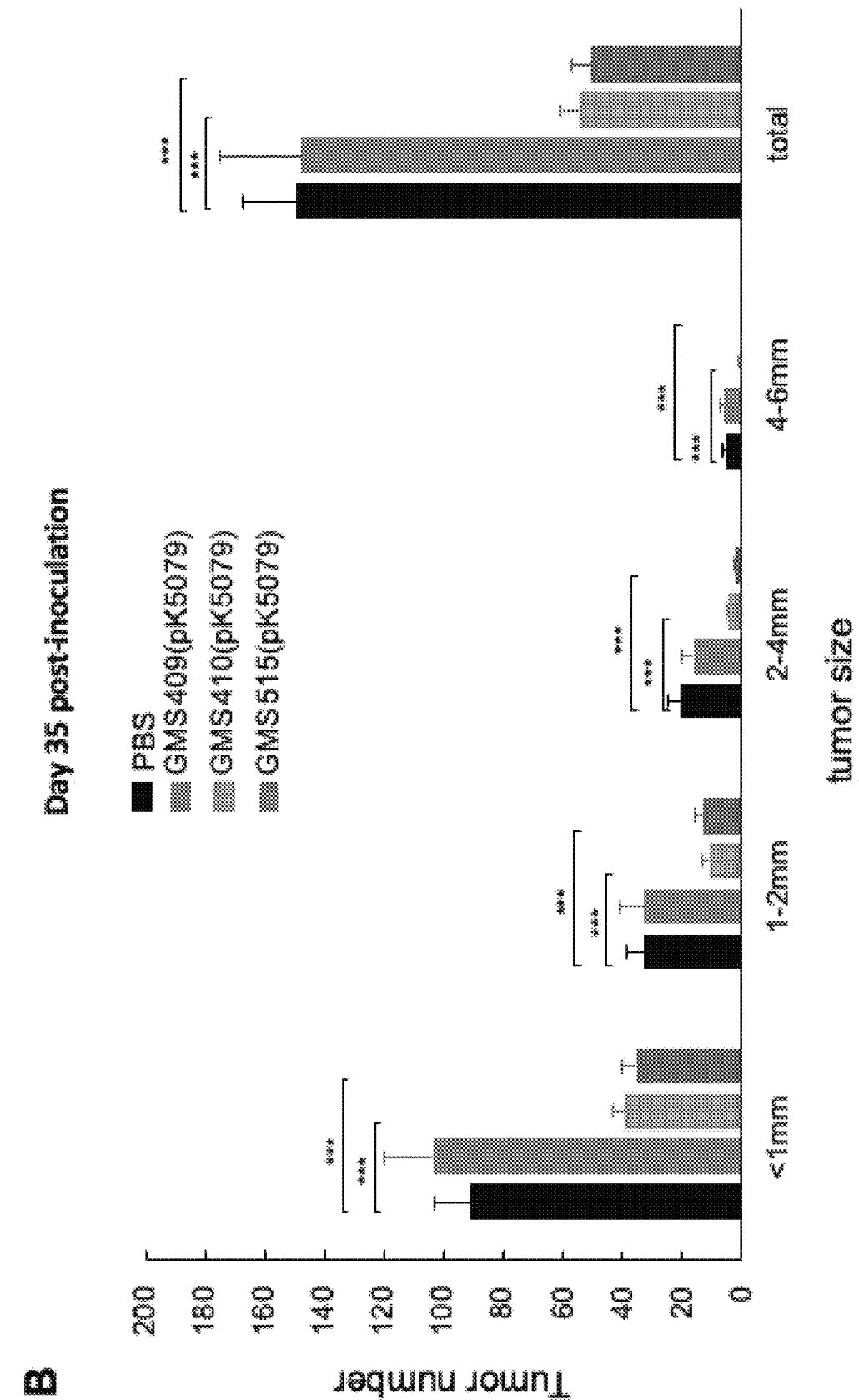

Reprogrammed GMS Strains-Based Therapy for Metastatic Cancer in an Orthotopic Xenograft Mouse Model Colorectal cancer is one of the leading causes of cancer mortality because of its metastasis. Liver is the most common organ for colon cancer metastasis. To investigate whether GMS410(pK5079) and GMS515(pK5079) are able to inhibit liver metastasis from orthotopically implanted colon cancer, the HCT-116 cells expressing luciferase were injected into the cecum wall of NSG™ mice. At day 7 post-surgery, mice were orally inoculated with PBS, GMS409(pK5079), GMS410(pK5079), or GMS515(pK5079) once per week for 5 weeks. Tumor growth and metastasis were monitored using a live imaging system. Metastatic tumor number and size were analyzed at week 5 post-inoculation. As shown in FIGS. 9A-9B, colon cancer cells grew from cecum and metastasized to adjacent tissue and distant organ liver in the groups treated with PBS and GMS409(pK5079). However, much less local and distance metastasis was observed in the mice treated with GMS410 (pK5079) or GMS515(pK5079). These data indicate that both GMS410(pK5079) and GMS515(pK5079) are capable of reducing tumor metastasis.

Discussion

Despite many advances in conventional methods such as chemo- and radiation-therapy, cancer treatment is still far from optimal. Current cancer therapies frequently encounter challenges including nonspecific systemic distribution of antitumor agents, inadequate drug concentrations reaching the tumor site, intolerable cytotoxicity and development of multiple drug resistance. As with any cancer therapy, the key issue is to achieve the desired concentration of the therapeutic agent specifically in tumor sites, thereby destroying cancerous cells while minimizing damage to normal cells. Bacterial cancer therapies offer unique features that can overcome these obstacles. However, intrinsic bacterial toxicity and tumor-targeting efficiency are two major concerns for the bacterial approach in cancer therapy. We report here that we have now addressed the concerns by constructing GMS strains with enhanced chemotaxis systems that are attracted by tumor-released small molecules to confer tumor-navigating features. Moreover, the regulated delayed attenuation and programmed self-eradicating features designed into these S. Typhimurium strains to enable them to efficiently colonize in tumors and allow the release of a target agent (e.g., a tumoricidal protein such as TRAIL, another protein) after cell lysis. As proof of concept, we have demonstrated that the genetically engineered tumor navigating and self-eradicating GMS410(pK5079) and GMS515 (pK5079) strains not only improve the safety of cancer treatment, but also efficiently target tumor tissue and release a target agent into the tumor tissues to significantly affect tumor growth and extend the survival rate in both allograft and xenograft colon cancer mouse models. We also validate the efficacy of anti-cancer metastasis using *Salmonella* based-cancer therapies in the orthotopic human colon cancer xenograft mouse model created through cecum wall surgical microinjection, which drives tumor foci to the most relevant metastatic sites observed in humans. Most importantly, orally administered GMS410(pK5079) and GMS515 (pK5079) successfully achieved metastasis blockage in such mouse models. In addition, we are the first to evaluate *Salmonella*-based cancer therapeutics in an inducible APC gene mutation mouse model, which can better mimic human familial adenomatous polyposis disease. The results proved that GMS410(pK5079) and GMS515(pK5079) strains effectively suppressed tumor progression. As such, these GMS strains show tremendous potential, either alone or in combination with other treatments, to make an important contribution in cancer therapy.

The present disclosure has described one or more preferred embodiments, and it should be appreciated that many equivalents, alternatives, variations, and modifications, aside from those expressly stated, are possible and within the scope of the disclosure.

We claim:

1. A genetically modified *Salmonella* bacterium comprising:
   (i) a recombinant gene encoding a human decoy polypeptide;
   (ii) the following modifications $\Delta P_{murA25}$::TT araC $P_{BAD}$ murA, $\Delta$(wcaM-wca)-8, $\Delta$relA198::araC $P_{BAD}$ lacITT, $\Delta$(araC $P_{BAD}$)-18::P22 $P_R$ araBAD, $\Delta$pagP81::$P_{lpp}$ IpxE, and $\Delta$endA1123;
   (iii) the following modifications $\Delta P_{tar}$::$P_{trc\ \Delta lacO888}$ tar, $\Delta P_{tsr}$::$P_{trc\ \Delta lacO888}$ tsr, and $\Delta$trg.

2. The genetically modified *Salmonella* bacterium of claim 1, wherein the decoy polypeptide disrupts Wnt/β-catenin signaling.

3. The genetically modified *Salmonella* bacterium of claim 1, wherein the decoy polypeptide is selected from a soluble form of human frizzled (FZD) receptor, a soluble form of human low-density lipoprotein receptor-related protein 6 (LRP6), a soluble form of human programmed cell death protein 1 (PD-1), and a soluble form of human signal regulatory protein alpha (SIRP-alpha).

* * * * *